(12) United States Patent
Fricke et al.

(10) Patent No.: US 11,274,317 B2
(45) Date of Patent: *Mar. 15, 2022

(54) TARGETED RNA KNOCKDOWN AND KNOCKOUT BY TYPE III-A CSM COMPLEXES

(71) Applicant: VILNIUS UNIVERSITY, Vilnius (LT)

(72) Inventors: Thomas Fricke, Warsaw (PL); Matthias Bochtler, Piacezno (PL); Gintautas Tamulaitis, Vilnius (LT); Miglé Kazlauskiene, Vilnius (LT); Virginijus Šikšnys, Vilnius (LT)

(73) Assignee: VILNIUS UNIVERSITY, Vilnius (LT)

( * ) Notice: Subject to any disclaimer, the term of this patent is extended or adjusted under 35 U.S.C. 154(b) by 323 days.

This patent is subject to a terminal disclaimer.

(21) Appl. No.: 15/692,866

(22) Filed: Aug. 31, 2017

(65) Prior Publication Data

US 2018/0105835 A1  Apr. 19, 2018

Related U.S. Application Data

(63) Continuation-in-part of application No. 15/448,818, filed on Mar. 3, 2017, which is a continuation-in-part of application No. PCT/IB2015/056756, filed on Sep. 4, 2015.

(60) Provisional application No. 62/046,384, filed on Sep. 5, 2014.

(51) Int. Cl.
| | |
|---|---|
| C12N 15/85 | (2006.01) |
| C07K 14/315 | (2006.01) |
| C12N 15/113 | (2010.01) |
| C12N 9/22 | (2006.01) |

(52) U.S. Cl.
CPC ........ *C12N 15/8509* (2013.01); *C07K 14/315* (2013.01); *C12N 9/22* (2013.01); *C12N 15/113* (2013.01); *A01K 2217/058* (2013.01); *A01K 2217/07* (2013.01); *A01K 2227/40* (2013.01); *A01K 2267/0306* (2013.01); *A01K 2267/0393* (2013.01); *C12N 2310/11* (2013.01); *C12N 2310/20* (2017.05); *C12N 2310/3233* (2013.01); *C12N 2310/3519* (2013.01); *C12N 2310/531* (2013.01); *C12N 2320/30* (2013.01)

(58) Field of Classification Search
None
See application file for complete search history.

(56) References Cited

U.S. PATENT DOCUMENTS 10,385,336 B2 * 8/2019 Siksnys ............... C12Y 301/27
2010/0076057 A1    3/2010 Sontheimer et al.

FOREIGN PATENT DOCUMENTS

| WO | WO 1995/029244 A1 | 11/1995 |
|---|---|---|
| WO | WO 1999/014346 A2 | 3/1999 |
| WO | WO 2007-025097 A2 | 3/2007 |
| WO | WO 2012-164565 A1 | 12/2012 |

OTHER PUBLICATIONS

Staals, et al. (2014) "RNA Targeting by the Type III-A CRISPR/Cas Csm Complex of Thermus thermophilus", Molecular Cell, 56: 518-30.*
Sunghyeok et al.; "DNA-dependent RNA cleavage by the Natronobacterium gregoryi Argonaute"; bioRxiv beta—The Preprint Server for Biology; Jan. 2017; 9 pages.
Abudayyeh et al. (2016). C2c2 is a single-component programmable RNA-guided RNA-targeting CRISPR effector. Science, 353, 17 pages.
Altschul et al. (1997). Gapped BLAST and PSI-BLAST: a new generation of protein database search programs. Nucleic Acids Res 25, 3389-3402.
Ashkenazy et al. (2010). ConSurf 2010: calculating evolutionary conservation in sequence and structure of proteins and nucleic acids. Nucleic Acids Res, 38, W529-533.
Baker et al. (2001). Electrostatics of nanosystems: application to microtubules and the ribosome. Proc Natl Acad Sci USA, 98, 10037-10041.
Bill et al. (2009). A primer for mopholino use in zebrafish. Zebrafish, 6, 69-77.
Braat et al. (1999). Characterization of zebrafish primordial germ cells: morphology and early distriction of vasa RNA. Developmental Dynamics, 216, 153-167.
Braat et al. (2000). Vasa protein expression and localization in the zebrafish. Mechanisms of Development, 95, 271-274.
Brouns et al. (2008). Small CRISPR RNAs guide antiviral defense in prokaryotes. Science, 321, 960-964.
Burgess et al. (2017). Questions about ngAgo. Protein & Cell, 7(12), 913-915.
Carte et al. (2008). Cas6 is an endoribonuclease that generates guide RNAs for invader defense in prokaryotes. Genes & Development, 22, 3489-3496.
Chen and Fishman (1996). Zebrafish tinman homolog demarcates the heart field and initiates myocardial differentiation. Development, 122, 3809-3816.
Deng et al. (2013). A novel interference mechanism by a type IIIB CRISPR-Cmr module in Sulfolobus. Molecular Microbiology, 87, 1088-1099.
De Rienzo et al. (2012). Efficient shRNA-mediated inhibition of gene expression in zebrafish. Zebrafish, 9, 97-107.

(Continued)

*Primary Examiner* — Robert M Kelly
(74) *Attorney, Agent, or Firm* — Nixon & Vanderhye

(57) ABSTRACT

Methods and compositions using a CRISPR-Cas Type IIIA resulting in RNA gene knockdown and knockout in an animal.

15 Claims, 71 Drawing Sheets
(18 of 71 Drawing Sheet(s) Filed in Color)
Specification includes a Sequence Listing.

(56) References Cited

OTHER PUBLICATIONS

Dickman and Hornby (2006). Enrichment and analysis of RNA centered on ion pair reverse phase methodology. RNA, 12, 691-696.
East-Seletsky et al. (2016). Two distinct Rnase activies of CRISPR-C2c2 enagle guide-RNA processing and RNA detection. Nature, 538, 17 pages.
Eisen et al. (2008). Controlling morpholino experiments: don't stop making antisense. Development, 135, 1735-1743.
Fischer et al. (2010). Determination of the molecular weight of proteins in solution from a single small-angle X-ray scattering measurement on a relative scale. J Appl Crystallogr, 43, 101-109.
Frickey and Lupas (2004). CLANS: a Java application for visualizing protein families based on pairwise similarity. Bioinformatics, 20, 3702-3704.
Gao et al. (2016). DNA-guided genome editing using the Natronobacterium gregoryl Argonaute. Nature Biotechnology, 34, 7 pages.
Gasiunas et al. (2012). Cas9-crRNA ribonucleoprotein complex mediates specific DNA cleavage for adaptive immunity in bacteria. Proc Natl Acad Sci USA, 109, E2579-2586.
Goldberg et al. (2014). Conditional tolerance of temperate phages via transcription-dependent CRISPR-Cas targeting. Nature, 514, and Supplementary Information; 24 pages.
Hale et al. (2009). RNA-guided RNA cleavage by a CRISPR RNA-Cas protein complex. Cell, 139, 945-956.
Hatoum-Aslan et al. (2011). Mature clustered, regularly interspaced, short palindromic repeats RNA (crRNA) length is measured by a ruler mechanism anchored at the precursor processing site. Proc Natl Acad Sci USA, 108, 21218-21222.
Hatoum-Aslan et al. (2013). A ruler protein in a complex for antiviral defense determines the length of small interfering CRISPR RNAs. The Journal of Biological Chemistry, 288, 27888-27897.
Hatoum-Aslan et al. (2014). Genetic characterization of antiplasmid immunity through a type III-A CRISPR-Cas system. J Bacteriol, 196, 310-317.
Heasman (2002). Morpholino oligos: making sense of antisense? Developmental Biology, 243, 209-214.
Horvath and Barrangou (2010). CRISPR/Cas, the immune system of bacteria and archaea. Science, 327, 167-170.
Hrle et al. (2013). Structure and RNA-binding properties of the type III-A CRISPR-associated protein Csm3. RNA Biology 10, 1670-1678.
Huang et al. (2003). Germ-line transmission of a myocardium-specific GFP transgene reveals critical regulatory elements in the cardiac myosin light chain 2 promoter of zebrafish. Developmental Dynamics, 228, 30-40.
Huang et al. (2010). Characterising and predicting haploinsufficency in the human genome. PloS Genetics, 6, 11 pages.
Jinek et al. (2012). A programmable dual-RNA-guided DNA endonuclease in adaptive bacterial immunity. Science, 337, 816-821.
Jung et al. (2015). Crystal Strucure of the Csm1 subunit of the Csm Complex and its single-stranded DNA-specific nuclease activity. Structure, 23, 9 pages.
Katoh et al. (2002). MAFFT: a novel method for rapid multiple sequence alignment based on fast Fourier transform. Nucleic Acids Res, 30, 3059-3066.
Kaya et al. (2016). A bacterial Argonaute with noncanonical guide RNA specificity. Proc Natl Acad Sci USA, 113, 4057-4062 and Supporting Information, 8 pages.
Kazlauskiene et al. (2016). Spatiotemporal Control of Type III-A CRISPR-Cas Immunity: Coupling DNA Degradation with the Target RNA Recognition. Molecular Cell, 62, 295-306 and Supplemental Information, 17 pages.
Kim et al. (2008). Real-time imaging of mitochondria in transgenic zebrafish expressing mitochondrially targeted GFP. Biotechniques, 45, 331-334.

Knaut et al. (2000). Zebrafish vasa RNA but not its protein is a component of the germ plasm and segrates asymmetrically before germline specification. The Journal of Cell Biology, 149, 875-888.
Knaut et al. (2002). An evolutionary conserved region in the vasa 3'UTR targets RNA translation to the germ cells in the zebrafish. Current Biology, 12, 454-466.
Kok et al., (2015). Reverse genetic screening reveals poor correlation between morpholino-induced and mutant phenotypes in zebrafish. Dev Cell, 32, 97-108.
Kozin and Svergun (2001). Automated matching of high- and low-resolution structural models. J Appl Crystallogr, 33, 33-41.
Kraulis (1991). MOLSCRIPT: A program to produce both detailed and schematic plots of protein structures. J Appl Crystallogr, 24, 945-950.
Krovel et al. (2002). Expression of a vas::EGFP transgene in primordial germ cells of the zebrafish. Mechanisms of Development, 116, 141-150.
Lawson et al. (2002). In vivo imaging of embryonic vascular development using transgenic zebrafish. Developmental Biology, 248, 307-318.
Lee et al. (2017). Failure to detect DNA-guided genome editing using Natronobacterium gregoryl Argonaute. Nature Biotechnology, 35, 17-18.
Lister et al. (1999). Nacre encodes a zebrafish microphthalmia-related protein that regulates neural-crest-derived pigment cell fate. Development, 126, 3757-3767.
Liu et al. (2005). Efficient RNA interference in zebrafish embryos using siRNA synthesized with SP6 RNA polymerase. Dev Growth Differ, 47, 323-331.
Makarova et al. (2006). Comparative genomics of the lactic acid bacteria. Proc Natl Acad Sci USA, 103, 15611-15616.
Makarova et al. (2011a). Unification of Cas protein families and a simple scenario for the origin and evolution of CRISPR-Cas systems. Biology Direct, 6, 38.
Makarova et al. (2011b). Evolution and classification of the CRISPR-Cas systems. Nature reviews. Microbiology, 9, 467-477.
Marraffini and Sontheimer (2008). CRISPR interference limits horizontal gene transfer in *staphylococci* by targeting DNA. Science, 322, 1843-1845.
Marraffini and Sontheimer (2010). CRISPR interference: RNA-directed adaptive immunity in bacteria and archaea. Nature reviews. Genetics, 11, 181-190.
Merritt and Bacon (1997). Raster3D: Photorealistic molecular graphics. Methods in Enzymology, 277, 505-524.
Millen et al. (2012). Mobile CRISPR/Cas-mediated bacteriophage resistance in Lactococcus lactic. PLoS One, 7, e51663.
Mojica et al. (2009). Short motif sequences determine the targets of the prokaryotic CRISPR defence system. Microbiology, 155, 733-740.
Nasevicius and Ekker (2000). Effective targeted gene 'knockdown' in zebrafish. Nature Genetics, 26, 216-220.
Neuhauss et al. (1999). Genetic disorders of vision revealed by a behavioral screen of 400 essential loci in zebrafish. The Journal of Neuroscience, 19, 8603-8615.
Olsthoorn and van Duin (2011). Bacteriophages with ssRNA. In eLS (John Wiley & Sons Ltd, Chichester), pp. 1-8.
Petoukhov et al. (2012). New developments in the ATSAS program package for small-angle scattering data analysis. J Appl Crystallogr, 45, 342-350.
Qi et al. (2016). NgAgo-based fabp11a gene knockdown causes eye developmental defects in zebrafish. Cell Research, 26, 1349-1352.
Rossi et al. (2015). Genetic compensation induced by deleterious mutations but not gene knockdowns. Nature 524, 15 pages.
Rouillon et al. (2013). Structure of the CRISPR interference complex CSM reveals key similarities with cascade. Mol Cell, 52, 124-134.
Samai et al. (2015). Co-transcriptional DNA and RNA Cleavage during Type III CRISPR-Cas Immunity. Cell, 161, 1164-1174 and Supplemental Figures, 7 pages.
Schrodinger, LLC (2010). The PyMOL Molecular Graphics System, Version 1.3r1.

(56) References Cited

OTHER PUBLICATIONS

Shmakov et al. (2015). Discovery and Functional Characterization of Diverse Class 2 CRISPR-Cas Systems. Molecular Cell, 60, 13 pages.
Sinkunas et al. (2013). In vitro reconstitution of Cascade-mediated CRISPR immunity in *Streptococcus thermophilus*. EMBO J, 32, 385-394.
Soding et al. (2005). The HHpred interactive server for protein homology detection and structure prediction. Nucleic Acids Res, 33, W244-248.
Spilman et al. (2013). Structure of an RNA silencing complex of the CRISPR-Cas immune system. Mol Cell, 52, 146-152.
Staals et al. (2013). Structure and activity of the RNA-targeting Type III-B CRISPR-Cas complex of Thermus thermophilus. Mol Cell, 52, 135-145.
Staals, R.H et al. (2014). RNA targeting by the Type III-A CRISPR-Cas Csm Complex of Thermus thermophilus. Mol Cell, 56(4), 518-530.
Stainier et al., (2015). Making sense of anti-sense data. Developmental Cell, 32, 7-8.
Sternberg et al. (2014). DNA interrogation by the CRISPR RNA-guided endonuclease Cas9. Nature, 507, 62-67.
Svergun (1992). Determination of the regularization parameter in indirect-transform methods using perceptual criteria. J Appl Crystallogr, 25, 495-503.
Svergun (1999). Restoring low resolution structure of biological macromolecules from solution scattering using simulated annealing. Biophysical journal, 2879-2886.
Szczelkun et al. (2014). Direct observation of R-loop formation by single RNA-guided Cas9 and Cascade effector complexes. Proc Natl Acad Sci USA, 111, 9798-9803.
Tamulaitis et al. (2014). Programmable RNA Shredding by the Type III-A CRISPR-Cas System of *Streptococcus thermphilus*. Mol Cell 56(4), 506-517.
Tamulaitis et al. (2016). Type III CRISPR-Cas Immunity: Major Differences Brushed Aside. Trends in Microbiology, 25(1), 13 pages.
Terns and Terns (2014). CRISPR-based technologies: prokaryotic defense weapons repurposed. Trends in genetics. TIG, 30, 111-118.
Volkov and Svergun (2003). Uniqueness of it ab initio shape determination in small-angle scattering. J Appl Crystallogr, 36, 860-864.
Waghmare et al. (2009). Studying the mechanism of RNA separations using RNA chromatography and its application in the analysis of ribosomal RNA and RNA:RNA interactions. Journal of chromatography. A, 1216, 1377-1382.
Westerfield (1993). The zebrafish book: a guide for the laboratory use of zebrafish (*Brachydanio rerio*). Eugene, OR. Ch. 1 & 2, 39 pages, Institute of Neuroscience, University of Oregon, Eugene, OR, 1993, University of Oregon Press Publisher.
Westra et al. (2012). CRISPR immunity relies on the consecutive binding and degradation of negatively supercoiled invader DNA by Cascade and Cas3. Mol Cell, 46, 595-605.
White et al. (2008). Transparent adult zebrafish as a tool for in vivo transplantation analysis. Cell Stem Cell, 2, 183-189.
Wiedenheft et al. (2011). Structures of the RNA-guided surveillance complex from a bacterial immune system. Nature, 477, 486-489.
Witzel et al. (2012). The LIM protein Ajuba restricts the second heart field progenitor pool by regulating lsl1 activity. Developmental Cell, 23, 58-70.
Zhang et al. (2012). Structure and mechanism of the CMR complex for CRISPR-mediated antiviral immunity. Mol Cell, 45, 303-313.
Zheng et al. (2004). An efficient one-step site-directed and site-saturation mutagenesis protocol. Nucleic Acids Res, 32, e115.
International Search Report and Written Opinion from grandparent PCT/IB2015/056756, dated Dec. 18, 2015, 12 pages.
Marraffini et al.; Self versus non-self discrimination during CRISPR RNA-directed immunity; Nature; 2010; 18 pages w/ Supplemental Information.
Short et al.; Structural Determinants for Post-transcriptional Stabilization of Lactate Dehydrogenase A mRNA by the Protein Kinase C Signal Pathway; The Journal of Biological Chemistry; vol. 275 No. 17; Apr. 2000; p. 12963-12969.
Provost et al.; Length Increase of the Human a-Globin 3'-Untranslated Region Disrupts Stability of the Pre-mRNA but Not That of the Mature mRNA; The Journal of Biological Chemistry; vol. 275 No. 39; Sep. 2000; p. 30248-30255.
Dean et al.; The 3' Untranslated Region of Tumor Necrosis Factor Alpha mRNA Is a Target of the mRNA-Stabilizing Factor HuR; Molecular And Cellular Biology; vol. 21 No. 3; Feb. 2001; p. 721-730.
Maurer et al.; An AU-rich sequence in the 3'-UTR of plasminogen activator inhibitor type 2 (PAI-2) mRNA promotes PAI-2 mRNA decay and provides a binding site for nuclear HuR; Nucleic Acids Research; vol. 27 No. 7; 1999; p. 1664-1673.
Veyrune et al.; c-fos mRNA instability determinants present within both the coding and the 3' non coding region link the degradation of this mRNA to its translation; Oncogene; vol. 11; 1995; p. 2127-2134.

\* cited by examiner

1 — NA from Csm complex
2 — NA + DNaseI
3 — NA + RNaseI

FIG. 5A-1

| | |
|---|---|
| Csm3 S.thermophilus | Line 1 |
| Csm3 S.epidermidis | Line 2 |
| Csm3 L.lactis | Line 3 |
| Csm3 M.kandleri | Line 4 |
| Ssol425 S.solfataricus | Line 5 |
| Ssol426 S.solfataricus | Line 6 |
| Cmr4 T.thermophilus | Line 7 |
| Cmr4 P.furiosus | Line 8 |
| Cmr4 S.solfataricus | Line 9 |

FIG. 6A-2

FIG. 8 con't
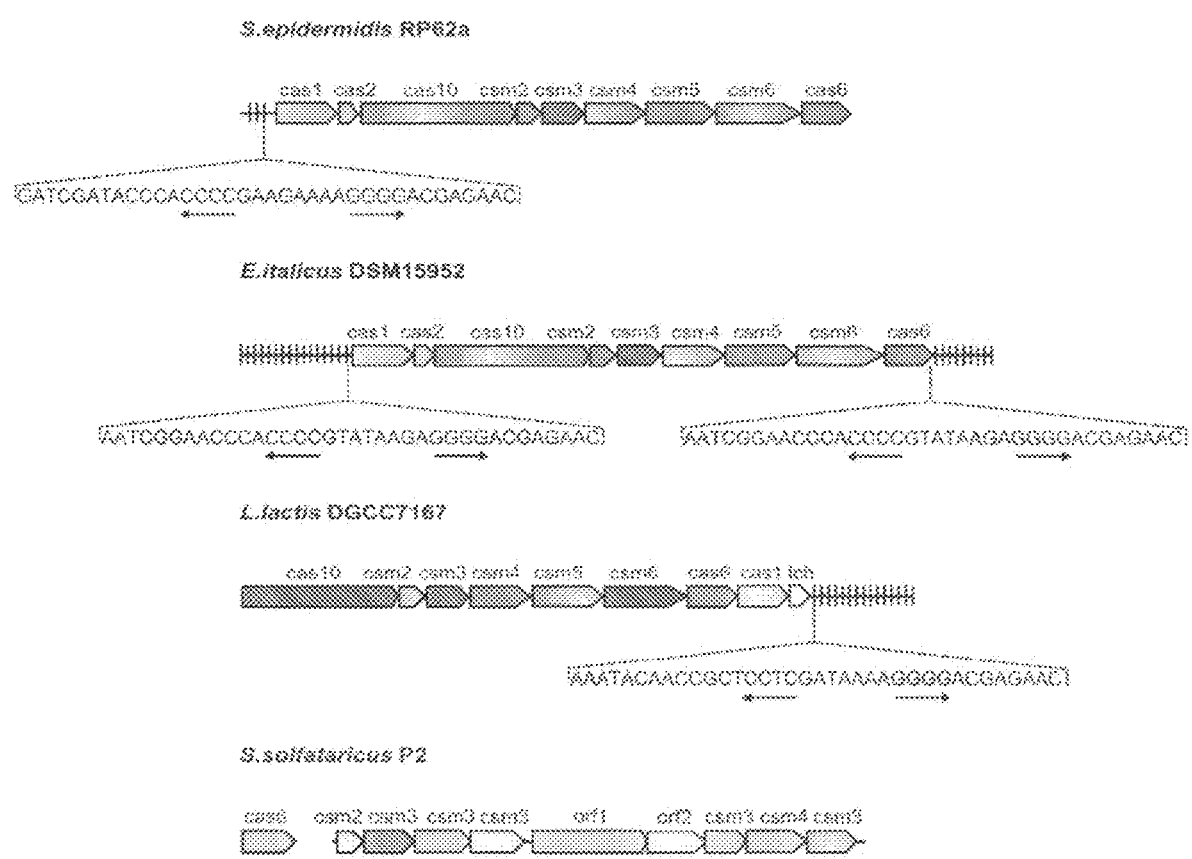

| Position | Theoretical mass (Da) | Experimental Mass (Da) | Sequence |
|---|---|---|---|
| A5:G13 | 2879.725 | 2879.529 | AAACUUCGp |
| U20:G29 | 3163.839 | 3163.663 | UUUAAUUCUGp |
| U30:G46 | 5018.989 | 5018.918 | UUCACUUAUUCCACCGp |
| A46:G65 | 6359.830 | 6359.347 | AUAUAAACCUAAUUACCUCGp |

| Position | Theoretical mass (Da) | Experimental Mass (Da) | Sequence |
|---|---|---|---|
| G3:C8 | 2001.244 | 2001.3 | GGAAACp |
| A50:C53 | 1310.279 | 1310.3 | AAACp |
| G65:G72 | 2747.306 | 2747.4 | GAGAGGGGp |

| Position | Theoretical mass (Da) | Experimental Mass (Da) | Sequence |
|---|---|---|---|
| A5:G13 | 2879.725 | 2879.526 | AAACUUUCGp |
| U20:G29 | 3163.839 | 3163.381 | UUUAAUUCUGp |
| U30:C40 | 3349.019 | 3348.906 | UUCACUUAUUC |
| U30:G45 | 5018.989 | 5018.478 | UUCACUUAUUCCACCGp |
| A46:G65 | 6359.830 | 6359.333 | AUAUAAACCUAAUUACCUCGp |
| U30:G45 | 5000.954 | 5001.082 | UUCACUUAUUCCACCG>p |
| A46:G65 | 6341.815 | 6342.009 | AUAUAAACCUAAUUACCUCG>p |

Csm-40/TtCmr    Csm-40/PfCmr    Csm-40/Cascade

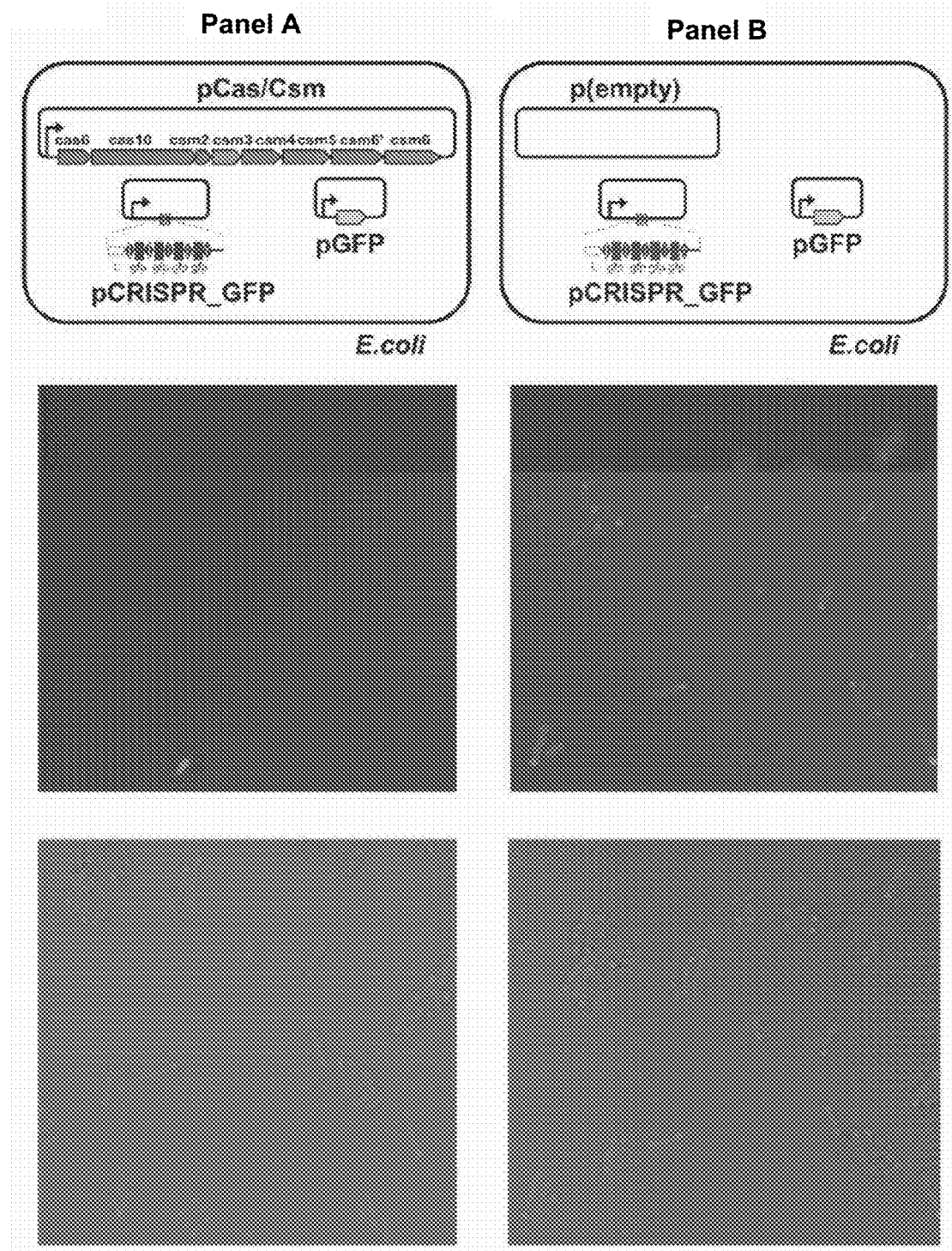

FIG. 15 (continued)
Panel C
Panel D
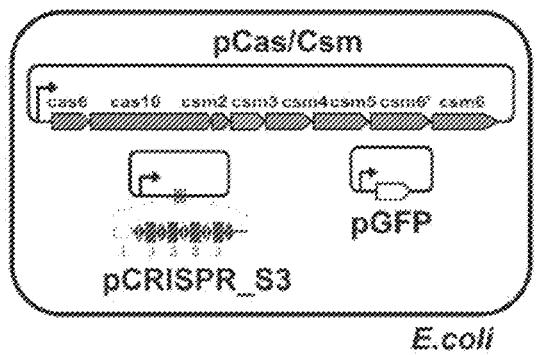
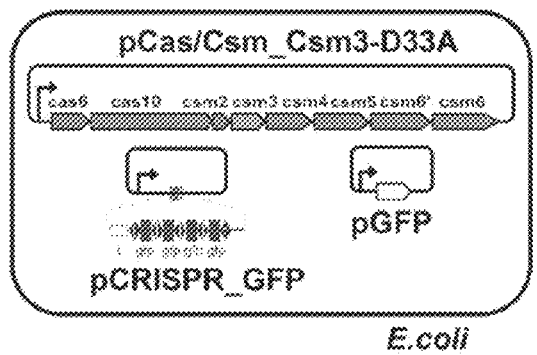
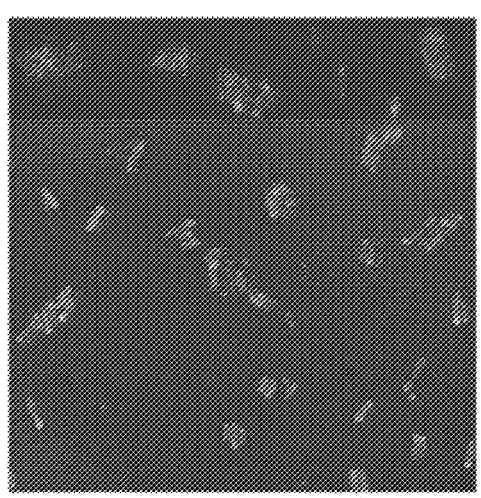
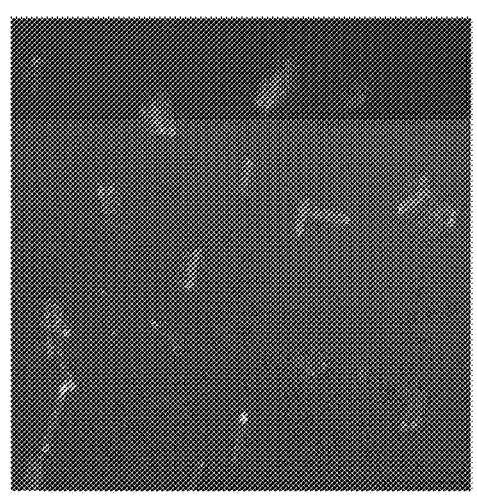
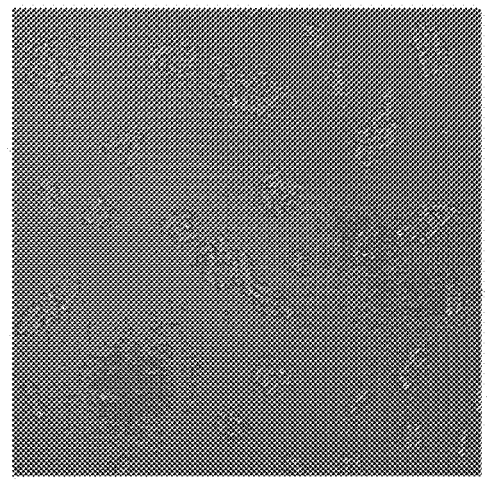
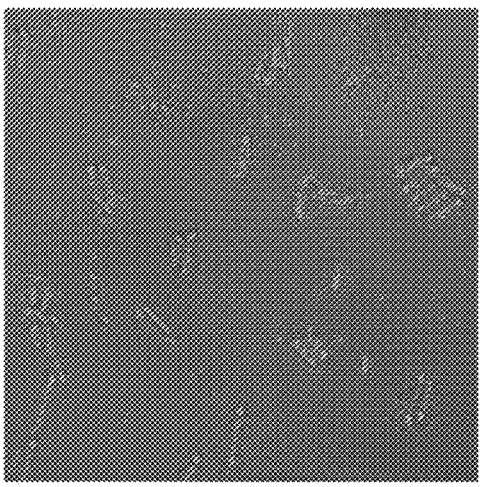

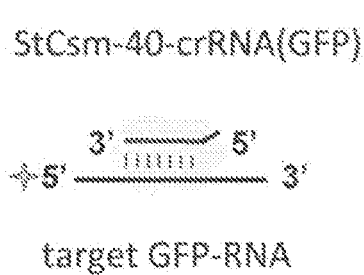
StCsm-40-crRNA(GFP)
target GFP-RNA
RNA binding assay
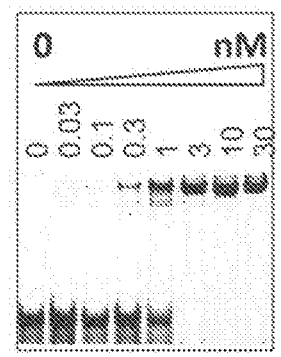
FIG. 16A
RNA cleavage assay
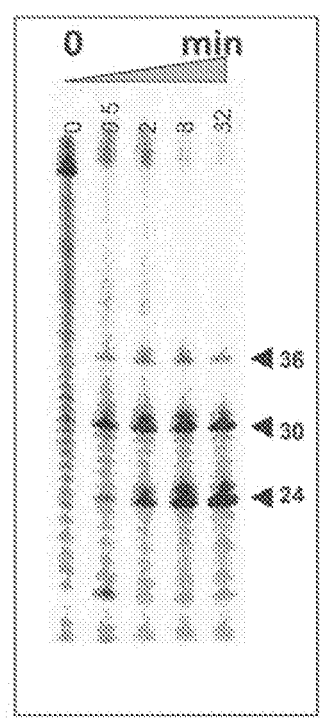
FIG. 16B

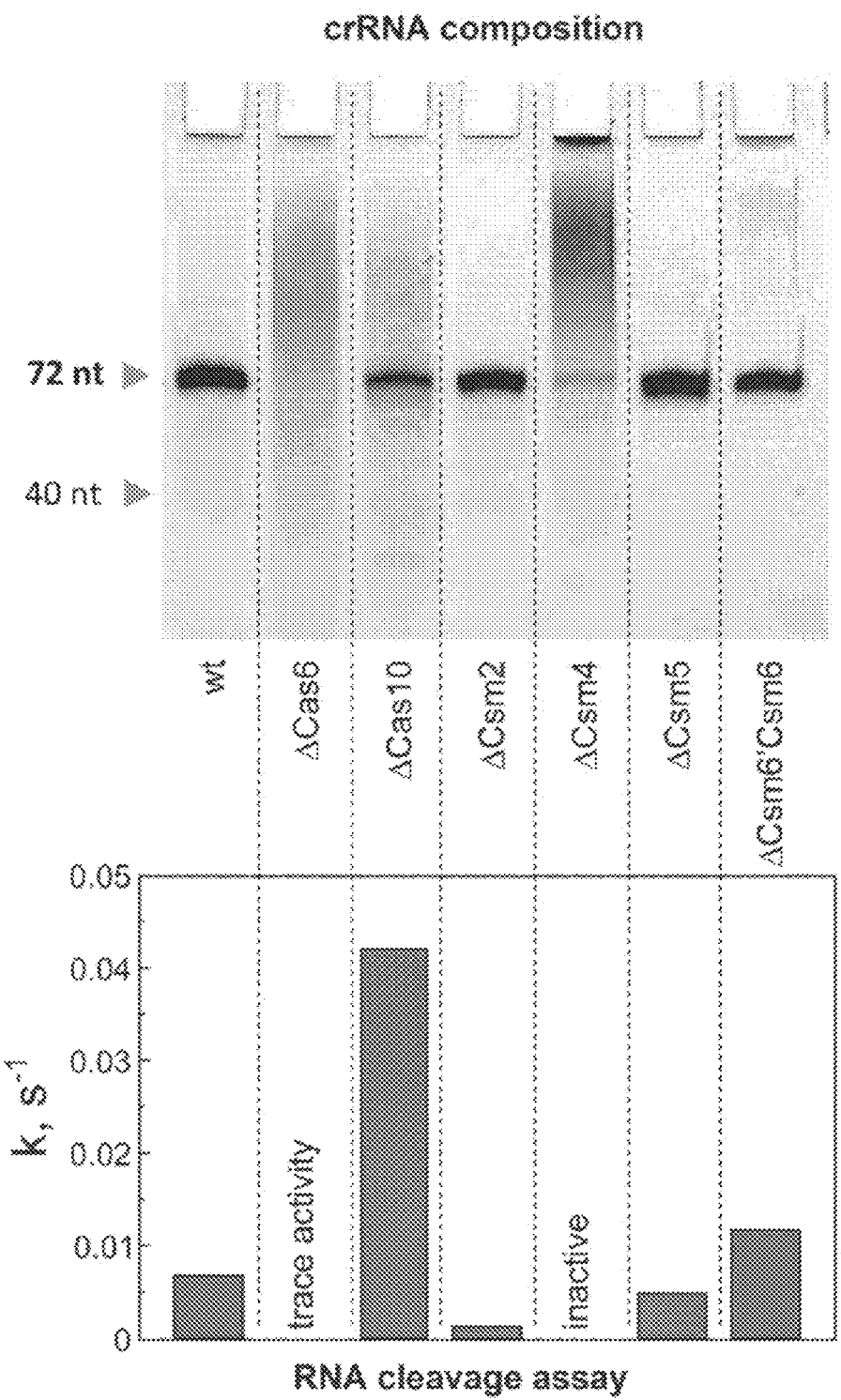

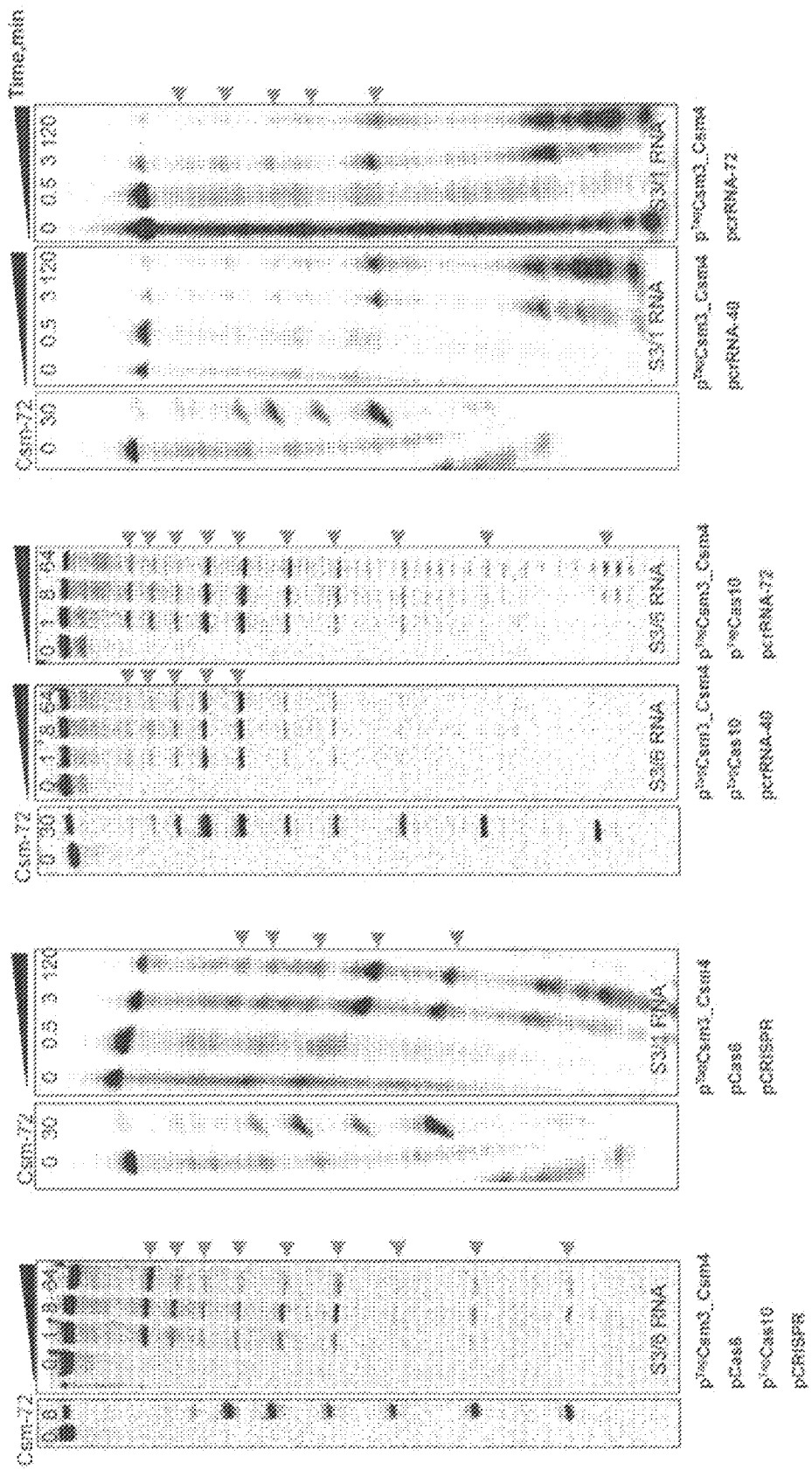

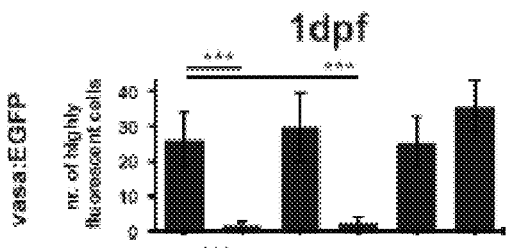
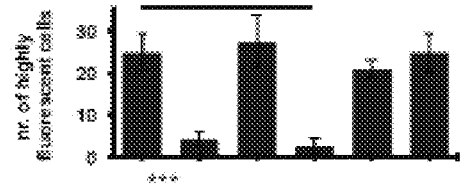
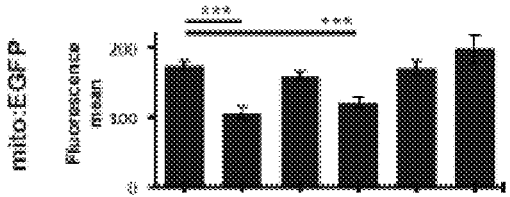
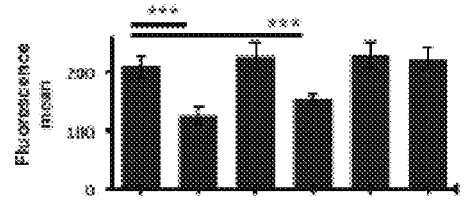
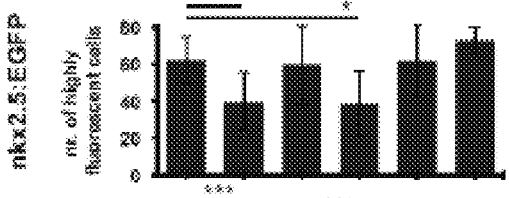
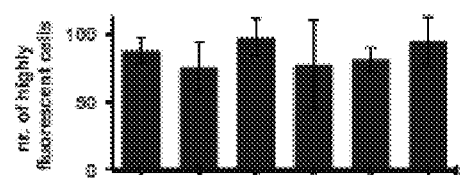
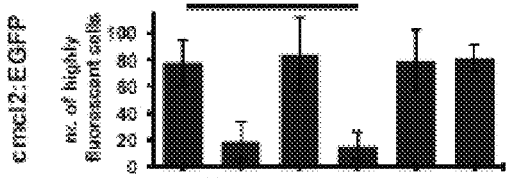
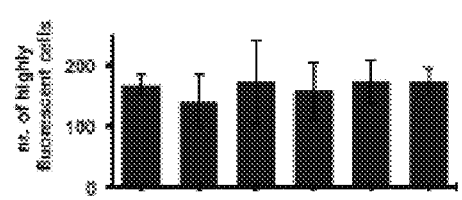
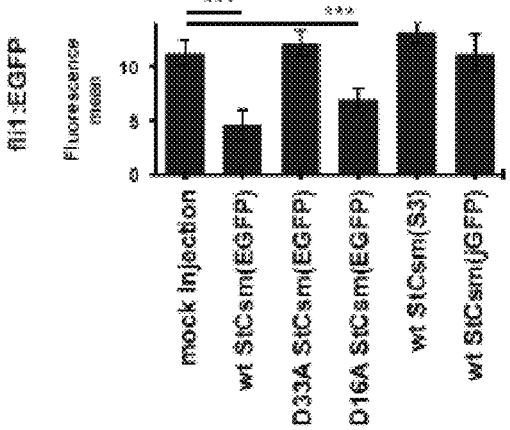
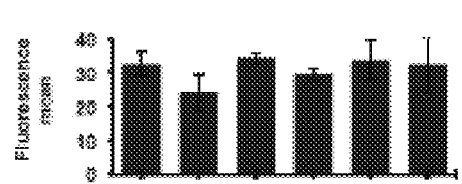
FIG. 24A
FIG. 24B
FIG. 24C
FIG. 24D
FIG. 24E

SEQUENCE LISTING

<160> NUMBER OF SEQ ID NOS: 3

<210> SEQ ID NO 1
<211> LENGTH: 40
<212> TYPE: RNA
<213> ORGANISM: Artificial Sequence
<220> FEATURE:
<223> OTHER INFORMATION: Crisper RNA sequence against enhanced green
      fluorescent protein expressed in trangenic zebrafish

<400> SEQUENCE: 1
acggaaacgu agccuucggg cauggcggac uugaagaagu                40

<210> SEQ ID NO 2
<211> LENGTH: 40
<212> TYPE: RNA
<213> ORGANISM: Artificial Sequence
<220> FEATURE:
<223> OTHER INFORMATION: Crisper RNA sequence against jellyfish green
      fluorescent protein

<400> SEQUENCE: 2
acggaaacau aaccuucggg cauggcacuc uugaaaaagu                40

<210> SEQ ID NO 3
<211> LENGTH: 133
<212> TYPE: RNA
<213> ORGANISM: Artificial Sequence
<220> FEATURE:
<223> OTHER INFORMATION: synthesized EGFP transcript

<400> SEQUENCE: 3
gggaccccga ccacaugaag cagcacgacu ucuucaaguc cgccaugccc gaaggcuacg     60
uccaggagcg caccaucuuc uucaaggacg acggcaacua caagacccgc gccgagguga   120
aguucgaggg cga                                                       133

TARGETED RNA KNOCKDOWN AND KNOCKOUT BY TYPE III-A CSM COMPLEXES

This application is a continuation-in-part of U.S. Ser. No. 15/448,818 filed Mar. 3, 2017 and issued Aug. 20, 2019 as U.S. Pat. No. 10,385,336, which is a continuation-in-part of Ser. No. PCT/IB2015/056756 filed Sep. 4, 2015, which claims priority to U.S. Ser. No. 62/046,384 filed Sep. 5, 2014, each of which is expressly incorporated by reference herein in its entirety.

SEQUENCE LISTING

This application contains a Sequence Listing which has been submitted electronically in ASCII format and is hereby incorporated by reference in its entirety. The ASCII copy, created on Sep. 14, 2017, is named 109904_000031_SL.txt and is 53,119 bytes in size.

Immunity against viruses and plasmids provided by CRISPR-Cas systems relies on a ribonucleoprotein effector complex that triggers degradation of invasive nucleic acids (NA). Effector complexes of Types I (Cascade) and II (Cas9-dual RNA) target foreign DNA. Genetic evidence suggests that Type III-A Csm complex targets DNA, whereas biochemical data show that III-B Cmr complex cleaves RNA.

Clustered Regularly Interspaced Short Palindromic Repeats (CRISPR) together with Cas (CRISPR-associated) proteins provide RNA-mediated adaptive immunity against viruses and plasmids in bacteria and archaea (Terns and Terns, 2014). Immunity is acquired through the integration of invader-derived nucleic acid (NA) sequences as 'spacers' into the CRISPR locus of the host. CRISPR arrays are further transcribed and processed into small interfering CRISPR RNAs (crRNAs) that together with Cas proteins assemble into a ribonucleoprotein (RNP) complex which, using crRNA as a guide, locates and degrades the target NA. CRISPR-Cas systems have been categorized into six major Types (I-VI) that differ by the structural organization of RNPs and NA specificity (Makarova et al. 2011b, Shmakov et al. 2015, Abudayyeh et al. 2016).

Types I and II systems provide immunity against invading DNA. In Type I-E systems, crRNAs are incorporated into a multisubunit RNP complex called Cascade (CRISPR-associated complex for antiviral defense) that binds to the matching invasive DNA and triggers degradation by the Cas3 nuclease/helicase (Brouns et al. 2008, Sinkunas et al. 2013, Westra et al. 2012). In Type II systems, CRISPR-mediated immunity solely relies on the Cas9 protein. It binds a dual RNA into the RNP effector complex, which then specifically cuts the matching target DNA, introducing a double strand break (Gasiunas et al. 2012, Jinek et al. 2012). In Type I and II CRISPR-Cas systems, the target site binding and cleavage requires a short nucleotide sequence (protospacer-adjacent motif, or PAM) in the vicinity of the target (Mojica et al. 2009). Target DNA strand separation, necessary for the crRNA binding, is initiated at PAM and propagates in a directional manner through the protospacer sequence to yield the R-loop intermediate, one strand of which is engaged into the heteroduplex with crRNA, while the other strand is displaced into solution (Sternberg et al. 2014, Szczelkun et al. 2014). Thus, despite differences in their architecture, Type I and II RNP complexes share three major features: i) they act on the invasive double-stranded DNA (dsDNA), e.g., viral DNA or plasmids, ii) they require the presence of a PAM sequence in the vicinity of the target site, and iii) they generate an R-loop as a reaction intermediate.

Type III CRISPR-Cas systems were initially believed to target either DNA (Type III-A) or RNA (Type III-B) (Makarova et al., 2011b). In the III-B systems Cas RAMP proteins (Cmr) and crRNA assemble into a multisubunit RNP complex. Using crRNA as a guide, this complex in vitro binds single-stranded RNA (ssRNA) in a PAM-independent manner and triggers the degradation of target RNA (Hale et al., 2009; Staals et al., 2013; Zhang et al., 2012). The Cmr effector complex is comprised of six Cmr proteins (Cmr1, Cas10, Cmr3-6) that are important for target RNA cleavage; however roles of the individual Cmr proteins and the ribonuclease (RNase) component have yet to be identified. Cmr1, Cmr3, Cmr4 and Cmr6 are predicted RNA-binding proteins that share a ferredoxin-like fold and RNA-recognition motif (RRM) identified in RNA-binding proteins (Terns and Terns, 2014).

The cas genes encoding the RNA-targeting Type III-B (Cmr) and DNA-targeting Type III-A (Csm) effector complexes share a partial synergy (Makarova et al., 2011a). In *Staphylococcus epidermidis* the Csm complex (SeCsm) is comprised of Cas10, Csm2, Csm3, Csm4, and Csm5 proteins, however the function of individual Csm proteins is unknown. The evidence that Type III-A systems target DNA remains indirect and relies on the experimental observation that Type III-A RNP complex from *Staphylococcus epidermidis* (SeCsm) limits plasmid conjugation and transformation in vivo, but the DNA degradation has not been demonstrated directly (Marraffini and Sontheimer, 2008, 2010). The Csm complex from the archaeon *Sulfolobus solfataricus* (SsCsm) binds dsDNA, however, it shows no crRNA-dependent nuclease activity in vitro (Rouillon et al., 2013). Thus, while the RNA cleavage activity of the Cmr complex has been characterized in vitro, the DNA degradation activity of the Type III-A Csm complex has yet to be demonstrated. The Csm complex so far remains the only CRISPR-Cas effector complex, for which the function is not yet reconstituted in vitro. The inventors established the composition and mechanism of the Csm complex for Type III-A system *Streptococcus thermophilus* (St) and demonstrated its RNA cleavage activity both in vitro and in the cell.

Csm proteins and bound crRNA form multisubunit protein-RNA complexes that exhibit two-filament structures characteristic for class 1 CRISPR-Cas complexes (Rouillon et al. 2013). Initial genetic data suggested that the Csm complexes act as RNA-guided DNA endonucleases (Marraffini et al. 2008). Subsequent in vitro studies, however, indicated that the Csm complexes had RNA-guided, RNA-directed endoribonuclease activities cleaving substrate RNAs at multiple, regularly spaced sites Tamulaitis et al. 2014, Staals et al. 2014. The apparent inconsistency between in vivo and in vitro data was resolved by the demonstration that the Csm complexes have transcription dependent DNase activity (Goldberg et al. 2014).

Csm complexes find their targets by hybridization of the guide crRNA with the nascent RNA from transcription (Kazlauskiene et al. 2016). They carry out co-transcriptional DNA and RNA cleavage during the expression phase of bacterial immunity, thus cleaving DNA and eliminating RNA of the invader (Kazlauskiene et al. 2016, Samai et al. 2015). The active sites responsible for the DNase and RNase activities are distinct and located in different subunits of the protein complex. Cas10, a histidine-aspartate nuclease (HD nuclease) and one of the subunits present in only a single copy in the complex, harbors the DNase activity (Kazlauskiene et al. 2016, Jung et al. 2015). Csm3 subunits, present in multiple copies and forming a crRNA binding filament structure, harbor the RNase activities of the Csm complex (Tamulaitis et al. 2014). Consistent with this assignment, the Cas10 D16A and Csm3 D33A mutations (*Streptococcus thermophilus* numbering) specifically abolish ssDNase and Rnase activities of the complex, respectively (Tamulaitis et al. 2014, Kazlauskiene et al. 2016).

Csm complexes can so far only be assembled in bacterial cells. In the natural hosts, pre-crRNAs are expressed from CRISPR region and then processed by cleavage in positions −8 and −9 of the repeat region (numbering with respect to the spacer region) and optional trimming on the 3'-side of the repeat, in steps of six nucleotides as determined by Csm3 as a ruler protein and ribonuclease (Hatoum-Aslan et al. 2011, Hatoum-Aslan et al. 2013). The crRNA maturation and the loading on Csm complexes also occur in heterologous hosts carrying the Cas/Csm operon and associated CRISPR region (Tamulaitis et al. 2014).

Chronic knock-out or abolished gene expression, and acute knockdown or reduced gene expression, often lead to drastically different phenotypes in ways that are only partly explained by technical limitations (Kok et al. 2015, Rossi et al. 2015). CRISPR-Cas9 technology has greatly expanded the possibilities for gene knockout studies. Knockdown technology for animals that are largely refractory to the use of RNA interference (RNAi) has not progressed at the same rate.

Whether Cas9 nucleases could also be used for knockdown was evaluated. The effector nucleases characterized to date contain a variety of RNA directed endoribonucleases, including the class2 (single subunit) effectors Cas13a (C2c2, type VI-A) (Abudayyeh et al. 2016, Shmakov et al. 2016, East-Seletsky at al. 2016) and Cas13b (type VI-B), and the class1 (multiple subunits) effectors of the Csm (type III-A) (Staals et al. 2014, Tamulaitis et al. 2014) and Cmr (type III-B) (Hale et al. 2009, Zhang et al. 2012). The inventors focused on type III-A Csm complexes for targeted RNA knockdown in a vertebrate, specifically zebrafish and determined a CRISPR-mediated RNA knockdown in animals.

SUMMARY

Nucleic acid (NA) specificity and mechanism of CRISPR-interference for the *Streptococcus thermophilus* Csm (III-A) complex (StCsm) is disclosed. A Type III-A CRISPR-Cas (StCsm) complex of *Streptococcus thermophilus* comprising crRNA, Csm4, and Csm3 and use for cleavage of RNA bearing a nucleotide sequence complementary to the crRNA, in vitro or in vivo. When expressed in *Escherichia coli*, two complexes of different stoichiometry co-purified with 40- and 72-nt crRNA species, respectively. Both complexes targeted RNA and generated multiple cuts at 6 nucleotide (nt) intervals. The Csm3 protein, present in multiple copies in both Csm complexes, acts as endoribonuclease. In the heterologous *E. coli* host StCsm restricts MS2 RNA phage in Csm3 nuclease-dependent manner. Methods for site-specific cleavage/shredding of a target RNA molecule using an RNA-guided RNA endonuclease comprising a minimal complex of crRNA, Csm4, and Csm3, and methods of RNA knock-down and RNA knock-out are disclosed.

The inventors determined that *Streptococcus thermophilus* Type III-A Csm (StCsm) complex targets RNA, and that multiple cuts are introduced in the target RNA at 6 nt intervals. Target RNA that is complimentary to crRNA is cleaved at multiple sites at regular 6 nt intervals, also termed shredding. RNA cleavage is protospacer-adjacent motif (PAM) independent. A Csm3 subunit is responsible for endoribonuclease activity of the complex. Because multiple copies of Csm3 subunits are present in the Csm complex, cleavage occurs at multiple sites. By systematic deletion of the genes encoding individual subunits, the minimal Csm complex composition required for target RNA cleavage was established.

The StCsm complex offers a novel programmable tool for RNA-degradation or modification, e.g., in methods similar to RNA Interference (RNAi) methods, and using RNAi methods known in the art. However, different from RNA interference based methods that rely on the RNAi binding to the target RNA resulting in the gene product knock-down, RNA-targeting by the Csm complex allows knock-out of the gene product because the target RNA is cleaved at multiple sites. If an RNA-cleavage deficient Csm complex (Csm3D33A) is used, knock-downs instead of knockouts can be achieved, which provides additional flexibility.

Methods of cleaving RNA in an animal to knockdown or knockout gene expression are additionally disclosed, using compositions comprising a nucleic acid encoding at least one protein subunit of a Csm complex, the Csm complex capable of cleaving RNA in a vertebrate. The method administers to the vertebrate a crRNA and a Csm complex having ribonuclease activity. Using transgenic zebrafish lines that express enhanced green fluorescent protein (EGFP), the composition resulted in decreased detected EGFP due to RNA knockdown. The inventors thus have disclosed the first use of the CRISPR-Cas Type IIIA RNA knockdown system in vertebrates using a zebrafish model.

The method also provides an improved alternative to traditional RNA interference (RNAi). While RNAi is a powerful experimental tool, it does not work in all organisms. In zebrafish that are poorly amenable to RNAi, morpholino polynucleotide analogues have traditionally been used as alternative means to suppress either pre-mRNA splicing or translation initiation.

Csm Type III-A CRISPR-Cas complex was able to knock down EGFP expressed from various promoters. The best efficacies were obtained in the vasa:EGFP line that have only maternal EGFP transcript. Effects were also seen in fish lines that express EGFP zygotically. Knockdown was statistically significant in cmcl2:EGFP and fli1:EGFP zebrafish lines at 1 day post fertilization (dpf), but reduced to background levels at 2 dpf. The nkx2.5:EGFP fish line was least susceptible to Csm mediated EGFP knockdown.

A ternary StCsm complex of Cas10, Csm2, Csm3, Csm4, and Csm5 proteins and a crRNA complementary to the target RNA transcript was employed. However, other complexes containing Cas10, such as Csm complexes from other organisms or related Cmr complexes (Tamulaitis et al. 2017), should be capable to degrade RNA and therefore to knockdown the expression of the target RNA. Therefore the invention is not limited to the complex used in the exemplary descriptions and other Cas10-containing complexes may be used similarly to Csm complex described here.

BRIEF DESCRIPTION OF THE FIGURES

The patent or application file contains at least one drawing executed in color. Copies of this patent or patent application publication with color drawing(s) will be provided by the office upon request and payment of the necessary fee.

(FIG. 1A) Schematic organization of the Type III-A CRISPR2-cas locus (see also FIG. 8). Repeats and spacers are indicated by diamonds and rectangles, respectively, T is for the terminal repeat, L is for the leader sequence, and the arrow indicates the promoter. (FIG. 1B) Protospacer PS3 and the 5'-flanking sequence in the *S. thermophilus* phage 01205 genome. (FIG. 1C) Strategy for expression and isolation of the StCsm complex. Four copies of the spacer S3 have been engineered into the pCRISPR_S3 plasmid to increase the yield of the Csm-crRNA complex. (FIG. 1D) Coomassie blue-stained SDS-PAAG of Strep-tagged Csm2 and Csm3 pull-downs. 3N Csm3_StrepN protein, M—protein mass marker. (FIG. 1E) Denaturing PAGE analysis of NA co-purifying with the Csm2_StrepN and Csm3_StrepN complexes. M-synthetic DNA marker. (FIG. 1F) and (FIG. 1G) Characterization of crRNA in the isolated StCsm complexes. Cartoon models illustrate crRNA which co-purify with StCsm-72 and StCsm-40 complexes. Composition of the crRNA was determined using LC ESI MS analysis (see also FIG. 9). IP RP HPLC analysis and ESI MS spectra of IP RP HPLC purified crRNA from StCsm-40 and StCsm-72 are presented. (FIG. 1H) Superimposed averaged dummy atom models obtained from SAXS data of StCsm-40 (light beads) and StCsm-72 (dark beads) (see also FIG. 10). FIG. 1A discloses SEQ ID NO: 106, FIG. 1F discloses SEQ ID NO: 66 and FIG. 1G discloses SEQ ID NO: 67.

(FIG. 2A) Schematic representation of DNA and RNA substrates used for in vitro binding and cleavage assays. NAs were 5'- or 3'-end labeled with 32P (indicated as *). (FIG. 2B) EMSA analysis of DNA or RNA binding by StCsm-40. NS stands for a non-specific RNA. (FIG. 2C) Binding competition assay. 0.5 nM of 32P-labelled S3/1 RNA was mixed with increasing amounts of unlabeled competitor NAs and 0.3 nM StCsm-40, and analyzed by EMSA. (FIG. 2D) StCsm-40 cleavage assay. Gel-purified DNA or RNA were used as substrates in the NA cleavage assay. Triangles with corresponding numbers indicate cleavage product length. M—RNA Decade marker, R-RNase A digest marker, H-alkaline hydrolysis marker. (FIG. 2E) RNA cleavage products mapped on the S3/1 RNA substrate sequence. Triangles and dashed lines indicate cleavage positions. Short vertical lines above the sequence indicate nucleotides complementary to crRNA. crRNA (StCsm-40) sequence (SEQ ID NO: 67) is depicted above the matching substrate fragments (SEQ ID NOS 74 and 76, respectively, in order of appearance).

(FIG. 3A) Schematic representation of the StCsm-72 complex and RNA substrates used in the cleavage assay. RNA substrates were 5'-end labeled with 32P (indicated as *) and gel-purified. (FIG. 3B) StCsm-72 cleavage assay. M—RNA Decade marker. (FIG. 3C) RNA cleavage products mapped on the S3/2, S3/5 and S3/6 RNA substrates sequences (SEQ ID NOS 66, 75, 79 and 80, respectively, in order of appearance).

(FIG. 4A) Schematic representation of the StCsm-40 complex and RNA substrates used in the cleavage assay. RNA substrates were 5'-end labeled with 32P (indicated as *) and gel-purified. (FIG. 4B) StCsm-40 binding affinity assay. (FIG. 4C) StCsm-40 cleavage assay. M—RNA Decade marker. (FIG. 4D) RNA cleavage products mapped on the RNA substrates sequences. FIG. 4D discloses SEQ ID NOS 67, 75, 107 and 84-87, respectively, in order of appearance.

FIGS. 5A-1, A-2, B-F show computational and mutational analysis of Csm3. (FIG. 5A) Alignment of Csm3 and Cmr4 sequence representatives (SEQ ID NOS 108-116, respectively, in order of appearance) from experimentally characterized Type III effector complexes. Identical and similar residues in more than half of sequences are shaded in dark and light correspondingly. StCsm3 positions subjected to site-directed mutations are indicated by triangles above the sequence.

(FIG. 6A) Schematic representation of the assay. The arrow indicates the promoter. (FIG. 6B) Phage plaque analysis. Serial 10-fold dilutions of MS2 were transferred onto lawns of *E. coli* NovaBlue (DE3, F+) strain expressing StCsm-crRNA complex targeting the MS2 genome, or control cells.

(FIGS. 4A-C) ESI MS/MS oligoribonucleotide mapping of crRNA isolated from StCsm-72. (FIG. 9A) Base peak chromatogram of RNase T1 digest. RNase Ti cleaves single-stranded RNA 3' of G residues. Predominant oligoribonucleotide peaks of the crRNA are highlighted. Masses of each oligoribonucleotide are presented in the table. FIG. 9A discloses SEQ ID NOS 121-123, 123, 121 and 122, respectively, in order of appearance. The theoretical and experimental masses are shown for the oligoribonucleotides identified. (FIG. 9B) Base peak chromatogram of RNase A digest. RNase A cleaves single-stranded RNA 3' of C or U residues. (FIG. 9C) ESI MS/MS analysis of the oligoribonucleotide GAGAGGGGp. Tandem MS was used to verify the oligoribonucleotide. The predominant fragment ions are highlighted. (FIG. 9D) ESI MS/MS oligoribonucleotide mapping of crRNA isolated from StCsm-40. Base peak chromatogram of RNase T1 digest. The oligoribonucleotide UUCACUUAUUC (SEQ ID NO: 1) was unique to the 40-nt crRNA. p=3'-phosphate, >p=¬2'3'-cyclic phosphate. FIG. 9D discloses SEQ ID NOS 123, 1, 121, 122, 123, 1, 121, 122, 121 and 122, respectively, in order of appearance.

(FIG. 10A) Scattering profiles shown as a logarithmic plot of scattering intensity I(s) vs momentun transfer $s=4\pi \sin(\theta)/\lambda$, where 2θ is the scattering angle and $\lambda$ is X-ray wavelength. (FIG. 10B) Kratky plot of SAXS data, $l(s)*s^2$ vs s. (FIG. 10C) Guinier plots of SAXS data. In $l(s)$ vs $s^2$ and its linear fit. The truncated first points are shown as open circles. (FIG. 10D) Distance distribution functions of StCsm-40 and StCsm-72 complexes calculated using GNOM (Svergun, 1992). (FIG. 10E) The electron density of the TtCmr (dark beads), PfCmr (dark beads), and E. coli Cascade complexes (dark beads) aligned with the StCsm-40 (light beads) model.

(FIG. 11A) Schematic representation of S3/1 and S3/2 RNA substrates used in binding and cleavage assays. Nucleic acids were 5'-end labeled with 32P (indicated as *). (FIG. 11B) Electrophoretic mobility shift binding assay. The binding reactions contained 32P-labeled RNA (0.5 nM) and the StCsm-72 or StCsm-40 at concentrations indicated by each lane. Samples were analyzed by PAGE under non-denaturing conditions. NS shows the non-specific RNA control. (FIG. 11C) Cleavage assay. Cleavage reactions were performed at 37° C. for Csm-72 and 25° C. for Csm-40 for indicated time intervals in the Reaction buffer supplemented with 10 mM Mg-acetate, 20 nM RNA substrate and 125 nM StCsm-72 or 62.5 nM StCsm-40. Samples were analyzed by denaturing PAGE, followed by phosphorimaging. In control experiments RNA substrate was incubated for 64 min at 37° C. or 36 min at 25° C. in the Reaction buffer alone ("lane 0") or the storage buffer was added instead of the Csm complex ("lane B"). Triangles denote the reaction products (the sizes of cleavage fragments are given near triangles). M—RNA Decade marker, R—oligoribonucleotide fragments generated from RNase A digestion of RNA, H—alkaline hydrolysis of RNA. (FIG. 11D) RNA cleavage products mapped on the RNA substrates sequence (SEQ ID NOS 67, 66 and 74-76, respectively, in order of appearance). Triangles and dashed lines indicate cleavage positions. Short vertical lines above the sequence indicate nucleotides complementary to crRNA. 40-nt and 72-nt crRNAs containing spacer S3 sequences are depicted above the matching substrate fragments. NS stands for non-specific RNA. (FIG. 11E) Metal ion (Me2+) dependency of the RNA cleavage by the StCsm complex. S3/1 RNA substrate was pre-incubated with StCsm-40 and reaction products were analyzed in denaturing polyacrylamide gels. Cleavage reactions were conducted at 25° C. for 3 min in Reaction buffer containing 20 nM 32P-5'-labelled gel purified S3/1 RNA substrate, 62.5 nM Csm-40 and 1 mM EDTA, 10 mM Mg-acetate, 10 mM MnC12, 1 mM Ca-acetate, 0.1 mM ZnSO4, 0.1 mM NiC12, or 1 mM CuSO4. Triangles and numbers denote the reaction products and their sizes, respectively. M—RNA Decade marker. (FIG. 11F) S3/1 RNA cleavage pattern of the heterogeneous Csm-complex. To express and to purify heterogeneous Csm complex the wt CRISPR2 region containing 13 spacers of S. thermophilus DGCC8004 was cloned into the pACYC-Duet-1 vector. The heterogeneous StCsm-72 complex was expressed and purified following the same procedure described for the homogenous Csm complex targeting the S3 protospacer. Specific S3/1 RNA substrate and non-specific NS RNA were pre-incubated with heterogeneous StCsm-72. Cleavage reactions were performed at 37° C. for indicated time intervals in the Reaction buffer supplemented with 10 mM Mg-acetate, 20 nM RNA substrate and 350 nM heterogeneous StCsm-72. Samples were analyzed by denaturing PAGE, followed by phosphorimaging. Triangles and numbers denote the reaction products and their sizes, respectively. M—RNA Decade marker.

(FIG. 12A) Schematic representation (+Tc) and (−Tc) RNA substrates used in the cleavage assay. Arrows indicate TcR gene promoter and direction of transcription. RNA substrates were 5'-end labeled with 32P (indicated as *) and gel purified. The Tc (tetracycline resistance protein) gene transcript or RNA corresponding to the non-coding strand of Tc in the pBR322 plasmid (nt 851-886) were used as RNA targets. To reprogram the StCsm complex a synthetic CRISPR locus containing five 36-nt length repeats interspaced by four identical 36-nt spacers complementary to the sense or antisense DNA strands of the Tc gene were engineered into the pACYC-Duet-1 plasmids which were independently co-expressed in E. coli together with plasmids pCsm/Cas and pCsmX-Tag. StCsm-40 and StCsm-72 complexes reprogrammed for the sense (+Tc) RNA or anti-sense (−Tc) RNA fragments were isolated similarly to StCsm bearing spacer S3. (FIG. 12B) Cleavage reactions were performed at 37° C. for 120 min in the Reaction buffer supplemented with 10 mM Mg-acetate, 20 nM gel purified RNA substrate and 40-120 nM of Csm complex. Samples were analyzed by denaturing PAGE, followed by phosphorimaging. Triangles with corresponding numbers indicate cleavage product length. M—RNA Decade marker. (FIG. 12C) RNA cleavage products (SEQ ID NOS 89, 88, 90, 92, 91 and 93, respectively, in order of appearance) mapped on the (+Tc) and (−Tc) RNA substrates sequences. The sequences of reprogrammed 40-nt and 72-nt length crRNAs are depicted above the substrates. Short vertical lines above the sequence indicate nucleotides complementary to crRNA. Triangles and dashed lines indicate cleavage positions. Translated fragment which corresponds to the tetracycline resistance protein gene RNA transcript is indicated under (+Tc) RNA substrate.

(FIG. 13A) Schematic representation of the StCsm-40 complex and RNA substrates used in the cleavage assay. RNA substrates were 5'-end labeled with 32P (indicated as *) and gel purified. (FIG. 13B) Cleavage reactions were performed at 25° C. for indicated time intervals in the Reaction buffer supplemented with 10 mM Mg-acetate, 20 nM RNA substrate and 62.5 nM StCsm-40. Samples were analyzed by denaturing PAGE, followed by phosphorimaging. Triangles with corresponding numbers indicate cleavage product length. M—RNA Decade marker. (FIG. 13C) RNA cleavage products (SEQ ID NOS 67, 66 and 124-130, respectively, in order of appearance) mapped on RNA substrates sequences. Short vertical lines above the sequence indicate nucleotides complementary to crRNA. Triangles and dashed lines indicate cleavage positions. The sequences of both 40-nt and 72-nt length crRNAs containing spacer S3 present in StCsm-40 preparation are depicted above the substrates.

(FIGS. 14A-C) A structural model of StCsm3 in different representations. (FIG. 14A) Cartoon representation with the core RRM region shown in dark and the "lid" domain shown in light. Active site residue D33 is indicated. (FIG. 14B) Molecular surface of the Csm3 model colored according to sequence conservation (dark-conserved, light-variable). (FIG. 14C) Molecular surface of the Csm3 model colored according to electrostatic potential (dark-positive, light-negative). (FIG. 14D) Clustering of 604 Csm3 and Cmr4 sequence homologs with CLANS. Representatives of Csm3 and Cmr4 families from experimentally characterized (Hale et al. 2009; Hatoum-Aslan et al., 2013; Hrle et al. 2013, Millen et al. 2012, Rouillon et al. 2013, Staals et al. 2013; Zhang et al., 2012) Type III CRISPR-Cas systems are labeled. Each dot represents a sequence, connecting lines represent the similarity between sequences. Thicker lines and shorter distances indicate higher sequence similarity. Only connections corresponding to P-values of 1e-12 or better are shown.

FIG. 15 shows StCsm-triggered GFP transcript degradation in vivo. E. coli BL21 (DE3) was transformed with three compatible plasmids (see schematic representation in panels A-D): (i) pCRISPR_GFP plasmid bearing the synthetic CRISPR array of five repeats interspaced by four 36-nt spacers targeting the jellyfish GFP (jGFP) transcript; (ii) pCsm/Cas plasmid for the expression of Cas/Csm proteins; (iii) pGFP plasmid for jGFP expression. The StCsm and jGFP transcript expression was induced in E. coli and the jGFP transcript degradation was monitored by inspecting GFP fluorescence in the cells. The cells were imaged by contrast (see bottom images in panels A-D) and fluorescence microscopy (see top images in panels A-D).

FIGS. 16A-B show in vitro cleavage activity of the StCsm targeted to the GFP transcript. Schematic representation of StCsm bound to the target RNA used for in vitro binding and cleavage assays is presented above the gels. RNA was 5'-end labeled with $^{33}$P as indicated with asterisk. (FIG. 16A) Gel shift assay of RNA binding by StCsm-40. The binding reactions contained the $^{33}$P-labeled GFP RNA (0.5 nM) and StCsm-40 at concentrations indicated by each lane. Samples were analyzed by PAGE under non-denaturating conditions. (FIG. 16B) StCsm-40 cleavage assay. Cleavage reactions were performed at 25° C. for indicated time intervals in the Reaction buffer supplemented with 10 mM Mg-acetate, 8 nM GFP RNA substrate and 160 nM StCsm-40. Samples were analyzed by denaturing PAGE, followed by phosphorimaging. Triangles with corresponding numbers indicate cleavage product length.

(FIG. 17A) Protein composition of the purified StCsm-40 deletion mutant variants as revealed by SDS-PAAGE. In all cases the protein that corresponds to the disrupted cas gene is lacking. In case of ΔCsm4 mutant, the obtained Csm-complex also lacks Cas10, in addition to Csm4. In cells that are deprived of csm3 gene, no complex is pull-downed by the Csm2-Tag subunit. (FIG. 17B) crRNAs co-purified with StCsm-complex deletion mutant variants were extracted using phenol:chloroform:isoamylalcohol and precipitated with isopropanol. Isolated nucleic acids were separated on a denaturing 15% PAAG and visualised by means of SybrGold staining. In cases of ΔCas6 and ΔCsm4, the purified nucleic acid samples contained a ribonucleic acid molecules of variable size. In almost all cases analysed (ΔCas6, ΔCas10, ΔCsm4, and ΔCsm5; with the exception of ΔCsm6'ΔCsm6) the crRNA is not fully matured 40 nt species. However, a band corresponding to 72 nt crRNA was visible in cases of ΔCas10, ΔCsm4, and ΔCsm5 mutants. (FIG. 17C) RNA binding affinity of StCsm complex deletion mutant variants was analyzed using electrophoretic mobility shift assay. Two $^{33}$P-5'-labeled 68 nt RNA substrates were used for this experiment: specific S3/1 (containing a sequence fully complementary to the 36 nt crRNA encoded by spacer S3; data corresponding to it is depicted in light bars) and the non-complimentary NS RNA (dark bars). Different amounts of the StCsm (0.01-300 nM) were mixed with 0.5 nM of the RNA substrate in the binding buffer containing 1 mM EDTA. Samples were analysed using native 8% PAAG. The dissociation constants ($K_d$) for RNA binding by StCsm-40 deletion mutants were evaluated assuming the complex concentration at which half of the substrate is bound as a rough estimate of $K_d$ value. Notably, while target RNA binding is significantly decreased in the case of ΔCas6 and ΔCsm4 variants, deletion of Csm5 fully abolishes target RNA binding. (FIG. 17D) RNA cleavage assays for StCsm-40 variants were conducted using the radioactively labelled 68 nt specific S3/1 RNA substrate. Reactions, containing 4 nM S3/1 RNA substrate and 160 nM (or 320 nM) of StCsm in the reaction buffer (33 mM Tris-acetate (pH 7.9 at 25° C.), 66 mM K-acetate, 0.1 mg/ml BSA, and 1 mM Mg-acetate), were initiated by addition of $Mg^{2+}$ ions and performed at 15° C. Consequent reaction products were separated on a denaturing 20% PAGE and depicted by autoradiography. The RNA cleavage rate constants were determined by fitting single exponentials to the substrate depletion data. The obtained constants for each of StCsm variant are depicted in the graph. The cleavage activity of both ΔCas10 and ΔCsm6'ΔCsm6 are similar to wt. In all other cases the hydrolysis rate is significantly diminished. Deletion of Csm4 completely abolishes StCsm clevage activity completely.

FIGS. 18A-D show protein composition and in vitro cleavage activity of deletion mutants of StCsm-72 complex. In order to obtain StCsm-72 deletion mutants, pCas/Csm deletion variants were co-expressed with pCRISPR_S3 and pCsm3-Tag plasmids in *Escherichia coli* BL21(DE3). StCsm-72 complexes were isolated by affinity and size exclusion chromatography. (FIG. 18A) Protein composition of the purified StCsm-72 deletion mutants as revealed by SDS-PAAGE. In all cases the protein that corresponds to the disrupted cas gene is lacking. ΔCsm4 variant, in addition to Csm4, lacks Cas10 subunit. (FIG. 18B) crRNAs that co-purify with StCsm-72 were isolated (as described in FIGS. 17A-D), separated on a denaturing 15% PAAG, and visualised by SybrGold staining. In the case of ΔCas6 and ΔCsm4 variants, the purified nucleic acid co-purified with the Csm-complex deletion variant contained a ribonucleic acid molecules of variable size. In all other cases analysed (ΔCas10, ΔCsm2, ΔCsm4, and ΔCsm6'ΔCsm6) a clear band, corresponding to 72 nt crRNA is present. (FIG. 18C) Electrophoretic mobility shift assay was employed to evaluate binding affinities of StCsm complexes to the complimentary target (light bars) and non-targeting (dark bars) RNAs. The experiment was performed as described for StCsm-40 complexes (see FIGS. 17A-D). Deletion of Csm5 significantly decreased specific binding. (FIG. 18D) RNA cleavage assays for StCsm-72 variants were carried out similarly as described for StCsm-40 (see FIG. 17 legend). The graph depicts rate constants for the target RNA cleavage. The ΔCas6 or ΔCsm4 variants of StCsm-72 display almost no activity. In all other cases cleavage products, that are characteristic to StCsm-72, are visible on the gel.

FIGS. 19A-D shows RNA cleavage activity of the minimal StCsm complex variants. According to analysis of the StCsm deletion mutants, Csm3 and Csm4 are absolutely required for complex formation. To co-express the Csm3 and Csm4 proteins csm3 and csm4 genes were cloned into pCDFDuet-1 vector and StrepII-Tag sequence was fused to the N-terminal part encoding csm3 gene to obtain $p^{Tag}Csm3\_Csm4$. $p^{Tag}Cas10$ plasmid was engineered by cloning the cas10 gene into pETDuet-1 vector. pCas6 plasmid was engineered by cloning the cas6 gene into pCOLA-Duet-1 vector. The expression of Cas6 protein together with pCRISPR (encoding the S3 CRISPR array) would generate 72 nt crRNAs. Alternatively, plasmids from which 40 nt or 72 nt crRNAs could be obtained by in vitro transcription were constructed on the basis of pACYCDuet-1 vector (with cloned BBa J23119 promoter) and named pcrRNA-40 and pcrRNA-72, respectively. $p^{Tag}Csm3\_Csm4$ was co-expressed with pcrRNA-40, pcrRNA-72, or both pCas6 and pCRISPR plasmids in *Escherichia coli* BL21(DE3). Subsequent Strep-chelating affinity chromatography yielded ribonucleoprotein (RNP) complexes, containing Csm3 and Csm4 proteins. The RNA cleavage activity of these RNP complexes was tested on the complimentary 68 nt S3/4 RNA target or S3/6 RNA target (containing a sequence fully complementary to the 36 nt crRNA encoded by spacer S3). Reactions, containing 4 nM RNA substrate and ~15 ng/µl of the RNP complex in the reaction buffer (33 mM Tris-acetate (pH 7.9 at 25° C.), 66 mM K-acetate, 0.1 mg/ml BSA, and 10 mM Mg-acetate), were initiated by addition of the purified RNP complex and incubated at 37° C. for the time indicated on the top of the lanes (in minutes). Reaction products corresponding to the wt StCsm-72 complex cleavage are indicated by grey triangles. The same RNA cleavage pattern, characteristic to the wt StCsm-72, shown in (FIG. 19A) minimised RNP complexes, containing Csm3, Csm4, Cas10, and crRNA, generated by Cas6, (FIG. 19B) minimal RNP complexes containing Csm3, Csm4, crRNA and Cas6, (FIG. 19C) minimised RNP complexes, containing Csm3, Csm4, Cas10, and crRNA (derived from pcrRNA-40 or pcrRNA-72 plasmids), and (FIG. 19D) minimal RNP complexes containing only Csm3 and Csm4 subunits and crRNA.

FIG. 22A Coomassie blue-stained SDS-PAGE of purified StCsm complexes. M, protein mass marker. FIG. 22B denaturing PAGE analysis of crRNA co-purifying with the StCsm complexes. M, synthetic DNA marker. FIG. 22C shows RNA cleavage activity in vitro, and more specifically, the depletion of radioactively labeled target EGFP RNA measured in 1 hour after RNA cleavage reaction initiation.

FIGS. 24A-E illustrates quantification of knockdown efficiency of different StCsm complexes at one and two days post fertilization by FACS analysis: EGFP fluorescence in vasa:EGFP (FIG. 24A), mito:EGFP (FIG. 24B), nkx2.5:EGFP (FIG. 24C), cmcl2:EGFP (FIG. 24D), and fli1:EGFP fish (FIG. 24E) was quantified 1 dpf and 2 dpf by flow cytometry of minced and trypsinized embryos. For vasa:EGFP, nkx2.5:EGFP cmcl2:EGFP embryos, the number of highly fluorescent cells (at least 50 times background fluorescence) was counted. For mito:EGFP and fli1:EGFP, the fluorescence mean was determined. Results are from three independent experiments, error bars represent one standard deviation (*P<0.05 as compared with respective controls; ***P<0.001 as compared with respective controls).

FIG. 25 discloses SEQ ID NOS 135, 136, 135, 136, 135, 136, 137, 136, 138, 67, 136 and 74, respectively, in order of appearance.

FIG. 26A is a depiction of the StCsm complex cleavage of 5' radioactively labeled target RNA. FIG. 26B provides polyacrylamide gel electrophoresis results of the in vitro RNA cleavage assay. The in vitro synthesized radioactively 5'-labeled segment of EGFP transcript was used as a substrate in RNA cleavage assay. Reactions were initiated by addition of Mg2+ and products were analyzed in denaturing polyacrylamide gel.

FIG. 27A illustrates the general scheme of StCsm complex DNase activation. Binary StCsm complex binds complementary target RNA and forms ternary StCsm complex. The binding of complementary target RNA activates Cas10 (pink circle) and ssDNA is degraded. FIG. 27B depicts the ssDNA cleavage by the binary and ternary StCsm complexes. Reactions were initiated by addition of Mn2+ and products were analyzed on agarose gels.

FIG. 40A depicts crRNAs and target RNA sequences. The in vitro synthesized 133 nt length radioactively 5'-labeled segment of EGFP transcript was used as a substrate in RNA binding and cleavage assay. FIG. 40B provides polyacrylamide gel electrophoresis results of the in vitro RNA binding assay. FIG. 40C provides polyacrylamide gel electrophoresis results of the in vitro RNA cleavage assay performed at 15° C. Reactions were initiated by addition of $Mg^{2+}$ and products were analyzed in denaturing polyacrylamide gel.

In one embodiment, a method for the site-specific modification/shredding (i.e., cleaving) of a target RNA molecule is provided by contacting, under suitable conditions, a target RNA molecule and an RNA-guided RNA endonuclease complex comprising at least one RNA sequence and at least two different Csm protein subunits, to result in the target RNA molecule being modified/shredded in a region that is determined by the complimentary binding of the RNA sequence to the target RNA molecule. The method includes incubating under suitable conditions a composition that includes a target RNA molecule with a StCsm complex comprising a polyribonucleotide (crRNA) comprising a 5' handle, a 3' handle, and a spacer that is complementary, or substantially complementary, to a portion of the target RNA. In one embodiment, the crRNA lacks the 3' handle. In one embodiment, the minimal StCsm complex required for target RNA cleavage comprises Csm4 and $(Csm3)_x$ (X=1-10) proteins and 40 or 72 nt crRNA. In embodiments, crRNA is produced by in vitro transcription or chemical synthesis. In embodiments, suitable conditions means conditions in vitro or in vivo where reaction might occur.

In embodiments, the disclosed engineered StCsm complex is used as an RNA Interference tool, to knock-out or knock-down a target RNA, such as mRNA. In one embodiment, Csm3 is modified to include a mutation. One such mutation is D33A, which inactivates the endonuclease activity of Csm3. In various embodiments, the Csm3 D33A may be used to knock-down mRNA expression. Target RNA knock-out results due to the RNA cleavage by the Csm3 protein in the Csm-complex. D33A mutation impairs target RNA cleavage by retains RNA binding ability of the Csm-complex that enables knock-down of the gene product.

StCsm complex might be isolated from a genetically modified microbe (for example *Escherichia coli* or *Streptoccocus thermophilus*). In the genetically modified microbe, components of the complex might be encoded on the one, two or three separate plasmids containing host promoters of the genetically modified microbe or promoters from a native host genome.

In one embodiment, a composition is provided, and comprising an engineered StCsm complex comprising crRNA, Csm4, and Csm3. The crRNA of the engineered complex is programmed to guide the StCsm complex to a selected site in a target RNA molecule, wherein the StCsm complex is capable of shredding the target RNA molecule under suitable conditions.

Type III-A CRISPR-Cas Loci in S. thermophilus

Figure 1A:
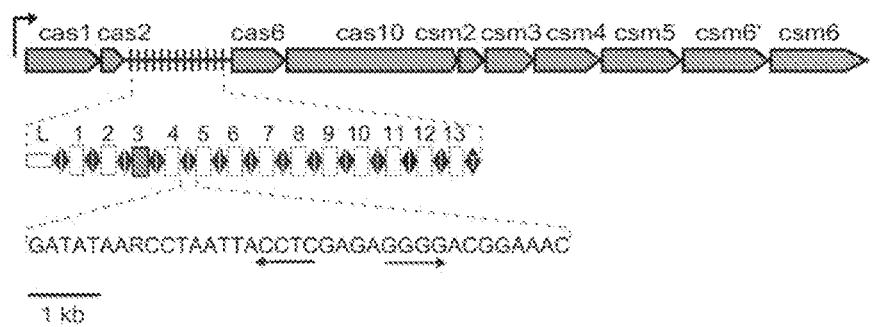
FIGS. 1A-H show cloning, isolation and characterization of the Type III-A Csm complex of *S. thermophilus* DGCC8004.
Figure 8:
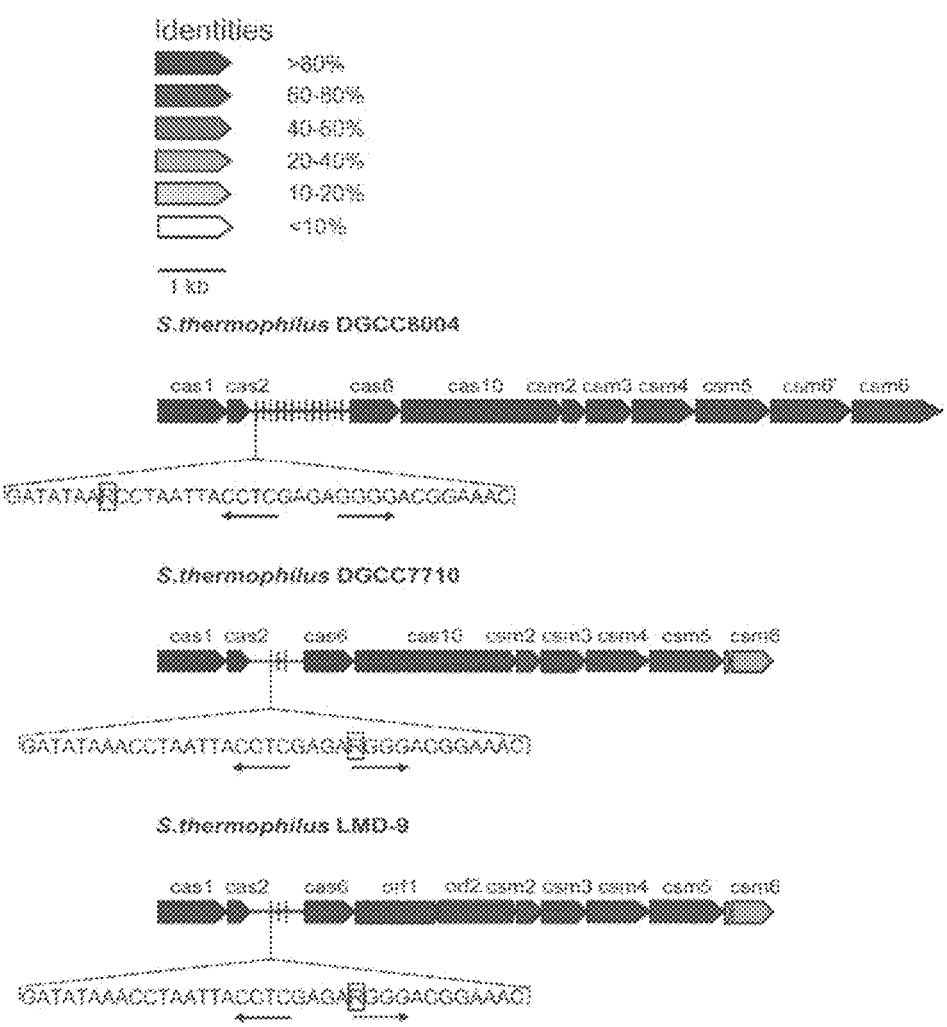
FIG. 8 shows schematic organization of the Type III-A CRISPR-Cas systems of *Streptococcus thermophilus* DGCC8004, DGCC7710, LMD-9, *Staphylococcus epidermidis* RP62a, *Enterococcus italicus* DSM15952, *Lactococcus lactis* DGCC7167 and *Sulfolobus solfataricus* P2. Schematic organization of the Type 1II-A CRISPR-Cas systems of *Streptococcus thermophilus* DGCC8004 (GenBank KM222358) (SEQ ID NO: 106), DGCC7710 (GenBank AWVZ01000003) (SEQ ID NO: 117), LMD-9 (GenBank NC008532) (SEQ ID NO: 117), *Staphylococcus epidermidis* RP62a (GenBank NC002976) (SEQ ID NO: 118), *Enterococcus italicus* DSM15952 (GenBank AEPV01000074) (SEQ ID NOS 119 and 119), *Lactococcus lactis* DGCC7167 (GenBank JX524189) (SEQ ID NO: 120) and *Sulfolobus solfataricus* P2 (GenBank AE006641)*. Arrows are shaded according to the percentage of identical residues (Vector NTI AlignX tool) in Csm/Cas proteins in respect to the *S. thermophilus* DGCC8004. Conserved repeat sequences are shown in the inserts. Partially palindromic repeat sequences are indicated by arrows. In *L. lactis* DGCC7167 CRISPR2 system Ich gene which shows a partial homology to the relE/parE toxin gene is present instead of cas2 (Millen et al., 2012). In CRISPR-Cas loci of *S. thermophilus* LMD-9 and *S. solfataricus* P2 cas10 is split in two open reading frames ORF1 and ORF2. The Type III-A system of DGCC8004 contains 10 cas genes flanking the CRISPR2 array and includes cas1, cas2, cas6, cas10, csm2, csm3, csm4, csm5, csm6 and csm6' genes. The DGCC8004 CRISPR2 locus share similar gene arrangement to that of DGCC7710 (GenBank AWVZ00000000, (Horvath and Barrangou, 2010)) and LMD-9 (GenBank NC_008532, (Makarova et al., 2006)). The major difference is an additional csm6' gene in DGCC8004. The Csm6' protein in DGCC8004 is comprised of 386 aa and shows—34% amino acid identity to the 428 aa Csm6 protein, suggesting a possible ancient gene duplication event followed by sequence divergence. In contrast, DGCC7710 contains only a short 117-nt ORF in front of csm6. The Cas/Csm proteins associated to CRISPR2 in DGCC8004 are homologous to the corresponding proteins in DGCC7710 and LMD-9 (more than 90% aa identity, except for the Csm2 protein, which shares ~70% identity). Other experimentally characterized Type III-A systems including S. epidermidis RP62a (GenBank NC002976, (Marraffini and Sontheimer, 2008)), Enterococcus italicus DSM15952 (GenBank AEPV01000074, (Millen et al., 2012)) and Lactococcus lactis DGCC7167 (GenBank JX524189, (Millen et al., 2012)) share with DGCC8004 a conserved arrangement of the cas10-csm2-csm3-csm4-csm5-csm6 gene cluster, while the position of cas6 and cas1/cas2 genes differ in some strains. The Type III-A signature protein Cas10 of DGCC8004 shows ~34-40% identity (~50-55% similarity) to Cas10 of S. epidermidis, E. italicus and L. lactis. In LMD-9, the cas10 gene is split into two ORFs which match to the N- and C-terminal fragments of Cas10 in DGCC8004 (>92% identical aa). Type III-A CRISPR-Cas locus in S. solfataricus P2 (GenBank AE006641) has different gene organization and shows low protein sequence similarity to Cas/Csm orthologues in DGCC8004. Noteworthy, the Csm3 protein is most conserved among the Cas/Csm proteins across different strains and 5 copies of the Csm3 paralogues are present in S. solfataricus. Repeat sequences in S. epidermidis, E. italicus and L. lactis are of the same length (36 nt), however the nucleotide conservation is limited to the palindromic parts and 3'-terminal end of the repeats. The 8-nt 3'-terminal sequence of the repeat, which may contribute to the crRNA 5'-handle, shows an ACGRRAAC consensus between S. thermophilus, S. epidermidis, E. italicus and L. lactis but differs from that of S. solfataricus (AUUGAAG (Rouillon et al., 2013)).
Figure 9A:
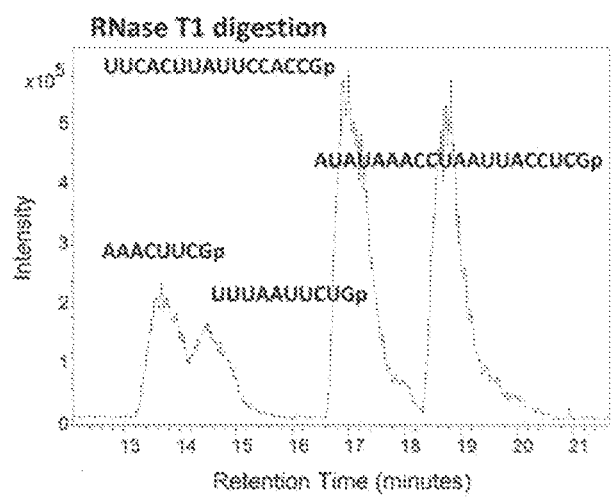
FIGS. 9A-D show ESI MS/MS oligoribonucleotide mapping of crRNA isolated from StCsm-72 and StCsm-40. ESI MS/MS oligoribonucleotide mapping of crRNA isolated from StCsm-72 and StCsm-40.
Figure 9B:
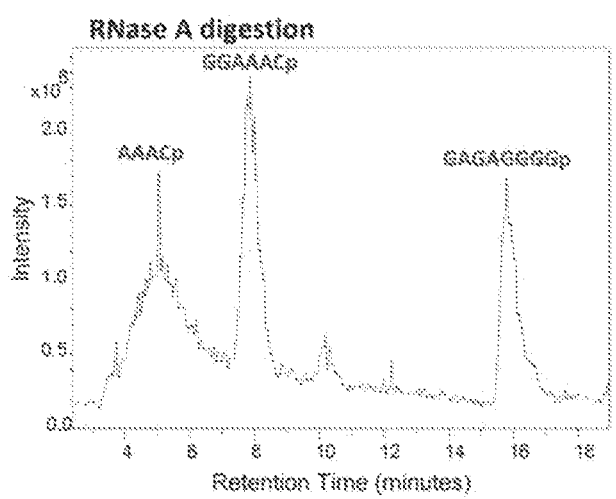
Figure 9C:
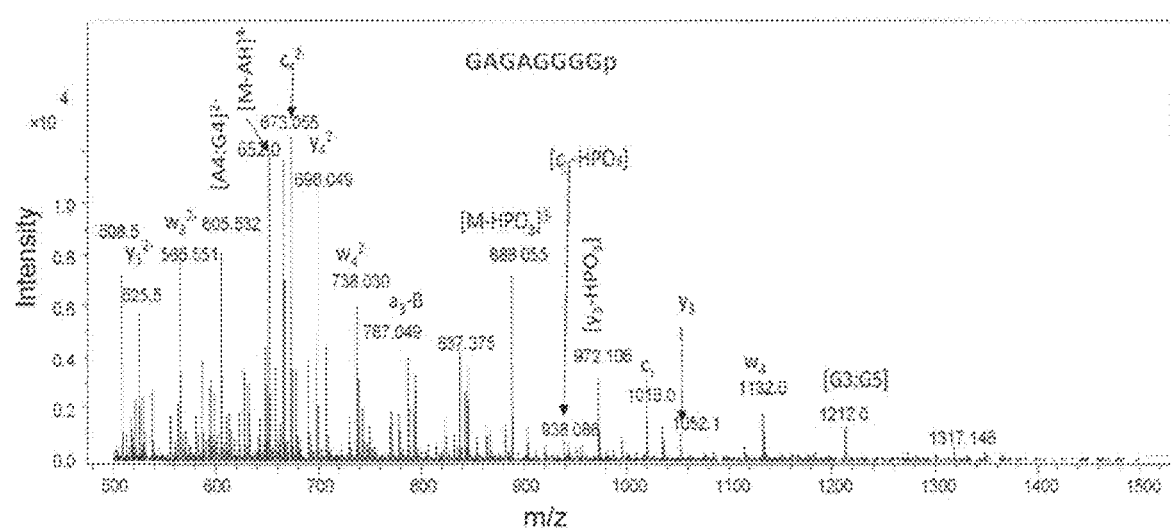
Figure 9D:
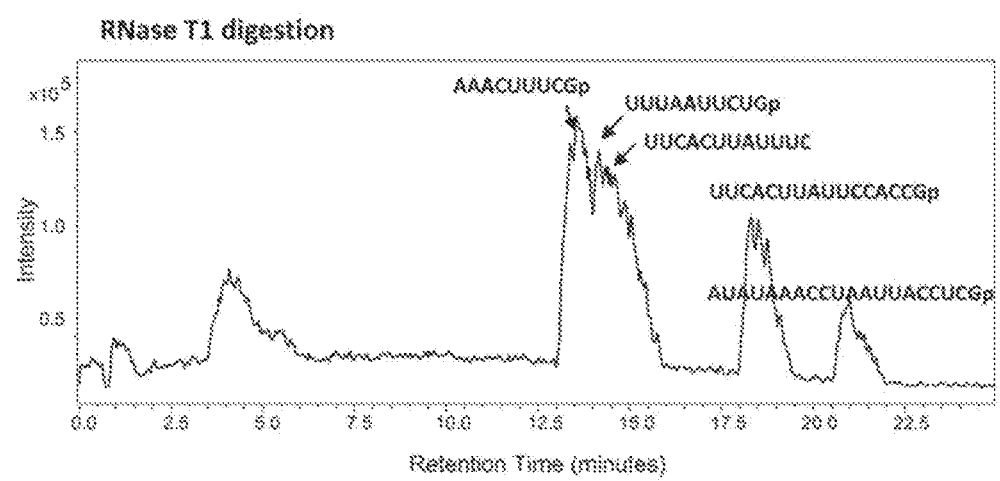

S. thermophilus strain DGCC8004 carries 13 spacers in its Type III-A CRISPR2 array (FIGS. 1A and 8). This strain also contains a Type II CRISPR1 system that is ubiquitous in the S. thermophilus species. In the CRISPR2 locus of DGCC8004 the 36-nt repeat sequences, that are partially palindromic, are conserved with the exception of the two terminal repeats (FIG. 1A). An A+T rich 100-bp leader sequence is located upstream of the CRISPR2 array.

Figure 1B:
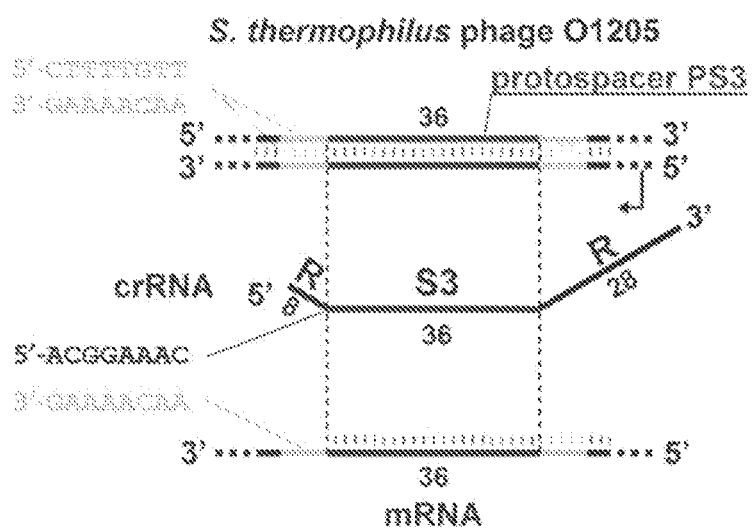

DGCC8004 CRISPR2 (Type III-A) spacers range in size between 34 and 43 nt, but 36-nt spacers are the most abundant. In total, 38 unique spacers were identified among CRISPR2-positive S. thermophilus strains and a majority (20 out of 38) of these spacer sequences have matches (protospacers) in S. thermophilus DNA phage sequences, although phage interference for the S. thermophilus CRISPR2 locus has not yet been demonstrated. Analysis of the sequences located immediately upstream and downstream of these protospacers failed to identify any consensus sequence as a putative PAM, either due to the relatively small number of protospacers or targeting of RNA that is often PAM-independent (Hale et al., 2009). In DGCC8004, although no CRISPR2 spacer gives perfect identity with currently known sequences, 6 spacers out of 13 (S3, S4, S6, S8, S12 and S13) show strong sequence similarity with S. thermophilus DNA phages (at least 94% identity over at least 80% of spacer length). All phage matching protospacers appear to have been selected from the template strand. For example, the 36-nt spacer S3 matches 34 nt of a protospacer in the S. thermophilus phage 01205 genome (FIG. 1B). A corresponding crRNA would match the template DNA strand of the protospacer S3, and would pair with the target sequence on the coding strand of phage DNA or the respective mRNA sequence. If crRNA processing in the S. thermophilus Type III-A locus was similar to that in S. epidermidis (Hatoum-Aslan et al., 2011; Hatoum-Aslan et al., 2014; Hatoum-Aslan et al., 2013), the resulting crRNA 5'-handle in the mature crRNA would be non-complementary to the protospacer S3 3'-flank in the phage DNA coding strand or mRNA (FIG. 1B). In the S. epidermidis Type III-A system, which limits the spreading of plasmid DNA, the crRNA/target DNA non-complementarity outside of the spacer sequence plays a key role in silencing of invading DNA and self vs non-self DNA discrimination (Marraffini and Sontheimer, 2010). Taking these elements into consideration, crRNA encoded by the spacer S3 was selected as the guide, and a complementary protospacer sequence as the NA target (DNA or RNA) (FIG. 1B).

Figure 1C:
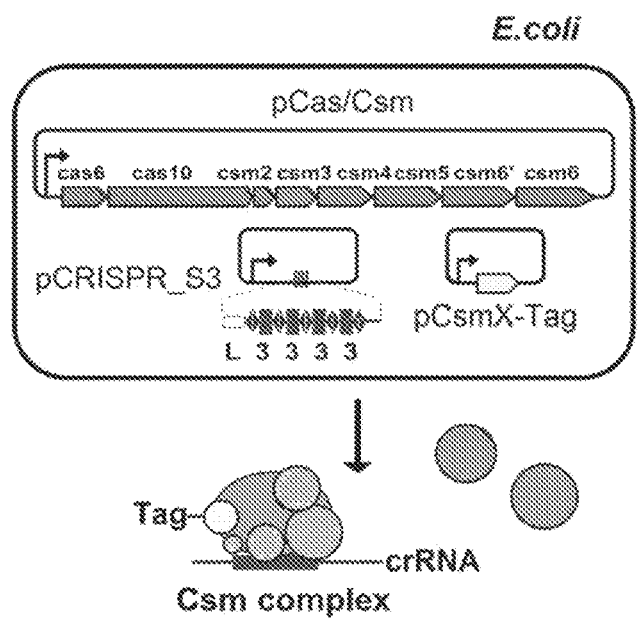

Cloning, Expression, and Isolation of the S. thermophilus DGCC8004 Type III-A Effector Complex To isolate the Type III-A RNP effector complex (StCsm) of the DGCC8004, the CRISPR2 locus was split into the three fragments and cloned them into three compatible vectors (FIG. 1C). Plasmid pCas/Csm contained a cassette including all the cas/csm genes (except cas1 and cas2), while plasmid pCRISPR_S3 carried 4 identical tandem copies of the repeat-spacer S3 unit flanked by the leader sequence and the terminal repeat. Plasmids pCsm2-Tag or pCsm3-Tag carried a StrepII-tagged variant of csm2 or csm3 genes, respectively. Next, all three plasmids were co-expressed in E. coli BL21(DE3) and tagged Csm2 or Csm3 proteins were isolated by subsequent Strep-chelating affinity and size exclusion chromatography.

Figure 1D:
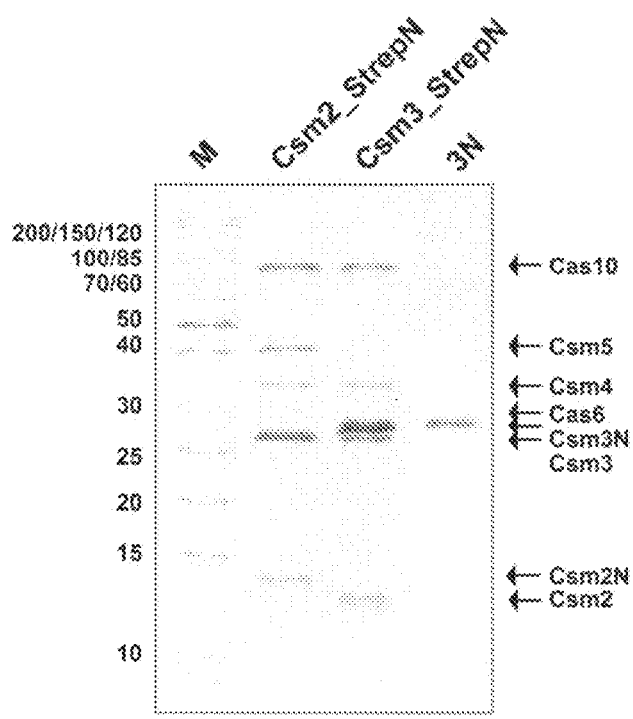

Strep-tagged Csm2 or Csm3 proteins pulled-down from E. coli lysates co-purified with other Csm/Cas proteins suggesting the presence of a Csm complex (FIG. 1D). Csm complexes isolated via N-terminus Strep-tagged Csm2 (Csm2_StrepN) and the N-terminus Strep-tagged Csm3 proteins (Csm3_StrepN) were subjected to further characterization. SDS-PAGE of these complexes revealed six bands that matched the individual Cas proteins Cas6, Cas10, Csm2, Csm3, Csm4 and Csm5 (FIG. 1D). The identity of proteins in these Csm complexes was confirmed by mass spectrometry (MS) analysis (Tables 1 and 2).

Figure 1E:
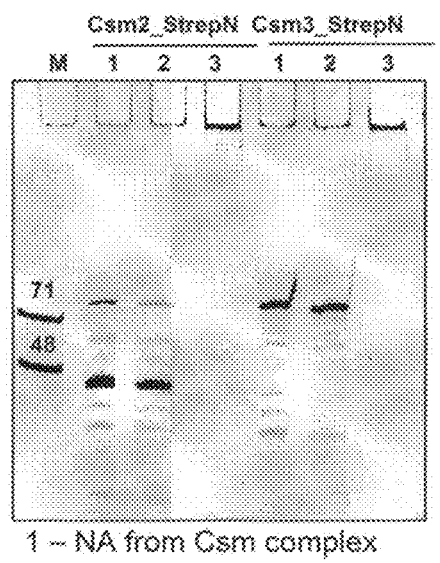

The Csm complexes were examined for the presence of NA using basic phenol-chloroform extraction followed by RNase I or DNase I digestion. Denaturing PAGE analysis revealed that ~70-nt and ~40-nt RNA molecules co-purified with the Csm3_StrepN and Csm2_StrepN pulled-down Csm complexes, respectively (FIG. 1E). The complex isolated via Csm2_StrepN subunit also contained ~10% of the ~70-nt RNA. When subjected to RNase I protection assay the RNA in the complexes showed no visible degradation, indicating that the RNA is tightly bound and protected along its entire length (data not shown).

Characterization of the crRNA

Figure 1F:
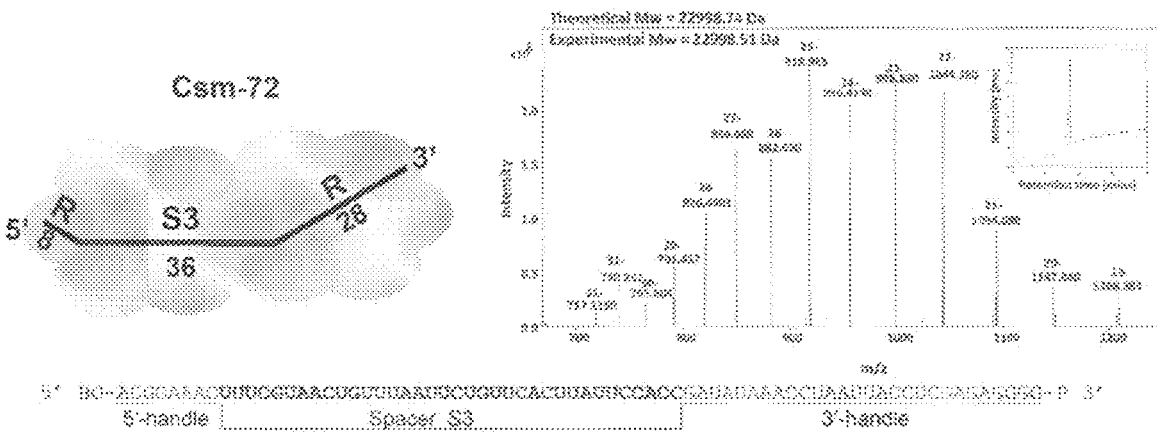
Figure 1G:
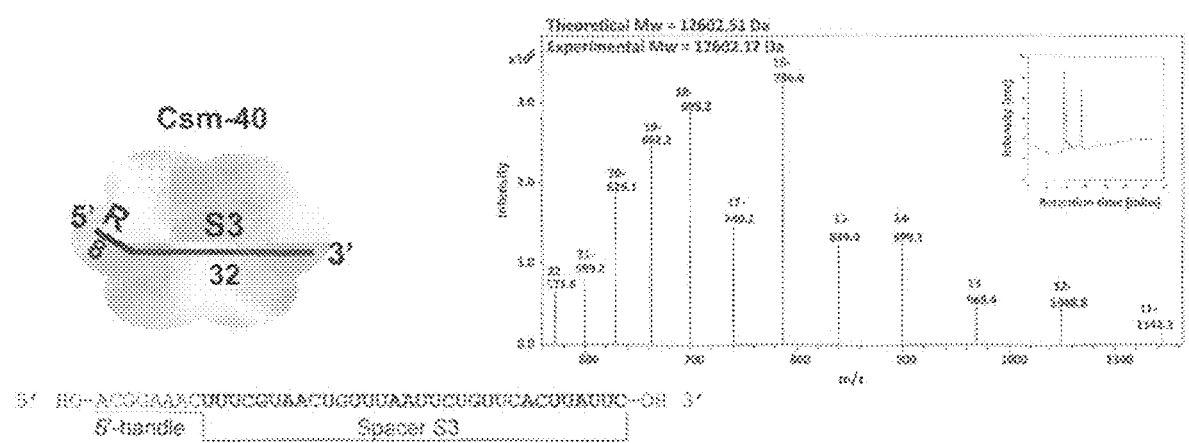

Denaturing RNA chromatography was used in conjunction with electrospray ionization mass spectrometry (ESI-MS) to analyse the crRNA sequence and determine the chemical nature of the 5'- and 3'-termini of crRNAs co-purified with both Csm complexes. Denaturing ion pair reverse phase chromatography was used to rapidly purify the crRNA directly from the Csm complexes. The crRNA isolated from the Csm3_StrepN pull-down complex revealed a single crRNA with a retention time consistent with an approximate length of 70 nt (FIG. 1F). The crRNA isolated from Csm2_StrepN pull-down complex revealed the presence of an additional crRNA, with a retention time consistent with an approximate length of 40 nt (FIG. 1G). Purified crRNAs were further analyzed using ESI-MS to obtain the accurate intact masses. A molecular weight of 22 998.5 Da was obtained for RNA isolated from Csm3 and 12 602.2 Da for RNA isolated from Csm2 pull-downs, respectively. Csm2 pull-down also contained a minor component, with a molecular weight of 12 907.3 Da (data not shown). In addition, ESI MS/MS was also used to analyze the oligoribonucleotide fragments generated from RNase A/T1 digestion of the crRNAs (FIG. 9). In conjunction with the intact mass analysis, these results revealed a 72-nt crRNA in the complex isolated via Csm3 (further termed Csm-72 according to the length of crRNA) and a 40-nt crRNA in the complex isolated via Csm2 (further termed Csm-40 complex). The MS analysis of the 72-nt crRNA is consistent with the pre-CRISPR cleavage at the base of the CRISPR RNA hairpin to yield a 8-nt 5'-handle, a 36-nt spacer and a 28-nt 3'-handle with 5'-OH and 3'-P, and could represent unmature crRNA intermediate (FIG. 1F) similar to that of Type III-A and III-B CRISPR-Cas systems (Hale et al., 2009; Hatoum-Aslan et al., 2013). Further verification of the 3'-P termini was obtained upon acid treatment of the 72-nt crRNA where no change in mass was observed using ESI-MS. Likewise, the MS analysis of the 40-nt crRNA in the Csm-40 complex revealed an 8-nt 5'-handle and a 32-nt spacer with 5'-OH and 3'-OH that would correspond to the mature crRNA (FIG. 1G). The difference in the chemical nature of the 3'-end between intermediate and mature crRNAs suggests that primary processing and final maturation are achieved by distinct catalytic mechanisms as proposed by Hatoum-Aslan for the *S. epidermidis* model system (Hatoum-Aslan et al., 2011).

Composition and Shape of the Csm Complex

Evaluation of the complex composition by densitometric analysis of the SDS gels suggests the $Cas10_1$:$Csm2_6$:$Csm3_{10}$:$Csm4_1$:$Csm5_{0.14}$ stoichiometry for Csm-72, and the $Cas6_{0.10}$:$Cas10_1$:$Csm2_3$:$Csm3_5$:$Csm4_1$:$Csm5_1$ stoichiometry for Csm-40. Fraction numbers for Cas6 and Csm5 proteins are presumably due to the weak transient interactions of these proteins in the respective complexes. Protein subunits that are involved in pre-crRNA processing, e.g. Cas6, would not necessarily occur in stoichiometric amounts in the purified effector complex.

Small angle X-ray scattering (SAXS) measurements was also performed in order to characterize the molecular mass/shape of both Csm-40 and Csm-72 effector complexes in solution. $M_w$ values obtained using SAXS are in agreement both with DLS and gel-filtration data (Table 3). Taken together these data are consistent with the stoichiometry $Cas10_1$:$Csm2_6$:$Csm3_{10}$:$Csm4_1$:$crRNA_1$ (calculated Mw 486.2 kDa including the 72-nt crRNA) for Csm-72 and $Cas10_1$:$Csm2_3$:$Csm3_5$:$Csm4_1$:$Csm5_1$:$crRNA_1$ (calculated Mw 344.8 kDa including 40-nt crRNA) for Csm-40.

Figure 1H:
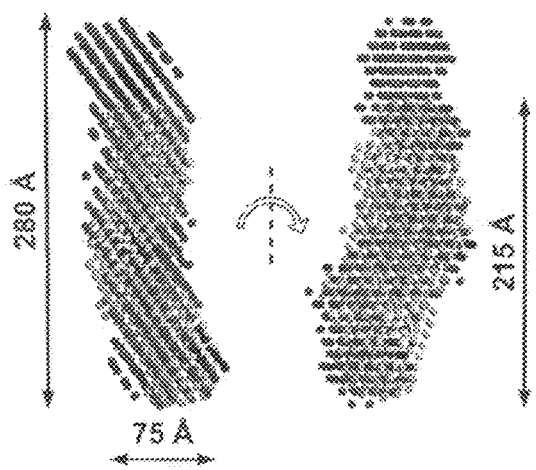
Figure 10A:
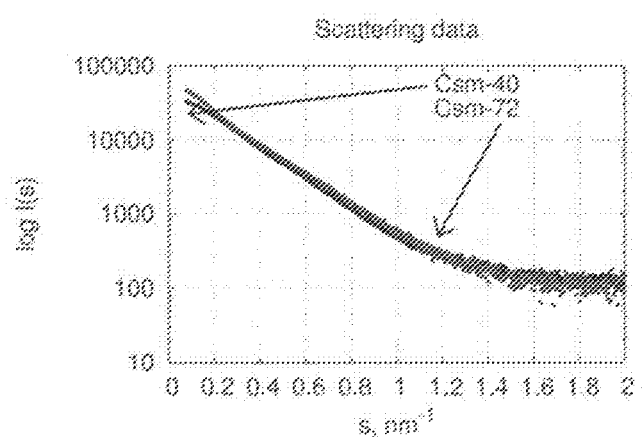
(FIGS. 10A-E show SAXS data for StCsm complexes. SAXS data for StCsm-40 (black dots) and StCsm-72 (gray dots) are shown.
Figure 10B:
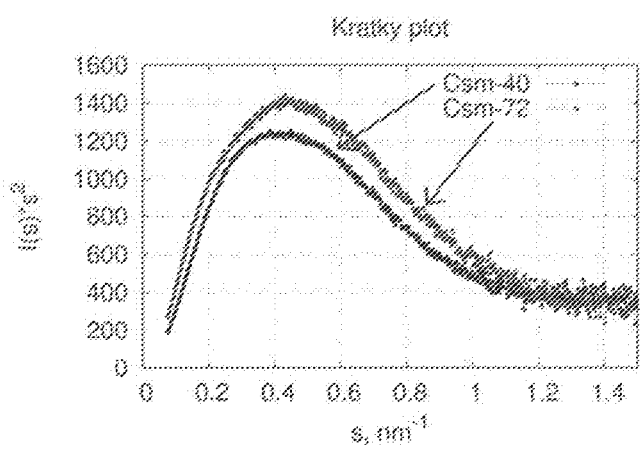
Figure 10C:
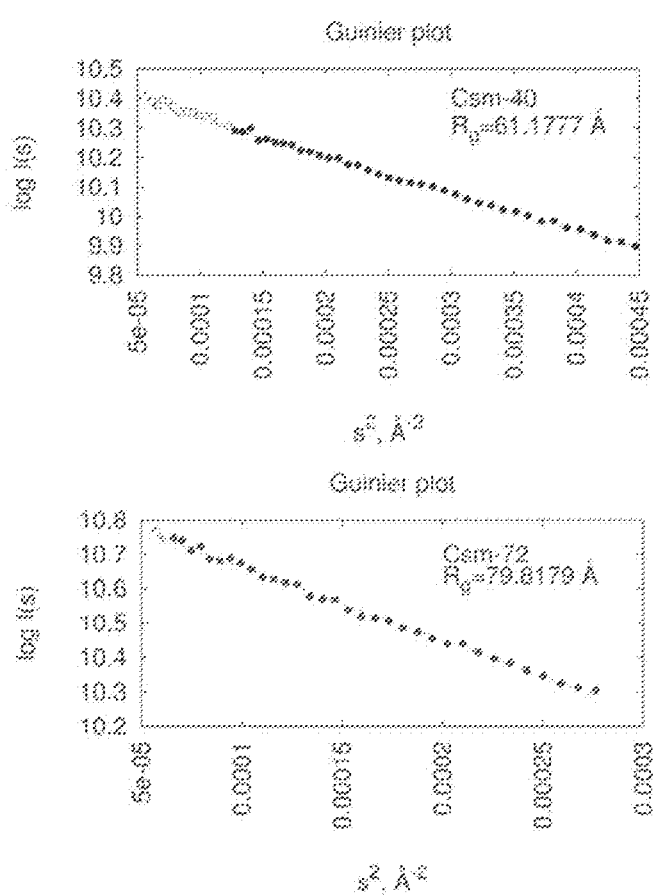
Figure 10D:
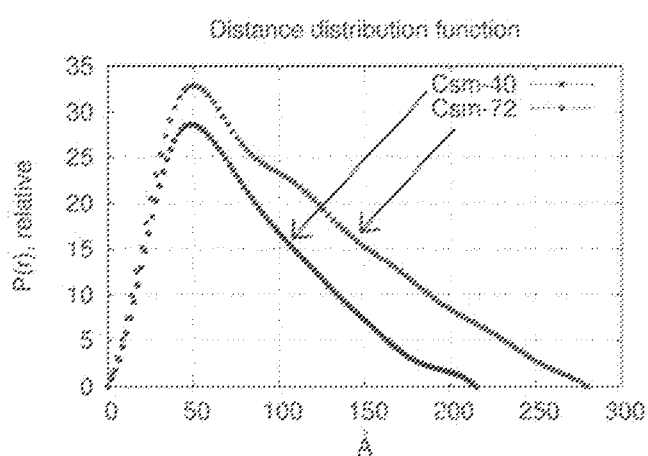
Figure 10E:
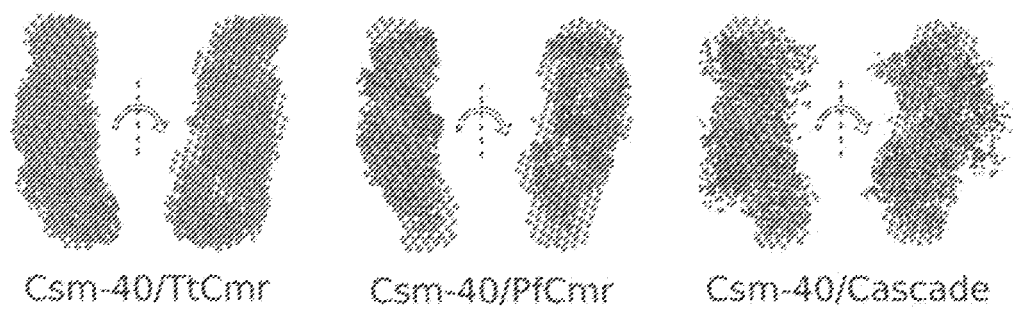

SAXS measurements revealed that the Csm-40 complex in solution has elongated and slightly twisted shape. The maximal interatomic distance ($D_{max}$) of the complex estimated from SAXS data is 215 Å, whereas its diameter is 75-80 Å (Table 4). The shape of this effector complex (FIG. 1H) is very similar to the electron microscope structure of Cmr complexes from *Thermus thermophiles* (Staals et al. 2013), *Pyrococcus furiosus* (Spilman et al. 2013) and Cascade from *E. coli* (Wiedenheft et al., 2011) (FIG. 10E). The Csm-72 complex with $D_{max}$ of 280 Å (Table 4) is significantly more elongated than the Csm-40 complex (FIG. 1H). The lowest normalized spatial discrepancy was obtained for the end-to-end superimposition of the Csm-40 and Csm-72 models (FIG. 1H).

Nucleic Acid Specificity of the Type III-A StCsm Complex

Figure 2A:
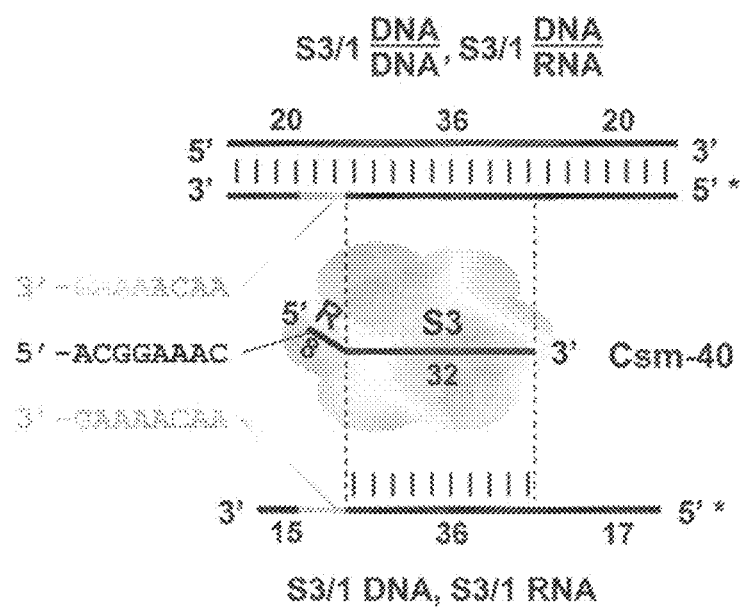
FIGS. 2A-E show nucleic acid binding and cleavage by the Type III-A Csm complex of *S. thermophilus*.
Figure 2B:
Figure 2C:
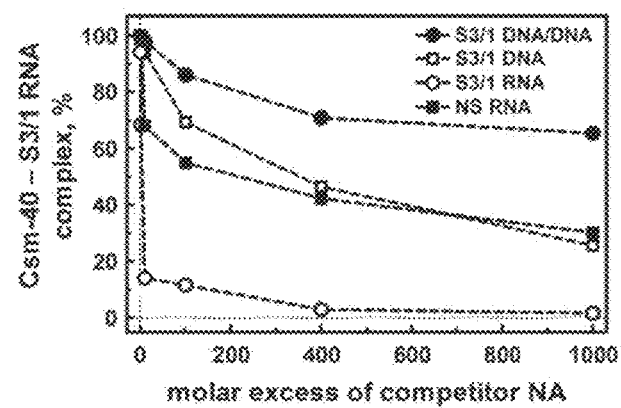
Figure 2D:
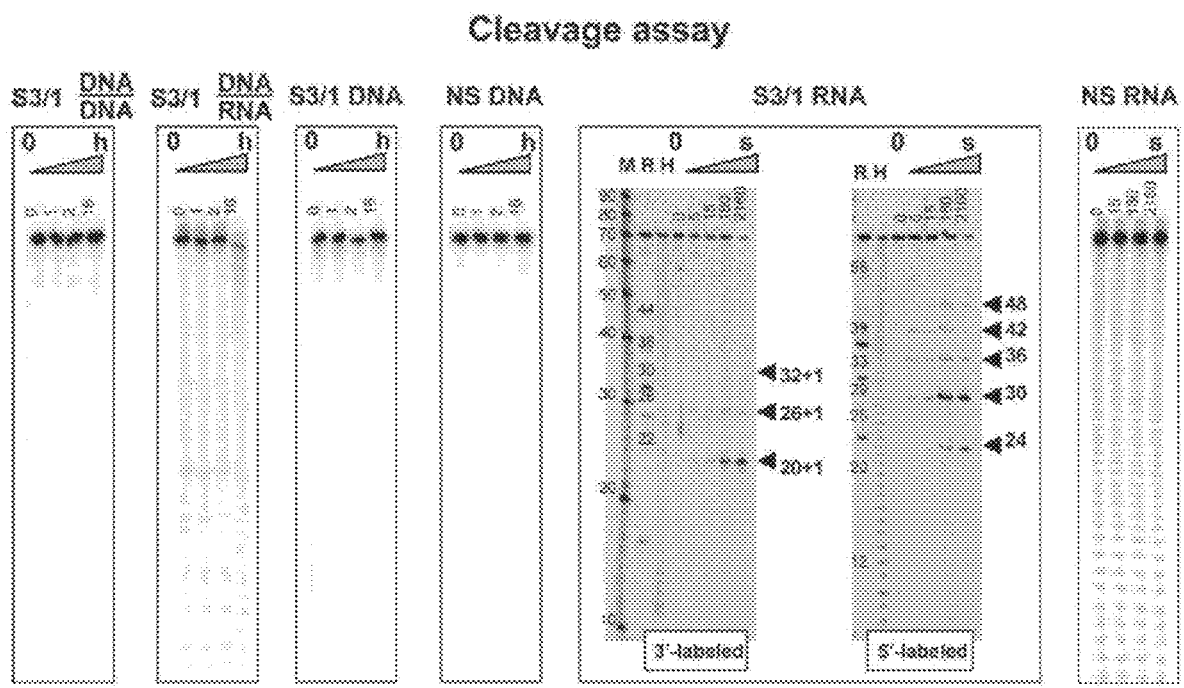

In the CRISPR2 locus of DGCC8004, 34 out of 36 nt of the spacer S3 match a sequence present in the genome of *S. thermophilus* phage 01205. Thus, to probe the functional activity of the Csm-40 complex, DNA and RNA substrates were first designed that are fully complementary to the 32-nt crRNA encoded by spacer S3 and that carry phage O1205-flanking sequence. These flanking sequences lack complementarity to the 8-nt 5'-handle of the crRNA identified in the Csm-40/Csm-72 complexes (FIG. 2A and Table 5). For binding analysis DNA or RNA substrates were 5'-end radioactively labeled and the Csm-40 complex binding was evaluated by an electrophoretic mobility shift assay (EMSA) in the absence of any divalent metal ($Me^{2+}$) ions. Csm-40 showed weak affinity for oligoduplex S3/1 DNA/DNA and DNA/RNA substrates since binding was observed only at high (100-300 nM) complex concentrations. Single-stranded S3/1 DNA (ssDNA) was bound to Csm-40 with an intermediate affinity ($K_d \approx 30$ nM), whereas a single-stranded S3/1 RNA (ssRNA) showed high affinity binding ($K_d \approx 0.3$ nM) (FIG. 2B). Binding competition experiments with various nucleic acids further supported the single-stranded RNA specificity for the Csm-40 complex (FIG. 2C). Cleavage data correlated with the binding affinity: S3/1 DNA/DNA, DNA/RNA and ssDNA are refractory to cleavage, whereas S3/1 ssRNA complementary to the crRNA is cut by Csm-40 in the presence of $Mg^{2+}$ ions (FIG. 2D). RNase activity of Csm-40 complex requires $Mg^{2+}$ or other divalent metal ions ($Mn^{2+}$, $Ca^{2+}$, $Zn^{2+}$, $Ni^{2+}$ or $Cu^{2+}$) and is inhibited by EDTA (FIG. 11E).

Figure 2E:
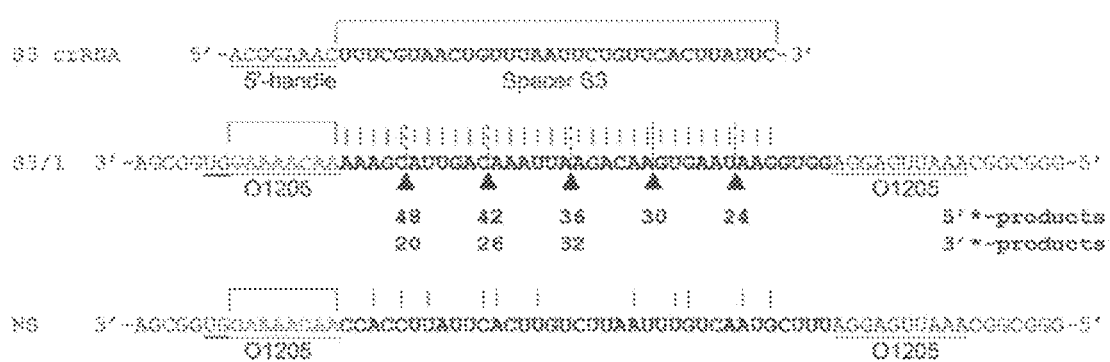

Csm-40 cuts the S3/1 RNA target at 5 sites regularly spaced by 6-nt intervals to produce 48-, 42-, 36-, 30- and 24-nt products, respectively (FIGS. 2D, 2E). The sequence complementarity between the crRNA in the complex and the RNA target is a key pre-requisite for the cleavage: a non-specific RNA (FIG. 2E, bottom) was resistant to Csm-40. The Csm-40 cleavage pattern of the 3'-labeled S3/1 RNA substrate differs from that of the 5'-labeled variant. While the 5'-labeled substrate cleavage produces 48-, 42-, 36-, 30- and 24-nt products, short degradation products of 21, 27, and 33 nt (1 nt shift is due to an additional nucleotide added during the 3'-labeling) are visible on the gel (FIGS. 2D, 2E). Taken together, cleavage data for the 5'- and 3'-end labeled RNA substrates suggest that Csm-40 cuts the RNA molecule initially at its 3'-end and endonucleolytic degradation is further extended towards the 5'-end with 6-nt increments.

Figure 11A:
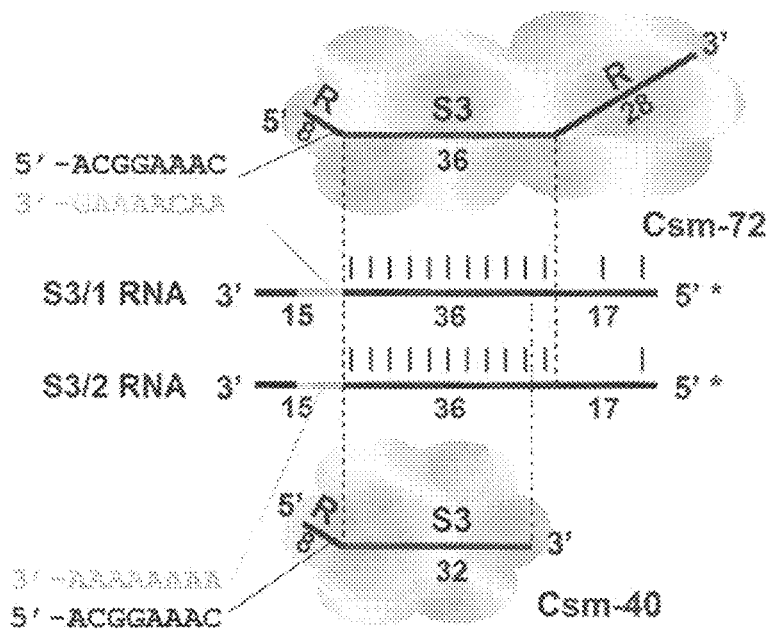
FIGS. 11A-F show target RNA binding and cleavage by StCsm-72 and StCsm-40 complexes.
Figure 11B:
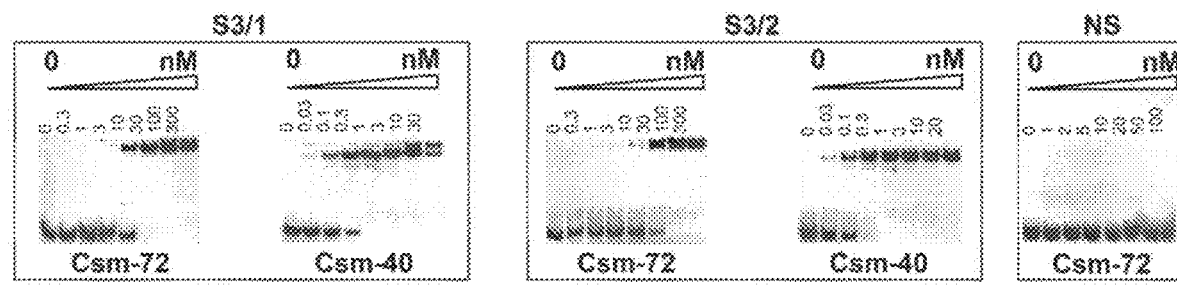
Figure 11C:
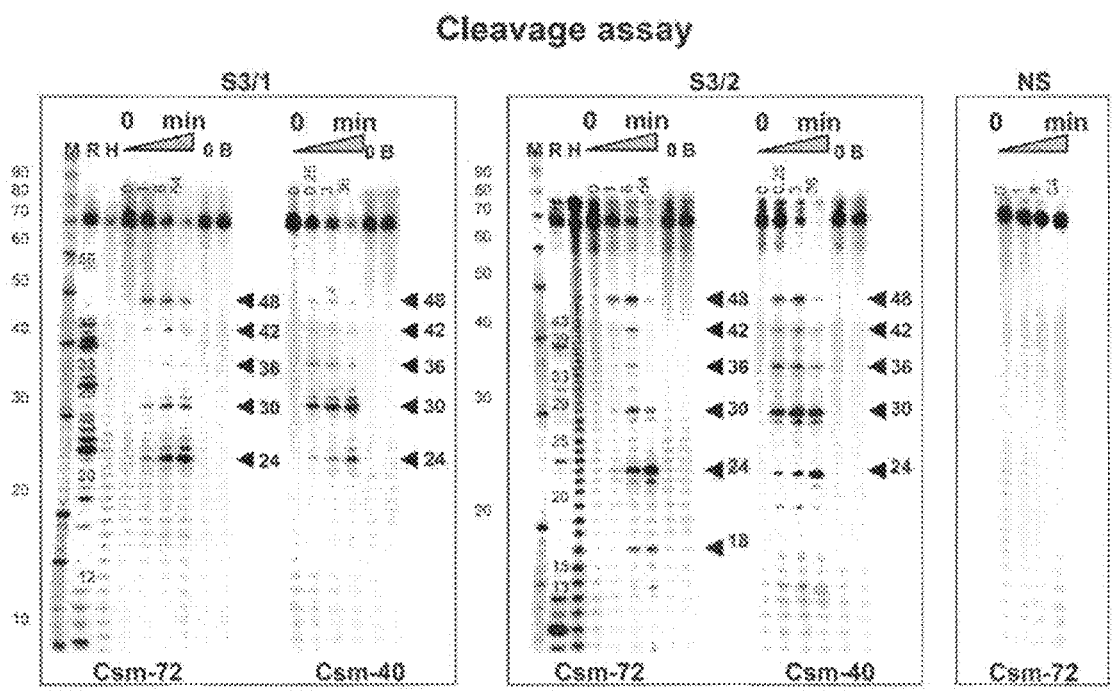
Figure 11D:
Figure 11E:
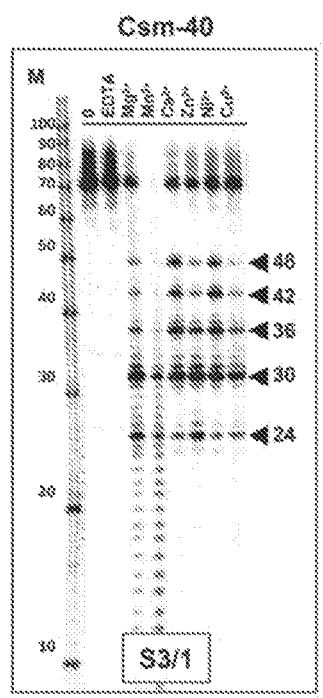
Figure 11F:
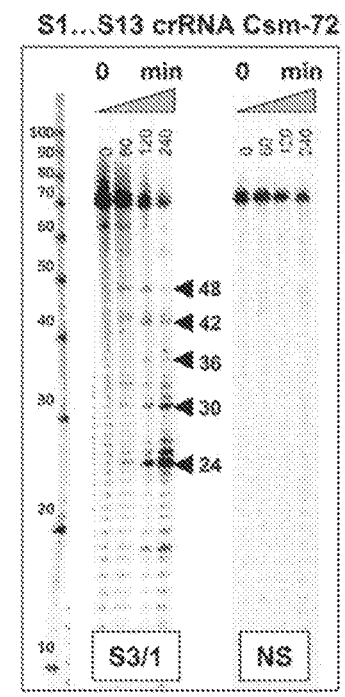

The Csm-72 complex carrying a 72-nt crRNA (8-nt 5'-handle plus 36 nt of the spacer S3 and 28 nt of the 3'-handle, FIG. 11A) showed ~30-fold weaker binding affinity ($K_d$ about 10 nM) to S3/1 RNA in comparison to the Csm-40 (FIG. 11B). Nevertheless, similar to the Csm-40 complex, in the presence of $Mg^{2+}$ ions Csm-72 cleaved S3/1 RNA, albeit at a decreased rate which may correlate with its weaker binding affinity (FIG. 11C). The 5'- and 3'-labeled S3/1 RNA cleavage pattern is identical to that of Csm-40 (FIGS. 11C, 11D and data not shown). Like the Csm-40 complex, Csm-72 showed no cleavage of S3/1 ssDNA, DNA/DNA or DNA/RNA substrates (data not shown). The heterogeneous Csm complex isolated from the *E. coli* host carrying the wt CRISPR array containing 13 spacers produces RNA cleavage products identical to those of the homogenous StCsm (FIG. 11F). Taken together, these data unambiguously demonstrated that Csm-40 and Csm-72 complexes in vitro target RNA but not DNA, and cut RNA at multiple sites regularly spaced by 6-nt intervals.

Reprogramming of the StCsm Complex

Figure 12A:
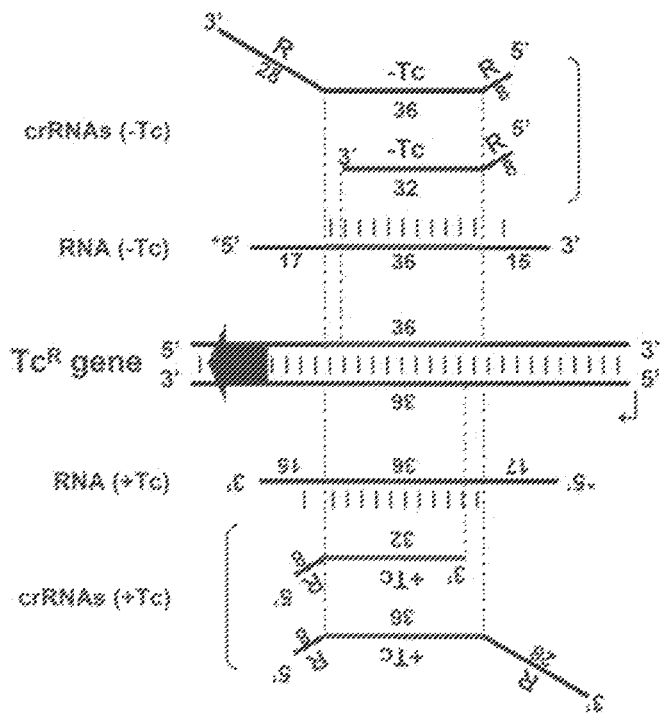
FIGS. 12A-C show reprogramming of the StCsm complex to cleave a desired RNA.
Figure 12B:
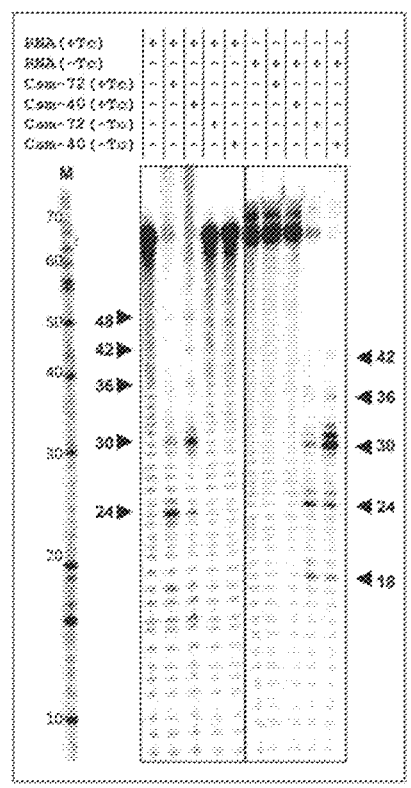
Figure 12C:
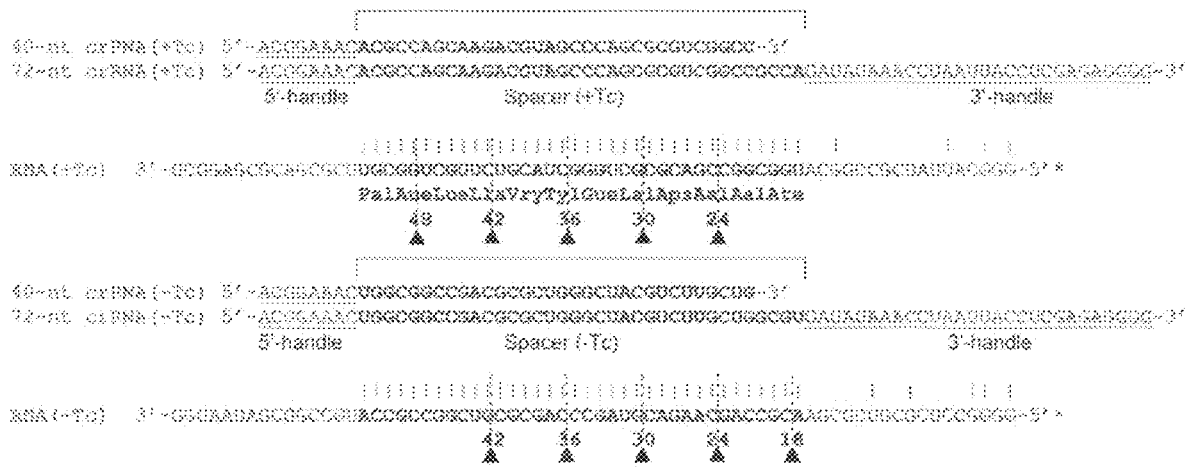

To demonstrate that the Type III-A StCsm complex can be reprogrammed to cut a desired RNA sequence in vitro, Csm complexes loaded with crRNA(+Tc) or crRNA(-Tc) targeting, respectively, the 68-nt sense(+) and anti-sense(-) mRNA fragments obtained by in vitro transcription of the tetracycline (Tc) resistance gene in the pBR322 plasmid (nts 851-886) were designed and isolated (FIG. 12A and Table 5). Both Csm-40 and Csm-72 complexes guided by the crRNA(+Tc) sliced the complementary sense RNA fragment but not the antisense RNA sequence (FIG. 12B). In contrast, Csm-40 and Csm-72 complexes guided by the crRNA(-Tc) cleaved antisense RNA but not a sense Tc mRNA fragment (FIG. 12B). In both cases target RNA was cleaved at multiple sites regularly spaced by 6-nt intervals (FIG. 12C).

To demonstrate that StCsm complex can be reprogrammed to cut the desired RNA target and silence gene expression in vivo, Csm complexes were designed that targeted the jellyfish GFP (jGFP) gene transcript in a heterologous *E. coli* host. *E. coli* BL21 (DE3) was transformed with three compatible plasmids: (i) pCRISPR_GFP plasmid bearing the synthetic CRISPR array of five repeats interspaced by four 36-nt spacers targeting the jGFP transcript; (ii) pCsm/Cas plasmid for the expression of Cas/Csm proteins; (iii) pGFP plasmid for the jGFP expression, and the jGFP transcript degradation was monitored by inspecting jGFP fluorescence in *E. coli* cells (FIG. 15). No jGFP fluorescence was detected when wt StCsm targeting the jGFP transcript is expressed in *E. coli* (FIG. 15A). On the other hand, jGFP fluorescence was observed in *E. coli* cells lacking the StCsm complex (FIG. 15B), or bearing the RNA-cleavage deficient Csm3-D33A mutant complex (FIG. 15C), or containing StCsm complex with CRISPR2 S3 crRNA (FIG. 15D). It was separately demonstrated that isolated StCsm-40 loaded with jGFP mRNA targeting crRNA (jGFP) specifically binds and cuts 68 nt length jGFP RNA in vitro (FIG. 16).

Target RNA Determinants for Cleavage by crRNA-Guided Csm Complex

Whether the nucleotide context downstream or upstream of the protospacer sequence modulates RNA cleavage by the Csm complexes was further examined. To this end, the S3/2 RNA substrate was designed in which the flanking regions originating from O1205 phage DNA in the S3/1 substrate are replaced by different nucleotide stretches that are non-complementary to the 5'-handle of crRNA in the Csm-40 and Csm-72 complexes, and to the 3'-handle in the Csm-72 complex. RNA binding and cleavage data showed that despite differences in the nucleotide context of flanking sequences in the S3/1 and S3/2 substrates, cleavage patterns for the Csm-40 and Csm-72 complexes are nearly identical, except for an extra 18-nt product for the Csm-72 (FIG. 11C).

Figure 3A:
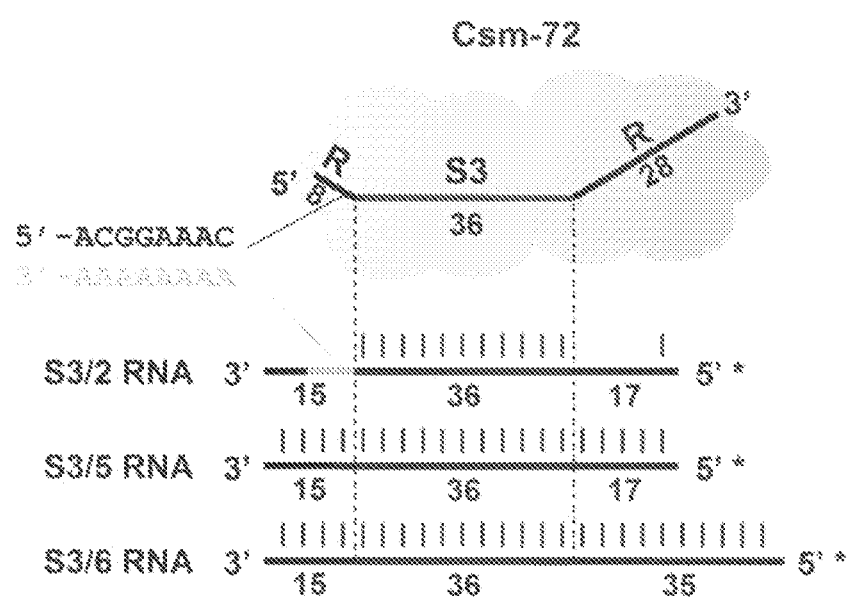
FIGS. 3A-C show the effect of the sequence complementarity outside the spacer region on the StCsm-72 cleavage pattern.
Figure 3B:
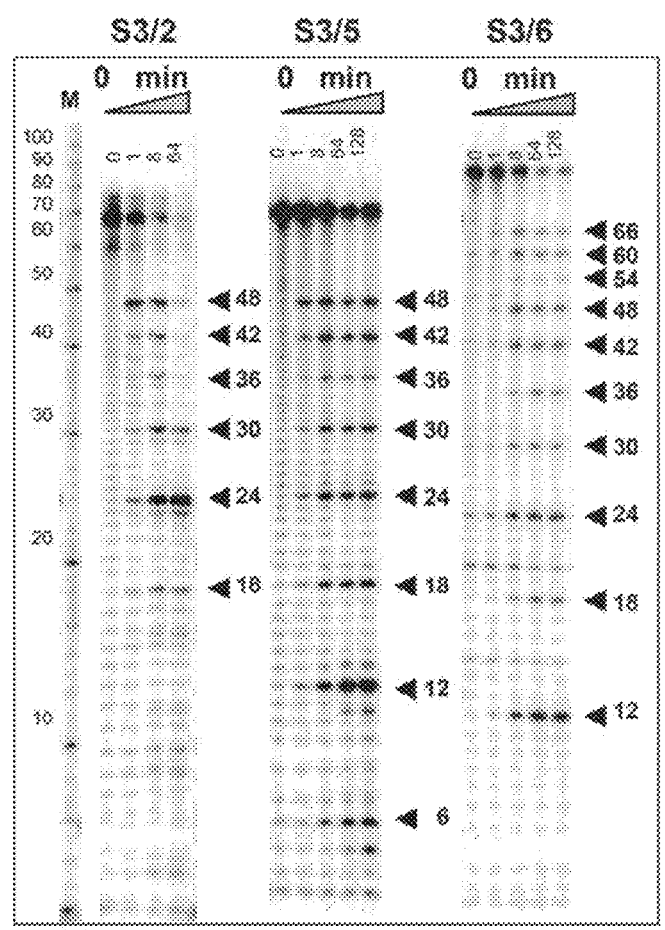
Figure 3C:
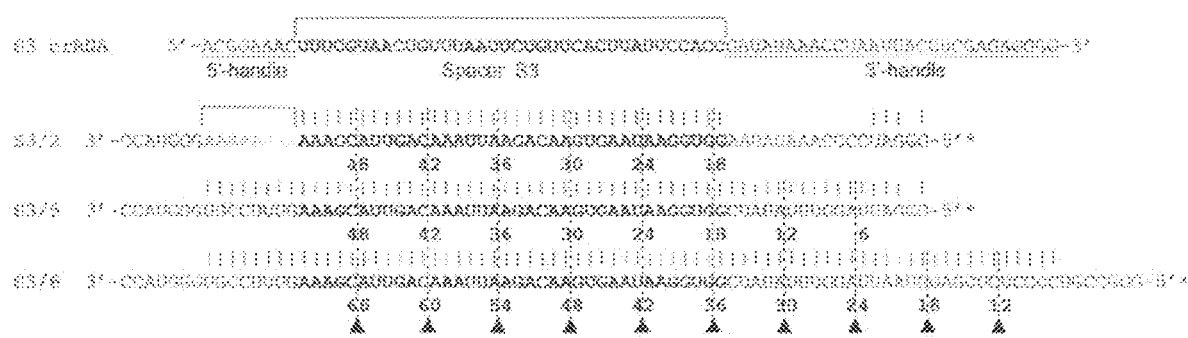
Figure 13A:
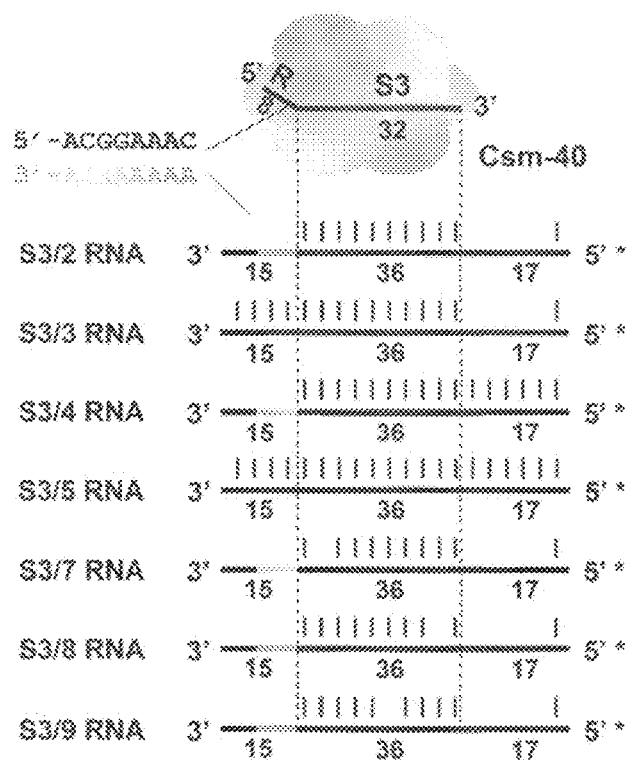
FIGS. 13A-C show the effect of crRNA:target RNA complementarity on the StCsm-40 cleavage pattern.
Figure 13B:
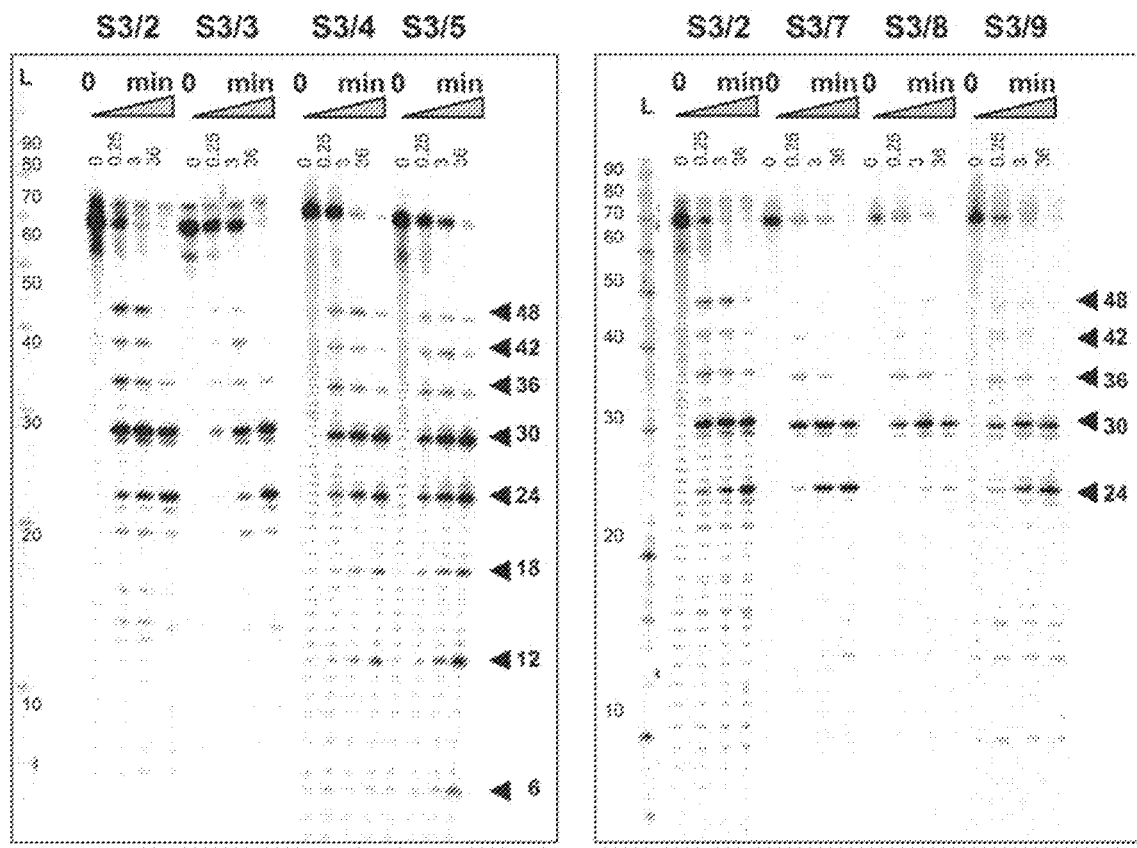
Figure 13C:
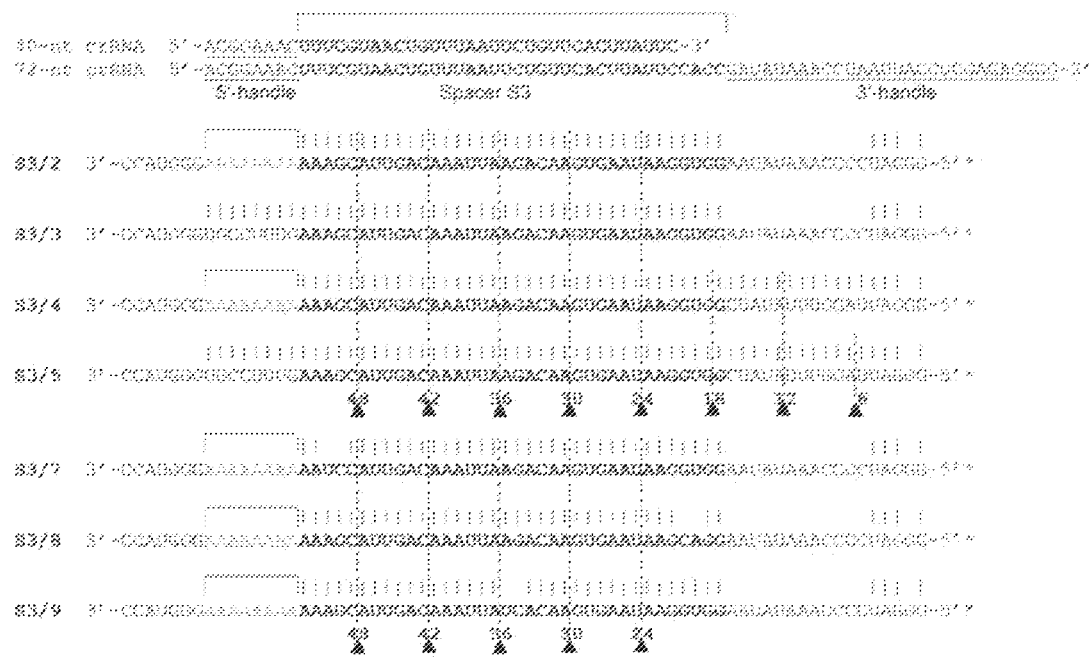

Whether the base-pairing between the flanking sequences of the RNA target and 5'- and 3-handles of crRNA in the Csm-40 and Csm-72 complexes affect either the cleavage efficiency or pattern was examined. S3/3, S3/4, and S3/5 RNA substrates were designed that contain flanking sequences complementary to the 5'-handle (40- or 72-nt crRNA), 3'-handle (72-nt crRNA) or both 5'- and 3'-handles in 72 nt-crRNA, respectively (FIG. 13A and Table 5). The cleavage analysis revealed that base-pairing between the 8-nt 5'-handle of crRNA and the 3'-flanking sequence had no effect on the cleavage pattern of the Csm-40 and Csm-72 complexes. The S3/3 substrate is cleaved with the same 6-nt step by Csm-40, suggesting that the non-complementarity of the flanking sequences is not a necessary pre-requisite for cleavage by the Csm complex (FIG. 13). For the Csm-72 complex, extension of the base-pairing between the 3'-handle of the 72-nt crRNA and the protospacer 5'-flanking sequence in S3/5 RNA substrate results in target RNA cleavage outside the protospacer, yielding 12- and 6-nt cleavage products (FIG. 3). Moreover, the S3/6 substrate, which has extended complementarity between crRNA 3'-handle and 5'-flanking sequence was cleaved at multiple positions along the full length of RNA duplex, except for the region complementary to the crRNA 5'-handle (FIG. 3). The cleavage at 18 and 12 nt outside the protospacer was also detected for the Csm-40 complex on S3/4 and S3/5 RNA substrates (FIG. 13). The 40-nt crRNA present in the Csm-40 complex lacks the 3'-handle and therefore cannot form RNA duplex with the 5'-flanking sequence in the S3/5 and S3/6 RNA substrates. However, the Csm-40 complex preparation still contains ~10% of unmatured 72-nt crRNA, and this heterogeneity results in the extra cleavage outside the protospacer (FIG. 13C).

To interrogate the importance of base-pairing within the protospacer region for target RNA cleavage, a set of RNA substrates was designed harboring two adjacent nucleotide mutations in the spacer region (substrates S3/7, S3/8 and S3/9, see FIG. 13A and Table 5). Two nucleotide mismatches in these substrates did not compromise RNA cleavage by the Csm-40 (FIG. 6) and Csm-72 complexes (data not shown), suggesting that the StCsm complex tolerates at least two contiguous mismatches in the protospacer region homologous to the crRNA.

Figure 4A:
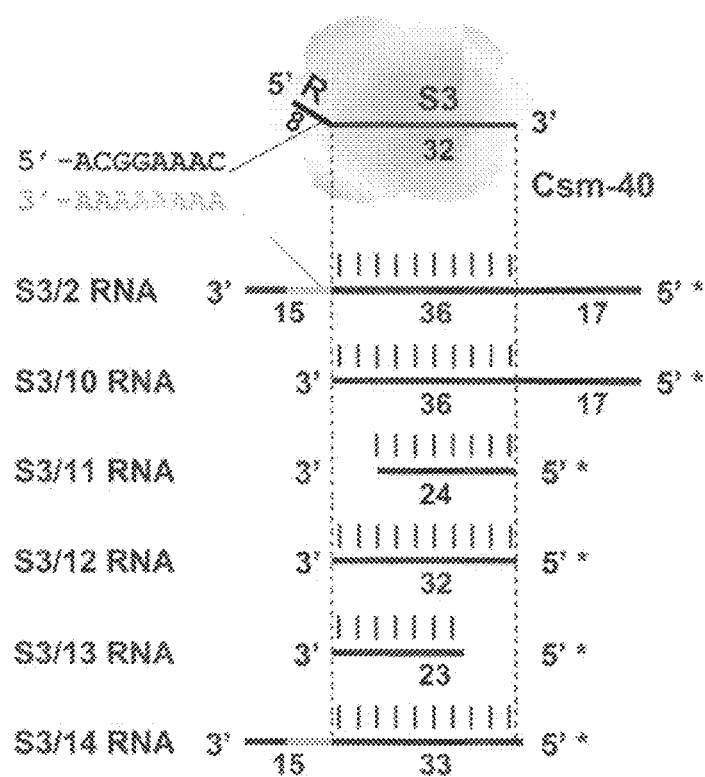
FIGS. 4A-D show the effect of protospacer truncations on the StCsm-40 cleavage pattern.
Figure 4B:
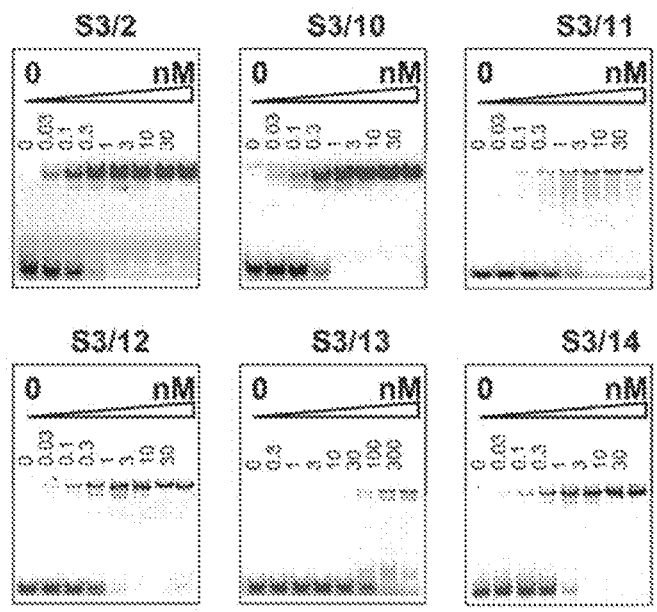
Figure 4C:
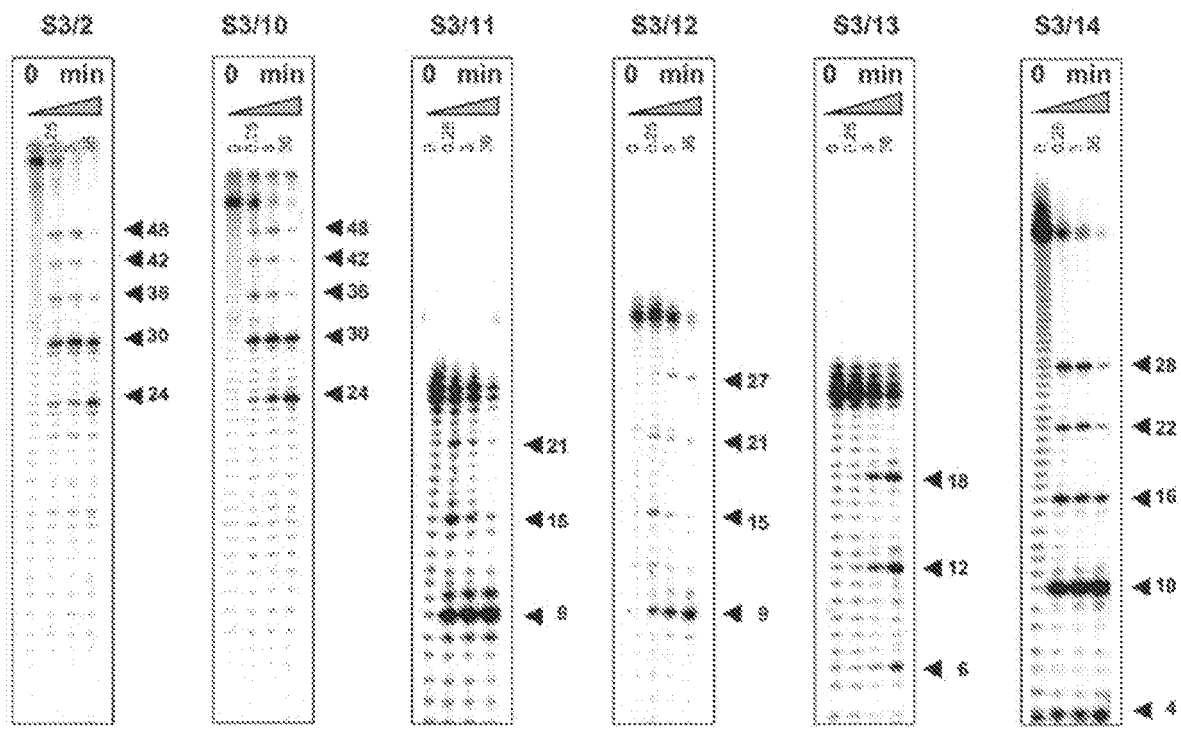
Figure 4D:
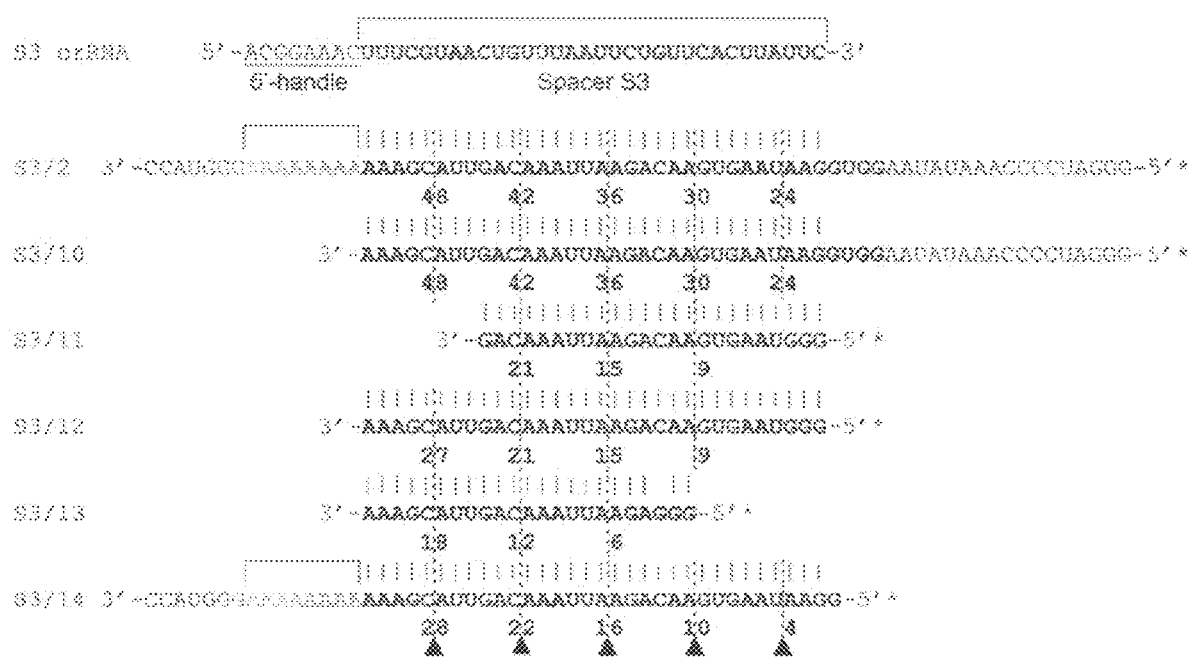

To determine whether 3'- or 5'-ends of the target RNA are important for cleavage by the Csm-40 complex, a set of truncated RNA substrates was designed. In S3/10, S3/14 and S3/12 RNA substrates unpaired flaps at the 3'-, 5'- or both ends of the target RNA were truncated, while in S3/11 and S3/13 substrates the truncations extend into the region complementary to crRNA (FIG. 4A). Binding affinity for most of the truncated substrates was not compromised (FIG. 4B) and target RNA cleavage occurred at multiple sites spaced by 6-nt intervals at conserved protospacer positions (FIG. 4C). Truncations extending into the protospacer region (S3/11 and S3/13) showed decreased binding and reduced cleavage rates. This could be a result of the decreased duplex stability; however, the role of the "seed" sequence cannot be excluded. For all RNA substrates the cleavage sites were located at a fixed distance with respect to the conserved 5'-handle of crRNA (FIG. 4C).

Identification of the Ribonuclease Subunit in the StCsm Complex

Figure 5B:
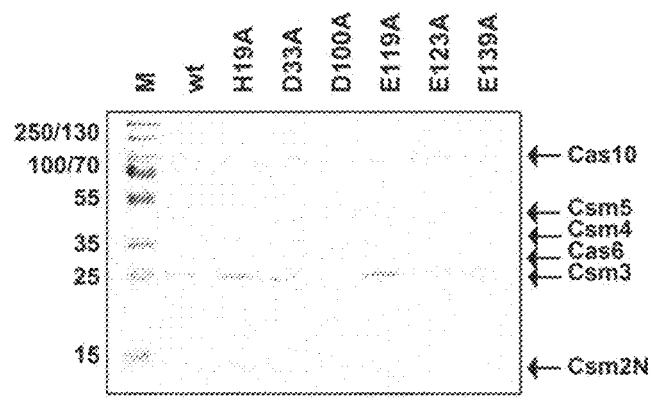
(FIG. 5B) Coomassie blue-stained SDS-PAAG of StCsm complexes containing Csm3 mutants. M—protein marker.
Figure 5C:
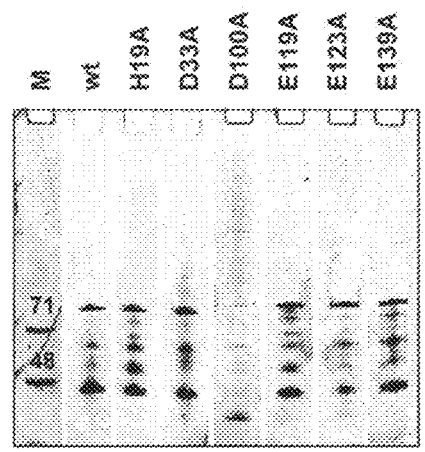
(FIG. 5C) Denaturing PAGE analysis of NA co-purifying with mutant StCsm complexes. M—synthetic DNA marker.
Figure 5D:
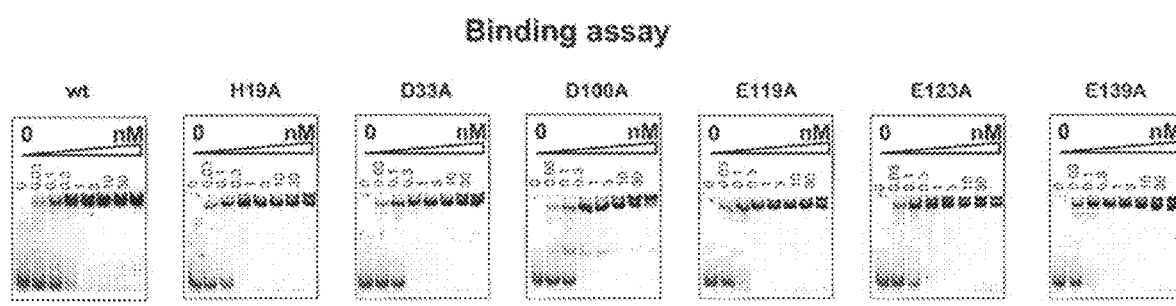
(FIG. 5D) EMSA analysis of S3/2 RNA binding by mutant StCsm complexes.
Figure 5E:
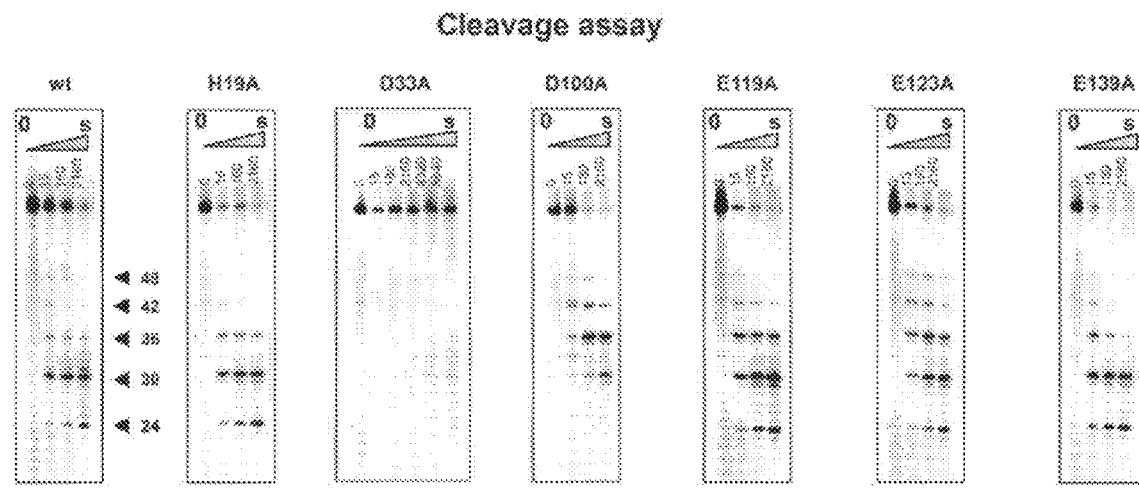
(FIG. 5E) S3/2 RNA cleavage by the mutant StCsm complexes.
Figure 5F:
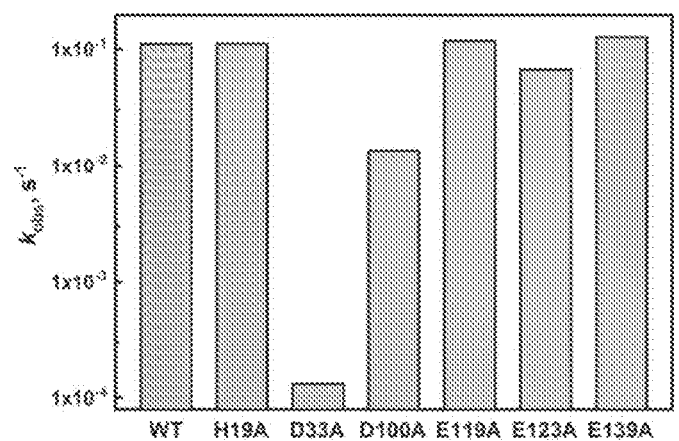
(FIG. 5F) The cleavage rate constant kobs values for Csm3 mutant variants of StCsm-40.
Figure 14A:
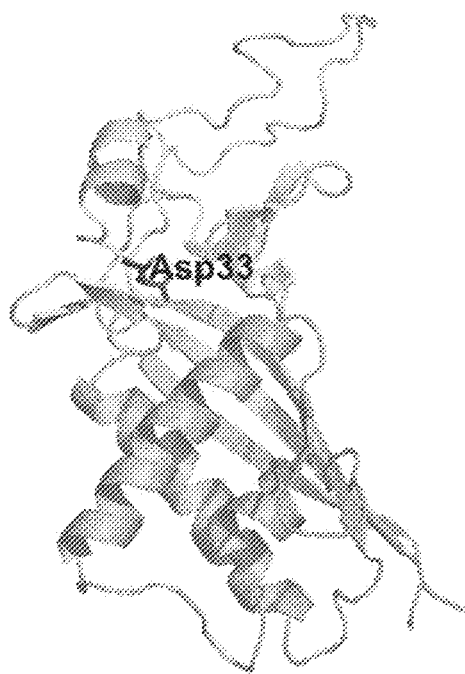
FIGS. 14A-D show computational analysis of Csm3.
Figure 14B:
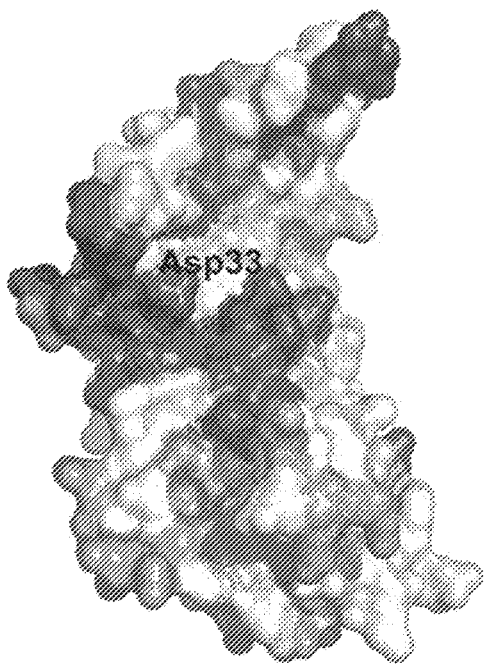
Figure 14C:
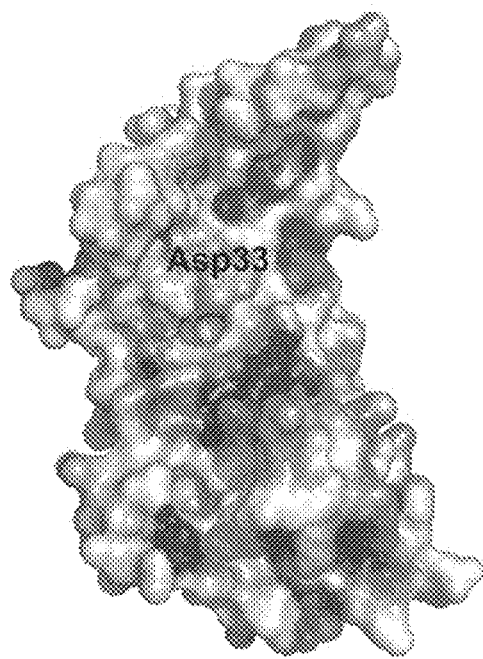

Regularly spaced cleavage pattern of the RNA target (FIGS. 2-4, 11-13) implies the presence of multiple cleavage modules in the Csm complex. According to the densitometric analysis, 3 Csm2 and 5 Csm3 subunits are identified in the Csm-40 complex, while 6 Csm2 and 10 Csm3 subunits are present in the Csm-72 complex. Multiple copies of the Csm2 and Csm3 proteins in the Csm complexes make them prime candidates for catalytic subunits. StCsm2 is a small (121 aa) α-helical protein of unknown structure. StCsm3 (220 aa) contain a conserved RRM core and is fairly closely related (~35% sequence identity) to *Methanopyrus kandleri* Csm3, whose crystal structure has been solved recently (Hrle et al., 2013). It was reasoned that, since the catalytic activity of the StCsm complex requires the presence of $Me^{2+}$ ions, the active site is likely to contain one or more acidic residues. Multiple sequence alignments of both Csm2 and Csm3 protein families were inspected for conserved aspartic or glutamic residues. No promising candidates in StCsm2 were found but several, including D33, D100, E119, E123, and E139 were identified in StCsm3 (FIG. 5A). To probe the role of these conserved negatively charged Csm3 residues, single residue alanine replacement mutants were constructed. The H19A mutant was also constructed, since it was shown that the corresponding mutation (R21A) in *M. kandleri* Csm3 abolished binding of single-stranded RNA (Hrle et al., 2013). Each mutant was expressed in the context of other StCsm/Cas proteins and analyzed the cleavage activity of the StCsm-40 complex containing mutant Csm3 subunits. StCsm3 H19A, D100A, E119A, E123A, and E139A mutants did not compromise the formation, RNA binding or cleavage activity of Csm-40 complex (FIG. 5B-5F). However, the D33A mutant impaired Csm-40 RNA cleavage (FIG. 5E-5F) without affecting RNA binding (FIG. 5D) or complex assembly. Taken together, these data demonstrate that Csm3 is an RNase, producing multiple cleavage patterns spaced by regular 6-nt intervals, and that the D33 residue is part of the catalytic/metal-chelating site. StCsm3 structural model based on the homologous structure of *M. kandleri* Csm3 is in good agreement with the identified role for this residue (FIG. 14A). D33 belongs to the highly conserved surface patch that extends from the RRM core into the "lid" subdomain (FIG. 14B). Part of this surface patch is positively charged, supporting the idea that it represents an RNA-binding site (FIG. 14C).

In Vivo RNA Targeting by the StCsm Complex

Figure 6A:
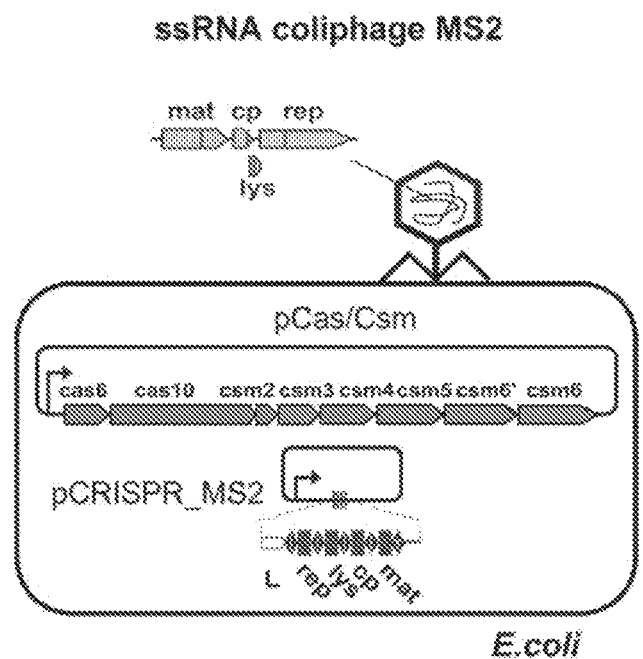
FIGS. 6A-B show restriction of ssRNA phage MS2 in *E. coli* cells expressing StCsm complex.
Figure 6B:
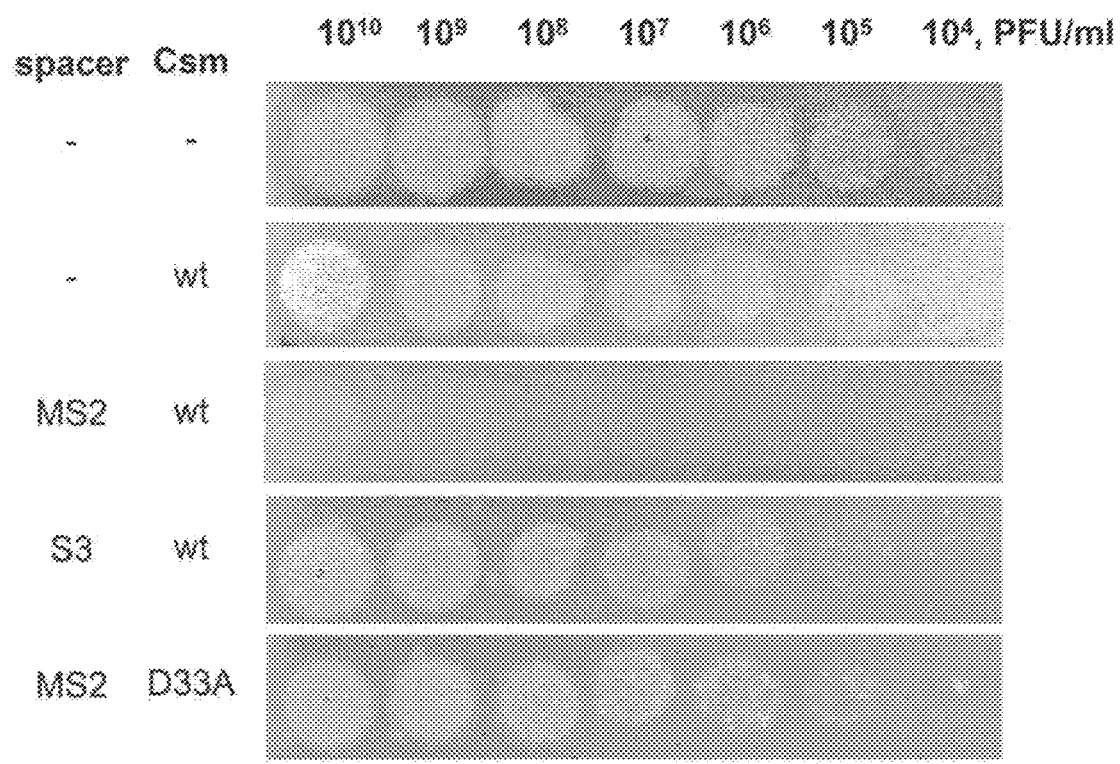

To test whether the StCsm complex can target RNA in vivo, the MS2 phage restriction assay was employed. MS2 is a lytic single-stranded RNA coliphage which infects *E. coli* via the fertility (F) pilus. The MS2 phage is a preferable model to investigate RNA targeting by the CRISPR-Cas system in vivo as no DNA intermediate is formed during the life cycle of this phage (Olsthoorn and van Duin, 2011). For in vivo RNA-targeting experiment, the *E. coli* NovaBlue (DE3, F$^+$) strain was transformed with two compatible plasmids: i) pCRISPR_MS2 plasmid bearing the synthetic CRISPR array of five repeats interspaced by four 36-nt spacers targeting correspondingly the mat, lys, cp, and rep MS2 RNA sequences, and ii) pCsm/Cas plasmid for the expression of Cas/Csm proteins (FIG. 6A). The phage-targeting and control *E. coli* strains were plated and infected with series of dilutions of MS2 using the drop plaque assay. The assay revealed that the *E. coli* strain expressing wt Csm and crRNAs that target MS2 induces a 3 to 4 Log reduction of the plaquing efficiency with respect to the control cells (FIG. 6). No resistance to the MS2 phage infection was observed in the strain expressing either the non-targeting crRNA or the cleavage-deficient (D33A) Csm3 mutant. Taken together these data demonstrate that the StCsm complex conveys in vivo resistance to RNA phage in the heterologous *E. coli* host.

This established the NA specificity and mechanism for the Type III-A CRISPR-Cas system of *Streptococcus thermophilus*. In sharp contrast to other CRISPR-Cas subtypes, the functional activity of Type III-A system so far has not been reconstituted in vitro. Cas/Csm proteins in the Type III-A CRISPR locus of the *S. thermophilus* DGCC8004 are homologous to those of *S. thermophilus* DGCC7710 and LMD-9. They also show more distant but significant similarities to Cas/Csm proteins of *L. lactis, E. italicus* and *S. epidermidis* (Marraffini and Sontheimer 2008, Millen et al. 2012) (FIG. 8).

Csm Complexes of *S. thermophilus*

Figure 7:
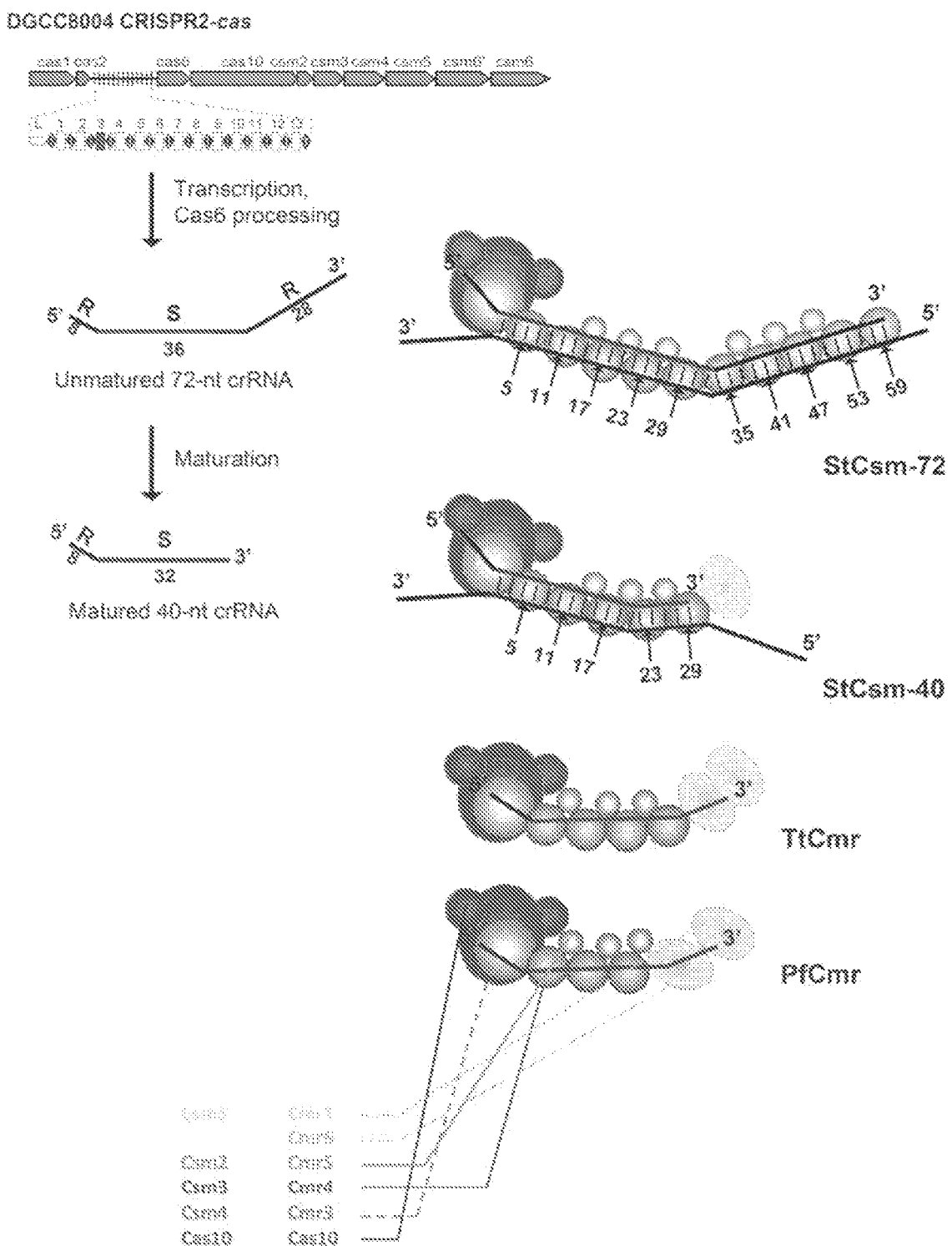
FIG. 7 shows structural and cleavage models of StCsm complexes. The CRISPR2 transcript is first processed into 72-nt crRNA intermediates that undergo further maturation into 40-nt crRNA. Both crRNAs are incorporated into StCsm complexes that target RNA but differ by the number of Csm3 and Csm2 subunits. The number of RNA cleavage products correlate with the number of Csm3 nuclease subunits. Schematic models of StCsm complexes were generated based on similarity to TtCmr and PfCmr. Csm analogs of Cmr proteins according to Makarova et al., 2011a are shaded the same, and as indicated.

The Type III-A CRISPR-Cas locus of the DGCC8004 was expressed in *E. coli* and two RNP complexes, termed Csm-40 and Csm-72, were isolated. Both complexes share a conserved set of Cas10, Csm2, Csm3 and Csm4 proteins. In addition to this core, the Csm-40 also contains the Csm5 protein. Two distinct crRNAs of 72- and 40-nt co-purify with Csm-40 and Csm-72 complexes isolated from the heterologous *E. coli* host. The 72-nt crRNA comprised of an 8-nt 5'-handle, a 36-nt spacer and a 28-nt 3'-handle would result from the pre-crRNA cleavage between 28 and 29 nt within the conserved repeat region presumably by the Cas6 nuclease, similar to the III-B CRISPR-Cas system (Carte et al., 2008). The shorter 40-nt crRNA co-purified with the Csm-40 complex of *S. thermophilus* contains the conserved 8-nt 5'-handle and 32-nt spacer indicating that the 72-nt crRNA intermediate undergoes further 3'-end processing to produce a mature 40-nt crRNA that lacks the 3'-handle and 4 nt within the spacer region (FIG. 7). The RNase involved in the maturation of 72 nt crRNA intermediate remains to be identified, however the Csm5 protein which is absent in Csm-72 but is present in Csm-40 could be a possible candidate. Indeed, csm5 gene deletion in DGCC8004 produces only unmatured Csm-72 complexes (data not shown).

The crRNA processing and maturation pathway in the *S. thermophilus* Type III-A system (FIG. 7) shows striking similarity to that in *S. epidermidis*. First, the SeCsm complex includes the same set of Cas10, Csm2, Csm3, Csm4 and Csm5 proteins as the StCsm-40. Furthermore, in *S. epidermidis*, the primary processing by Cas6 produces a 71-nt crRNA intermediate, that is subjected to further endonucleolytic processing at the 3' end (Hatoum-Aslan et al. 2011; Hatoum-Aslan et al. 2014).

StCsm Complex Cuts RNA Producing a Regular Cleavage Pattern

The Csm complexes of *S. epidermidis* and *S. solfataricus* have been reconstituted and isolated, however the NA cleavage activity has not been reported so far. In vivo studies in *S. epidermidis* suggested that the Type III-A SeCsm RNP complex targets DNA (Marraffini and Sontheimer, 2008) in a PAM-independent manner and prevents autoimmunity by checking the complementarity between the crRNA 5'-handle and the 3'-flanking sequence in the vicinity of the protospacer (Marraffini and Sontheimer, 2010). In contrast to these data, it was determined that the StCsm-40 and StCsm-72 complexes bind ssRNA with high affinity and cut a ssRNA target in a PAM-independent manner in the presence of Me$^{2+}$ ions, producing a regular 6-nt cleavage pattern in the protospacer region (FIGS. 2D and 11C-11E). In this respect the Type III-A StCsm complex resembles the RNA-targeting Type III-B Cmr-complexes PfCmr, SsCmr and TtCmr (Hale et al., 2009; Staals et al., 2013; Zhang et al., 2012) (FIG. 7) rather than DNA targeting Type I and II complexes. By targeting RNA rather than DNA, the StCsm complex avoids autoimmunity. It was demonstrated that the nucleotide context and non-complementarity outside the protospacer have no effect on the target RNA cleavage, demonstrating that PAM or unpaired flanking sequences of the protospacer are not required for cleavage by the StCsm (FIG. 13). The complementarity of the protospacer is the only pre-requisite for the StCsm cleavage: non-matching RNA is not cleaved; however, either two contiguous mismatches or end truncations in the complimentary protospacer S3 are tolerated (FIG. 13). The differences in the cleavage patterns of the 5'- and 3'-labeled RNAs (FIG. 2D) imply that cleavage first occurs at 3'-end of the target RNA. It remains to be established whether the observed cleavage pattern is dictated by the "seed" sequence (e.g. directionality of base pairing process between the crRNA and target RNA) or by nucleotide context-dependent differences of cleavage rate.

It was found that for the Csm-72 complex the target RNA is being cleaved at regular 6-nt intervals outside the protospacer if it retains base complementarity to the crRNA 3'-handle. Such regularly spaced cleavage pattern of the RNA target (FIGS. 2-4, 11 and 13) implies the presence of multiple cleavage modules in the Csm complex. The major difference between the Csm-40 and Csm-72 complexes is the number of Csm2 and Csm3 subunits. The Csm-40 contains 3 Csm2 and 5 Csm3 subunits while Csm-72 contains 6 Csm2 and 10 Csm3 subunits (FIG. 1D). The size of the complexes determined by SAXS correlates with the different stoichiometry of Csm-40 and Csm-72. Both complexes show a slightly twisted elongated shape but the Csm-72 is significantly more elongated than Csm-40 complex (FIG. 1H). Taken together these data suggest that the longer unmatured 72-nt crRNA intermediate in the Csm-72 complex binds additional copies of Csm2 and Csm3 subunits into a RNP filament (FIG. 7).

Csm3 is a RNase Subunit in the StCsm Complex

Computational analysis revealed that StCsm3 has a conserved RRM core and is fairly closely related (~35% sequence identity) to *M. kandleri* Csm3 (Hrle et al., 2013). StCsm3 displays close structural similarity to MkCsm3, in particular the RRM-core and insertions into RRM-core that form the "lid" subdomain (FIG. 14A). In contrast, StCsm3 lacks both the N-terminal zinc binding domain and the C-terminal helical domain, making its structure more compact compared to that of MkCsm3. Thus, StCsm3 may be considered as a trimmed-down version of MkCsm3. Guided by the multiple sequence alignment and homology model of StCsm3, candidate active site/metal chelating residues of Csm3 were selected and subjected to alanine mutagenesis. The highly conserved D33 residue of the StCsm3 was critical for the RNA cleavage activity of the Csm complex, demonstrating that Csm3 is an RNase in the StCsm and other Type III-A CRISPR-Cas systems (FIG. 5).

Implications for Other RNA-Targeting CRISPR Systems

Figure 14D:
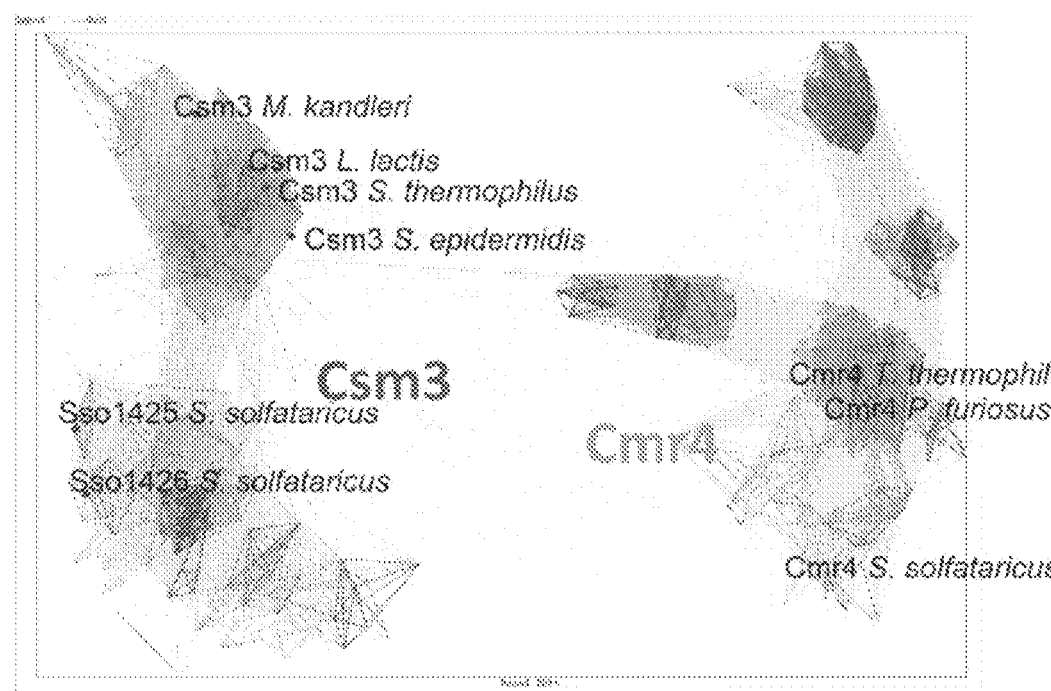

The StCsm complex was specific for RNA and cuts it in a PAM-independent manner producing a regular 6-nt cleavage pattern. The Csm3 protein, which is present in Csm-40 and Csm-72 complexes in multiple copies, was demonstrated to act as an RNase responsible for the target RNA cleavage. In this respect the Type III-A Csm complex of *S. thermophilus* closely resembles the RNA targeting Type III-B Cmr complex of *T. thermophilus* (TtCmr complex) that also produces a regular 6-nt cleavage pattern (Staals et al., 2013). The RNA degrading subunit in the Type III-B Cmr-module remains to be identified. Although there is currently no experimental evidence, Staals et al. suggested that Cmr4 could fulfill this role (Staals et al., 2013). Clustering of Csm3 and Cmr4 homologs by sequence similarity revealed that they form two related but separate groups (FIG. 14D). On the other hand, neither Csm3 nor Cmr4 families are homogenous. They are comprised of sequence clusters of various sizes. StCsm3 is a member of a large representative group of Csm3 homologs that includes those from *S. epidermidis, L. lactis* and *M. kandleri*. Another large, but more loosely connected group does not have proteins from experimentally characterized systems, except for the Csm complex from *S. solfataricus*. Sso1425 and Sso1426, two of its Csm3-like proteins (Makarova et al., 2011a), are members of this group albeit they are non-typical. The Cmr4 family appears even more heterogeneous than Csm3. Cmr4 proteins of experimentally characterized III-B systems from *T. thermophilus* and *P. furiosus* represent one of the larger clusters, while Cmr4 from *S. solfataricus* is a non-typical outlier. Biochemical characterization revealed that PfCmr and TtCmr RNA cleavage mechanism are similar and follow a 3'- or 5-' ruler mechanism, respectively (Hale et al., 2009; Staals et al., 2013). Meanwhile, SsCmr endonucleolytically cleaves both target RNA and crRNA at UA dinucleotides (Zhang et al., 2012). It thus would not be surprising if members of other, so far experimentally uncharacterized groups were part of Cmr complexes with somewhat different properties.

Whether Csm3 and Cmr4 proteins may have similarly organized active sites was questioned. The aligned sequences of Csm3 and Cmr4 subunits from characterized systems revealed that sequences of both families have Asp in the corresponding positions, suggesting similar active sites (FIG. 5A). The exception is Sso1426. This is surprising, considering the composition of the *S. solfataricus* Csm complex. Four copies of Sso1426 were found to be present within the complex suggesting that this subunit might play a role of the Csm3 (Rouillon et al., 2013). In contrast, another Csm3-like protein Sso1425 does have the D33 counterpart suggesting it can cleave ssRNA. However, only a single copy of Sso1425 was found in the *S. solfataricus* complex. Taken together, these data suggest that Csm-modules in *S. thermophilus* and *S. solfataricus* have different architectures and RNA cleavage mechanisms.

It is demonstrated for the first time that the Csm effector complex of the *S. thermophilus* Type W-A system targets RNA and establish the mechanism of RNA cleavage. It is demonstrated that in the Type III-A effector complex Cas/Csm proteins assemble into an RNP filament (FIG. 7) that contains multiple copies of Csm2 and Csm3 proteins. The inventors provided evidence that the Csm3 subunit acts as an RNase that cleaves target RNA at multiple sites spaced by regular 6-nt intervals (FIG. 7). The number of cleavage sites correlates with the number of Csm3 subunits in the Csm effector complex. Ease of programmability of the Type III-A StCsm complex by custom crRNAs (FIG. 12) permits the development of novel molecular tools for RNA interference.

RNA cleavage specificity established here for the StCsm complex in vitro is supported by in vivo experiments of MS2 RNA phage interference in the heterologous *E. coli* host (FIG. 6). It remains to be established whether RNA silencing by the StCsm complex can contribute to the DNA phage interference in the *S. thermophilus* host. Transcription-dependent DNA targeting mechanism has been proposed recently for the Type III-B CRISPR-Cmr system (Deng et al., 2013); however, it has yet to be demonstrated for *S. thermophilus* and other Type III-A systems.

Deletion Analysis of StCsm Complex

Csm-complexes are composed of several Cas proteins (Cas10, Csm2, Csm3, Csm4, Csm5) and contain traces of Cas6. In the StCsm complexes Csm3 acts as the ribonuclease that cuts target RNA. Cas6 is responsible for the pre-crRNA maturation into 72 nt crRNAs. To establish a functional role of other Csm proteins, pCas/Csm plasmid variants with disrupted individual cas/csm genes were engineered and a set of StCsm deletion mutant complexes was isolated. These StCsm deletion mutant complexes were then subjected to biochemical analyses to determine the role of each individual protein in the StCsm complex assembly and RNA cleavage.

Figures 17A, 17C:
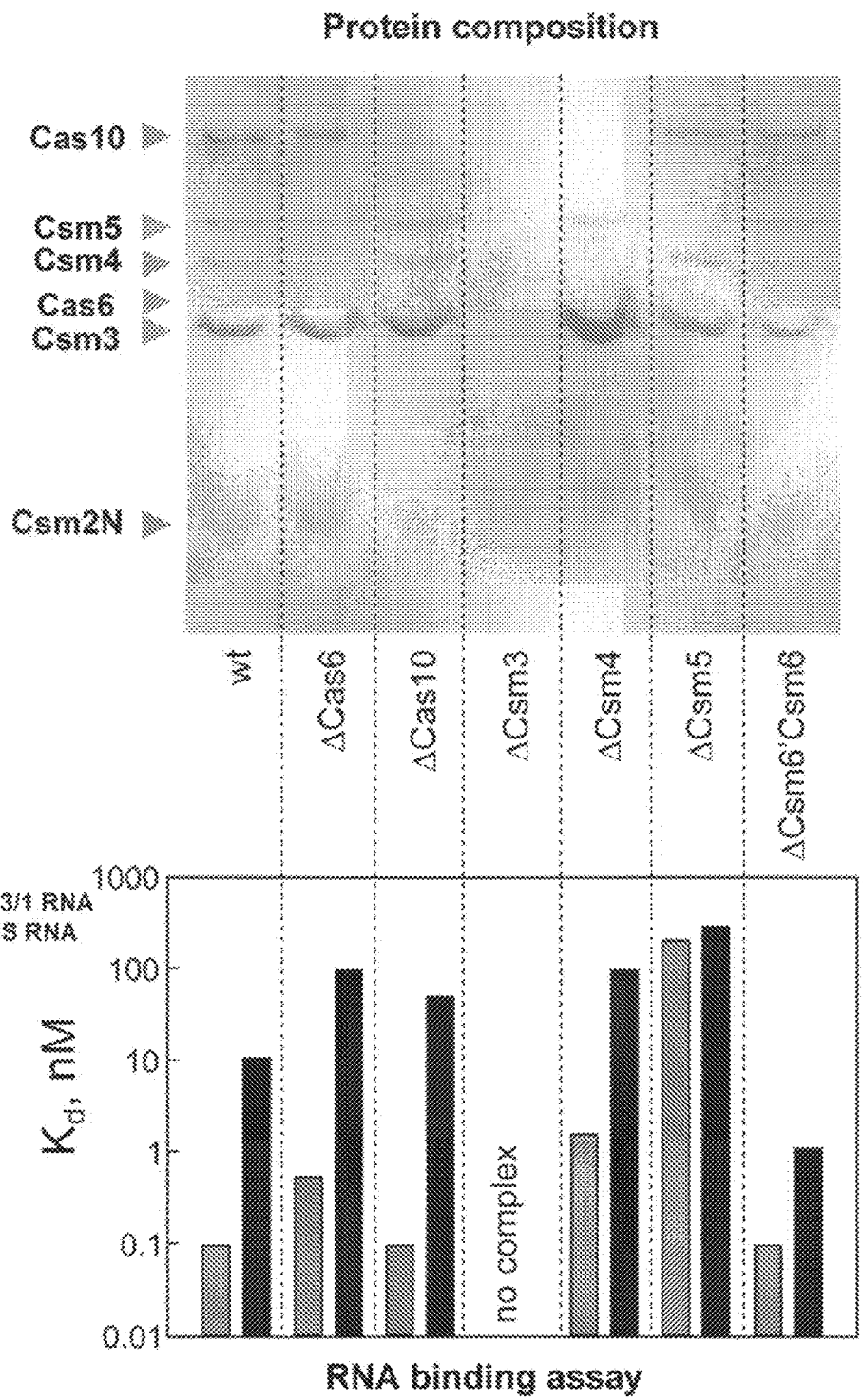
FIGS. 17A, 17B, 17C and 17D show protein compositions and cleavage in vitro cleavage activity of deletion mutants of StCsm-40 complex. Single-gene deletion variants of pCas/Csm plasmid were generated by disrupting individual cas genes by deletions or frameshift mutations. Escherichia coli BL21(DE3) cells were transformed with a corresponding deletion mutant variant of pCas/Csm, pCRISPR_S3, and pCsm2-Tag plasmids. The deletion mutants of StCsm-40 complex were isolated from such cells by Strep-chelating affinity and size exclusion chromatography.
Figure 17B:
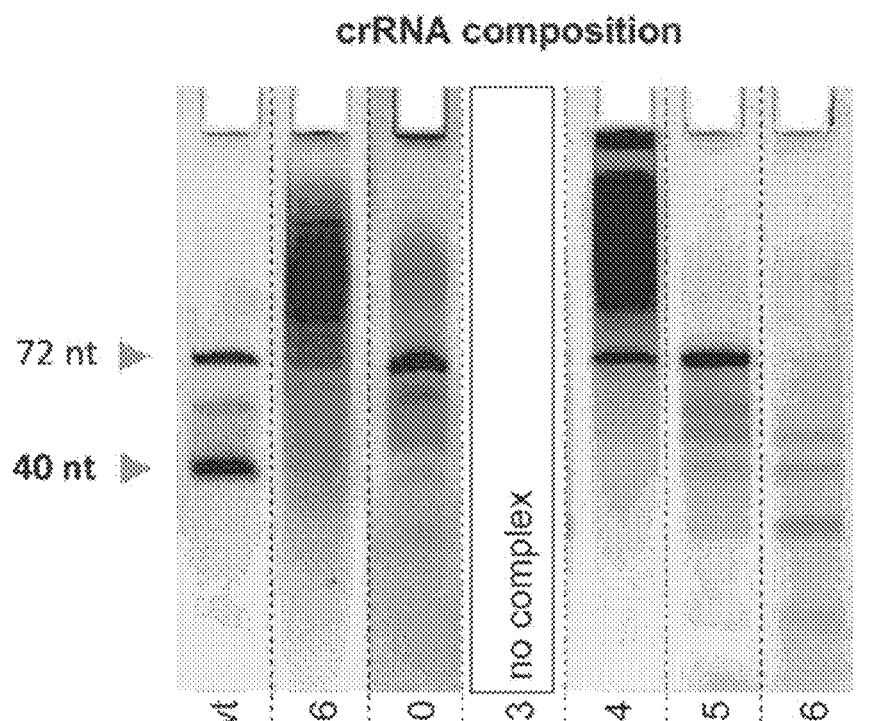
Figure 18A:
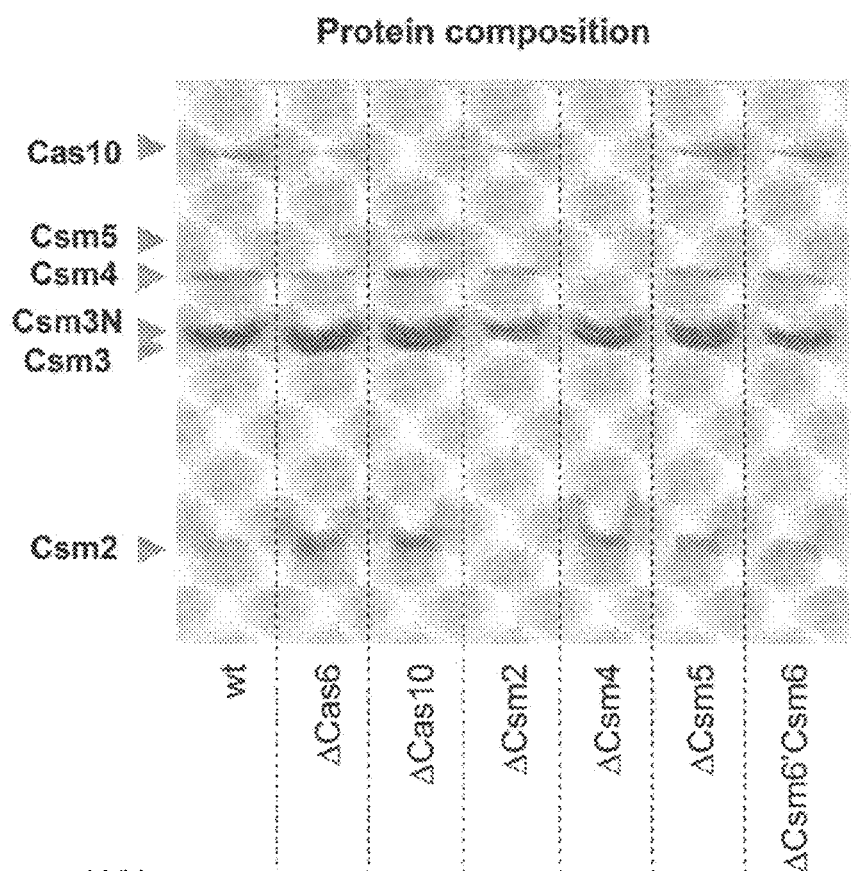

The composition of proteins and crRNAs in the StCsm complex deletion mutants were determined. SDS-PAGE analysis of protein composition of the purified StCsm-40 and StCsm-72 deletion mutants confirmed that in all cases protein corresponding to the disrupted cas gene is missing in the complex (FIG. 17A, FIG. 18A). Csm3 makes a backbone of StCsm complex since no complex is detected when csm3 gene is deleted. Cas10 seems to be associated to the Csm4 in the Csm-complex since Cas10 subunit is missing in the StCsm-40ΔCsm4 and StCsm-72ΔCsm4 samples.

crRNAs co-purified with deletion mutant complexes are distinct (FIG. 17B, FIG. 18B). Nucleic acids purified from StCsm-40ΔCas6 and StCsm-72ΔCas6 complexes pre-dominantly contain long pre-crRNAs that support Cas6 function in crRNA maturation. In the case of StCsmΔCsm4 variant 72 nt crRNA co-purifies together with long pre-crRNA molecules implying that crRNA binding specificity is compromised. Wt StCsm-40 and StCsm-40ΔCsm6'ΔCsm6 predominantly contains 40 nt crRNAs, while in all other cases 72 nt prevails in the Csm-complex. Taken together, available data suggest that Cas10, Csm5 and possibly Csm2 and Csm4 proteins are important for crRNA maturation from 72 to 40 nt species.

Figure 17D:
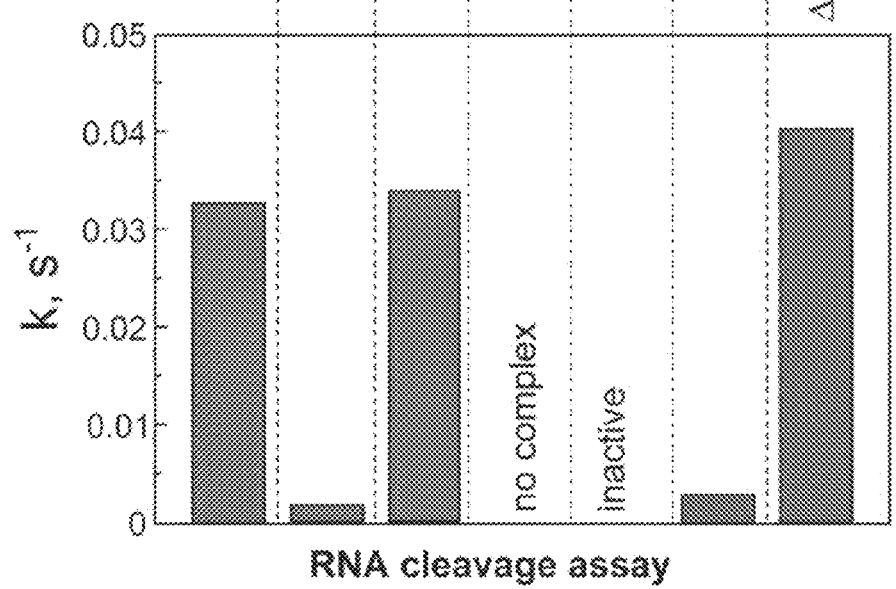
Figure 18C:
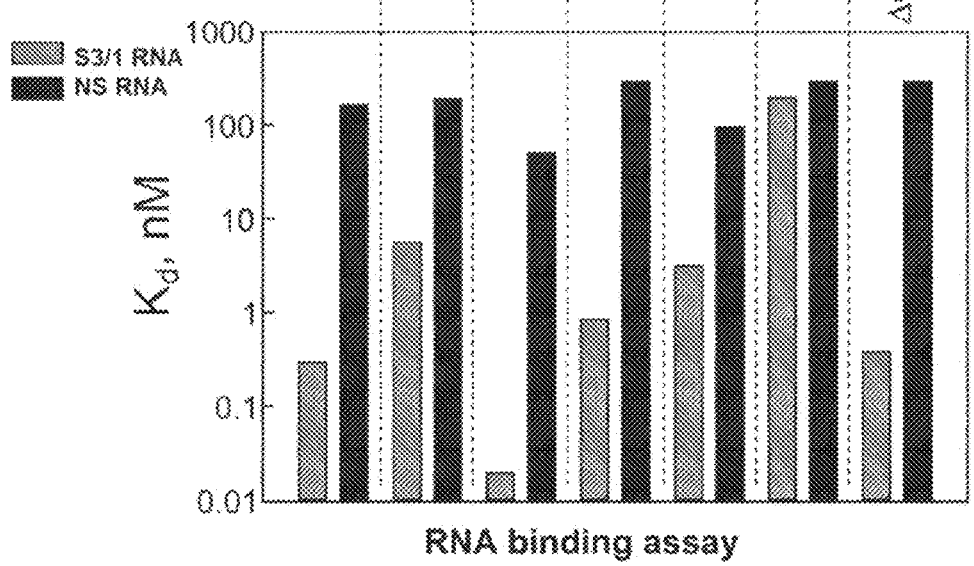
Figure 20:
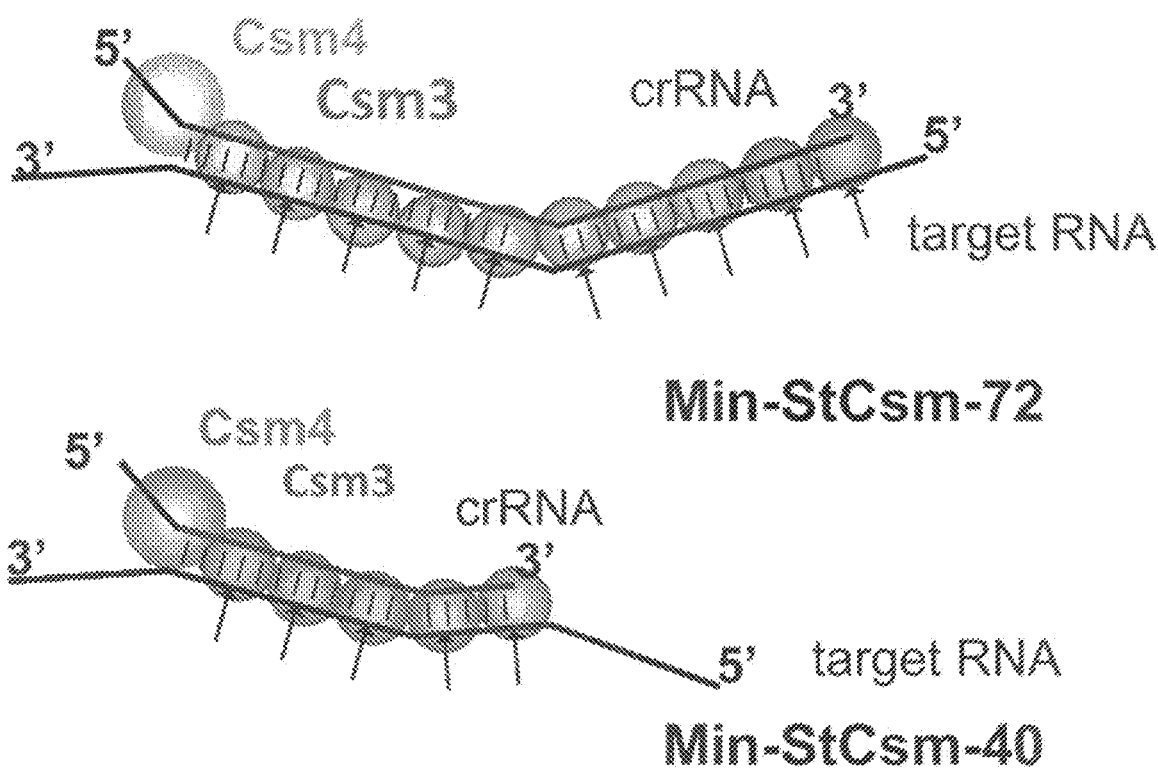
FIG. 20 shows structural and cleavage model of minimal StCsm complex variants. The minimal catalytically active StCsm complex contains Csm3 and Csm4 proteins and crRNA molecule. The 5'-handle of crRNA is recognized by the Csm4 subunit. Csm3 is endoribonuclease that cuts target RNA. The difference in the number of RNA cleavage positions suggests the different number of Csm3 subunits in the complexes.

The impact of single protein deletions on the StCsm complex capability to bind and cleave RNA was next evaluated. StCsm complex deletion mutants were probed on target substrates complementary to the crRNA encoded by the spacer S3 and non-targeting RNA substrates (FIG. 17C, FIG. 18C). Csm5 deletion dramatically impacts specific RNA binding: StCsmΔCsm5 complexes bind target and non-target RNAs with nearly the same affinity while wt StCsm complexes show ~100-fold tighter binding to the target RNA. To compare the RNA cleavage capabilities of the StCsm complex variants, we performed cleavage assays and determined cleavage rate constants (FIG. 17D, FIG. 18D). Surprisingly, most of the StCsm complex deletion mutants retained at least partial RNA cleavage activity. Only for StCsmΔCas6 and StCsmΔCsm4 complexes RNA cleavage activity was nearly fully abolished. In all other cases, the reaction products (and hence cleavage positions) were identical. The cleavage activity of StCsmΔCsm6'ΔCsm6 variants is similar to that of wt. This is not surprising since Csm6' and Csm6 proteins are not present in the StCsm complex. Cas10 significantly impacted only the yield of the complex but had no effect on the cleavage rate. The RNA cleavage assay data suggests that only Csm3, Csm4, and crRNA-generating Cas6 are required for the target RNA cleavage. Csm2 is completely dispensable in respect to RNA cleavage.

Minimal StCsm Complex Assembly

Deletion analysis shows that Csm3 and Csm4 proteins are critical for Csm-complex assembly/activity. Therefore, the possibility to assemble a minimal Csm-complex arranged of three components including Csm3 and Csm4 subunits, and crRNA was explored. Such minimal engineered variant StCsm would be a convenient tool for specific RNA targeting both in vitro and in vivo. The csm3 and csm4 genes were cloned into pCDFDuet-1 vector and added a StrepII-Tag sequence to the N-terminal part of csm3 to obtain $p^{Tag}$Csm3_Csm4 plasmid. $p^{Tag}$Cas10 plasmid was constructed by cloning cas10 gene into pETDuet-1 vector. pCas6 plasmid was constructed by cloning cash gene into pCOLADuet-1 vector. The expression of Cas6 protein together with pCRISPR_S3 (encoding the S3 CRISPR region) would generate unmatured 72-nt crRNA which would be incorporated in Csm ribonucleoprotein complex. Alternatively, to omit Cas6-mediated pre-crRNA maturation, plasmids pcrRNA-40 and pcrRNA-72 were constructed. Transcription of these plasmids in E. coli will produce 40-nt or 72-nt crRNA species in the absence of Cas6. These plasmids were engineered on the basis of pACYCDuet-1 vector with under a control of the BBa J23119 promoter. $p^{Tag}$Csm3_Csm4 was co-expressed in E. coli BL21(DE3) either with pCas6 and pCRISPR plasmids or with pcrRNA-40/pcrRNA-72 plasmids. Since omitting Cas10 proved to significantly reduce yields of the complex during the deletion analysis, how the presence or absence of $p^{Tag}$Cas10 in the expression system would affect the minimal Csm-complexes was also tested. Affinity purification on the Strep-chelating column yielded minimal Csm complexes, containing Csm3 and Csm4 protein subunits and crRNA. When $p^{Tag}$Cas10 plasmid was present in the expression system, the complexes also contained Cas10 protein and the total yield of the complexes was significantly increased. When pCas6 plasmid was present in the expression system, Cas6 protein co-purified with the Csm-complex. The RNA cleavage activity of these RNP complexes was assayed on the 68-nt S3/4 or 86-nt S3/6 RNA target substrate (FIG. 19). Minimal Csm-complexes containing only Csm3 and Csm4 subunits, as well as other minimized Csm-complex variants, show RNA cleavage pattern, characteristic to the wt StCsm-72 complex. Taken together, data provided here show that minimal Csm complex assembled using only Csm3, Csm4, and crRNA cleaves target RNA. In this respect, it provides a versatile tool for RNA knock-outs in the cell. Cleavage deficient variant of the minimal complex could be used for RNA knock-downs or pull-down of the desired target RNA from cells.

Experimental Procedures

Expression and Isolation of Csm Complexes

The sequence of CRISPR2-cas locus of S. thermophilus DGCC8004 was deposited in GenBank (accession number KM222358). Heterologous E. coli BL21(DE3) cells producing the Strep-tagged Csm complexes were engineered and cultivated as described. Csm-40 and Csm-72 complexes were isolated by subsequent Strep-chelating affinity and size exclusion chromatography steps.

Streptococcus thermophilus DGCC8004 was cultivated at 42° C. in MI 7 broth (Oxoid) supplemented with 0.5% (w/v) lactose. Chromosomal DNA was extracted and purified using GeneJET Genomic DNA Purification Kit (Thermo Scientific). CRISPR2-Cas region was amplified by polymerase chain reaction (PCR) and sequenced using primers designed by genomic comparison with S. thermophilus DGCC7710 (GenBank accession number AWVZ01000003). Annotation of the predicted ORFs was performed using BLASTP at NCBI (http://blast.ncbi.nlm-.nih.gov/Blast.cgi). CRISPR region was identified through repeat sequence similarity to that of S. thermophilus DGCC7710. Multiple sequence alignments of cas/csm genes, spacers and repeats sequences were carried out with ClustalW2 (http://www.ebi.ac.uk). Genomic DNA isolated from S. thermophilus DGCC8004 strain was used as the template for PCR amplification of the cas/csm genes. DNA fragment covering the 8.5 kb cas6-cas10-csm2-csm3-csm4-csm5-csm6-csm6' gene cassette was cloned into pCDF-Duet-1 expression vector via NcoI and AvrII restriction sites in two separate subcloning steps to generate plasmid pCas/Csm. Individual cas/csm genes were cloned into pETDuet-1_N-StrepII and pETDuet-1_C-StrepII expression vectors, except of cas10 (which was cloned into pBAD24 C-His-StrepII-His) and csm6 or csm6' (that were cloned into pBAD24 N-His-StrepII-His) to generate pCsmX-Tag and pCasY-Tag plasmids, where X=2, 3, 4, 5, 6, 6' and Y=6, 10. A synthetic 445-nt CRISPR locus containing five 36-nt length repeats interspersed by four identical 36-nt spacers S3 of the S. thermophilus DGCC8004 CRISPR2 system was obtained from Invitrogen and cloned into the pACYC-Duet-1 vector to generate a plasmid pCRISPR S3. Four copies of the spacer S3 have been engineered into the pCRISPR_S3 plasmid to increase the yield of the Csm-crRNA complex. Full sequencing of cloned DNA fragments confirmed their identity to the original sequences.

All three plasmids were co-expressed in *Escherichia coli* BL21 (DE3) grown at 37° C. in LB medium supplemented with streptomycin (25 µg/µl), ampicilin (50 µg/µl), and chloramphenicol (30 µg/µl). The fresh LB medium was inoculated with an overnight culture (1/20 (v/v)), and bacteria were grown to the mid-log phase ($OD_{600\ nm}$ 0.5 to 0.7), then 1 mM IPTG (and 0.2% (w/v) L-(+)-arabinose in case of Cast 0, Csm6 and Csm6') was added and cell suspension was further cultured for another 4 h. Harvested cells were resuspended in a Chromatography buffer (20 mM Tris-HCl (pH 8.5), 0.5 M NaCl, 7 mM 2-mercaptoethanol, 1 mM EDTA) supplemented with 0.1 mM phenylmethylsulfonyl fluoride (PMSF), and disrupted by sonication. Cell debris was removed by centrifugation. Csm complexes were captured on the StrepTrap affinity column (GE Healthcare) and further subjected to the Superdex 200 size exclusion chromatography (prep grade XK 16/60; GE Healthcare). SDS-PAGE of individual Strep-tagged Csm2, Csm3, Csm4, CsmS, Cas6 and Cas10 proteins isolated by affinity chromatography from *E. coli* lysates revealed co-purification of other Csm/Cas proteins suggesting the presence of a Csm complex. The abundance of the Csm complex co-purified via the Csm4-, CsmS-, Cas6- and Cas10-Strep tagged subunits was very low, and no complex was pull-downed via Csm6 or Csm6' subunits (data not shown). Therefore, Csm complexes isolated via N-terminus Strep-tagged Csm2 (Csm2 StrepN) and the N-terminus Strep-tagged Csm3 proteins (Csm3_StrepN) were subjected to further characterization. Individual Csm3-N-Strep protein was purified using StrepTrap affinity column. Csm3-N-Strep and Csm complexes eluted from the columns were dialysed against 10 mM Tris-HCl (pH 8.5) buffer containing 300 mM NaCl, 1 mM DTT, 0.1 mM EDTA, and 50% (v/v) glycerol, and stored at −20° C.

The composition of the isolated Csm-40 and Csm-72 complexes was analysed by SDS-PAGE and the sequence of Csm proteins was further confirmed by the mass spectrometry of tryptic digests. In order to estimate the stoichiometry of Csm complexes, protein bands in SDS-PAGE were quantified by densitometric analysis taking a count the different staining of Cas/Csm proteins. The molecular weights of the Csm complexes were estimated by dynamic light scattering (DLS) using Zetasizer µV (Malvern) and respective software. For DLS analysis Csm-40 and Csm-72 samples were analysed in a Chromatography buffer at 0.36 mg/ml and 0.6 mg/ml concentrations, respectively. Csm complex concentrations were estimated by Pierce 660 nm Protein Assay (Thermo Scientific) using bovine serum albumin (BSA) as a reference protein. Conversion to molar concentration was performed assuming that the Csm-72 stoichiometry is $Cas10_1{:}Csm2_6{:}Csm3_{10}{:}Csm4_1{:}crRNA72_1$ and the Csm-40 stoichiometry is $Cas10_1{:}Csm2_3{:}Csm3_5{:}Csm4_1{:}Csm5_1{:}crRNA40_1$.

Bioinformatic Analysis and Mutagenesis of Csm3

Putative active site residues of Csm3 were identified from multiple alignment of Csm3/Cmr4. Csm3 mutants were constructed using quick change mutagenesis and purified as described.

Mutagenesis of Csm3

The Csm3 mutants H19A, D33A, D100A, El 19A, E123A and E139A were obtained by the Quick Change Mutagenesis (QCM) Protocol (Zheng et al., 2004). First, a 3.0 kb DNA fragment containing csm2 and csm3 genes was subcloned from pCas/Csm plasmid into the pUC18 vector pre-cleaved with Sphl and Kpnl. The resulting plasmid pUC18_Csm2_Csm3 was used for Csm3 QCM mutagenesis. After QCM, the same fragment containing mutated versions of the Csm3 gene was transferred back into the pCas/Csm vector using Ndel and Spel sites, reconstituting the gene cassette. Sequencing of the entire cloned DNA fragment for each mutant confirmed that only the designed mutation had been introduced. Csm-40 complexes containing Csm3 mutants were isolated following the procedures described for the wt StCsm-40 (see above). D100A mutant StCsm-40 was purified only using the affinity chromatography.

Extraction, HPLC Purification and ESI-MS Analysis of crRNA

NAs co-purified with Csm-40 and Csm-72 were isolated using phenol:chloroform:isoamylalcohol (25:24:1, v/v/v) extraction and precipitated with isopropanol. Purified NAs were incubated with 0.8 U DNase I or 8 U RNase I (Thermo Scientific) for 30 min at 37° C. NAs were separated on a denaturing 15% polyacrylamide gel (PAAG) and visualized by SybrGold (Invitrogen) staining.

Ion-pair reversed-phased-HPLC purified crRNA architecture was determined using denaturing RNA chromatography in conjunction with electrospray ionization mass spectrometry (ESI-MS) as described in (Sinkunas et al., 2013).

All samples were analyzed by ion-pair reversed-phased-HPLC (Dickman and Homby, 2006; Waghmare et al., 2009) on an Agilent 1100 HPLC with UV260 nm detector (Agilent) using a DNAsep column 50 mm×4.6 mm I. D. (Transgenomic). The chromatographic analysis was performed using the following buffer conditions: A) 0.1 M triethylammonium acetate (TEAA) (pH 7.0) (Fluka); B) buffer A with 25% LC MS grade acetonitrile (v/v) (Fisher). The crRNA was obtained by injecting purified intact Csm-40 or Csm-72 at 75° C. using a linear gradient starting at 15% buffer B and extending to 60% B in 12.5 mM, followed by a linear extension to 100% B over 2 mM at a flow rate of 1.0 ml/min. Analysis of the 3' terminus was performed by incubating the HPLC-purified crRNA in a final concentration of 0.1 M HCl at 4° C. for 1 hour. The samples were concentrated to 10-20 µl on a vacuum concentrator (Eppendorf) prior to ESI-MS analysis.

ESI-MS Analysis of crRNA

Electrospray Ionization Mass spectrometry (ESI-MS) was performed in negative mode using an Amazon Ion Trap mass spectrometer (Bruker Daltonics), coupled to an online capillary liquid chromatography system (Ultimate 3000, Dionex, UK). RNA separations were performed using a monolithic (PS-DVB) capillary column (50 mm×0.2 mm I.D., Dionex, UK). The chromatography was performed using the following buffer conditions: C) 0.4 M 1,1,1,3,3,3,-Hexafluoro-2-propanol (HFIP, Sigma-Aldrich) adjusted with triethylamine (TEA) to pH 7.0 and 0.1 mM TEAA, and D) buffer C with 50% methanol (v/v) (Fisher). RNA analysis was performed at 50° C. with 20% buffer D, extending to 40% D in 5 min followed by a linear extension to 60% D over 8 min at a flow rate of 2 µl/min, 250 ng crRNA was digested with 1U RNase A/T1 (Applied Biosystems). The reaction was incubated at 37° C. for 4 h. The oligoribonucleotide mixture was separated on a PepMap C-18 RP capillary column (150 mm×0.3 gm I.D., Dionex, UK) at 50° C. using gradient conditions starting at 20% buffer C and extending to 35% D in 3 mins, followed by a linear extension to 60% D over 40 mins at a flow rate of 2 μl/min. The mass spectrometer was operated in negative mode, a capillary voltage was set at −2500 V to maintain capillary current between 30-50 nA, temperature of nitrogen 120° C. at a flow rate of 4.0 L/h and N2 nebuliser gas pressure at 0.4 bar. A mass range of 500-2500 m/z was set. Oligoribonucleotides with −2 to −4 charge states were selected for tandem mass spectrometry using collision induced dissociation.

Small Angle X-Ray Scattering (SAXS) Experiments

SAXS data for Csm-40 and Csm-72 were collected at P12 EMBL beam-line at PETRAIII storage ring of DESY synchrotron in Hamburg (Germany). Csm-40 and Csm-72 complexes were measured in 3 different concentrations in buffer containing 20 mM Tris-HCl (pH 8.5 at 25° C.), 0.5 M NaCl, 1 mM EDTA and 7 mM 2-mercaptoethanol. Data collection, processing and ab initio shape modeling details are presented in Table 4 and FIG. 10.

Ab initio shape modeling of both complexes was performed with the samples having highest concentration (1.3 mg/ml for Csm-40 and 2.0 mg/ml for Csm-72). Unprocessed scattering data with subtracted buffer scattering, Guinier plots of the lows region of the scattering curves used for the shape determination and P(r) functions of the highest concentration samples of Csm-40 and Csm-72 are presented in FIG. 10. Two-dimensional scattering curves were transformed and distance distribution functions P(r) were calculated using GNOM (Svergun, 1992). At this stage data were truncated to s values 0.15-0.1 $A^{-1}$ and calculated distance distribution function was used for following ab initio modeling. 10 independent bead models for both complexes were generated using DAMMIN (Svergun, 1999). These models were aligned, filtered and averaged based on occupancy using DAMAVER (Volkov and Svergun, 2003). The averaged NSD of superposition of DAMMIN models of Csm-40 complex was 0.563±0.028 (for Csm-72 models averaged NSD is 0.575±0.019), no model was rejected in both cases.

The inertia tensor was calculated for averaged models of both complexes and models were aligned along the largest principal axis so as the end points of both models coincided. After that the protruding part of the longer Csm-72 complex was truncated. Csm-40 model was aligned with truncated Csm-72 models by automatic procedure SUPCOMB (Kozin and Svergun, 2001) producing an NSD value. Then Csm-40 model was shifted along the principal axis of Csm-72 model by the fixed step (5 or 10 A) and again Csm-40 model was aligned by SUPCOMB with the Csm-72 model after truncation of protruding parts. Thus the Csm-40 model was sequentially shifted along the principal axis of Csm-72 model and the best superposition showed the lower NSD value (S. Grazulis, personal communication). MOLSCRIPT (Kraulis, 1991) and RASTER3D (Merritt and Bacon, 1997) programs were used for SAXS models presented in FIGS. 1 and 10.

DNA and RNA Substrates

Synthetic oligodeoxynucleotides were purchased from Metabion. All RNA substrates were obtained by in vitro transcription using TranscriptAid T7 High Yield Transcription Kit (Thermo Scientific). A full description of all the DNA and RNA substrates is provided in the Table 5. DNA and RNA substrates were either 5'-labeled with [$\gamma^{32}$P] ATP and PNK or 3'-labeled with [$\alpha^{32}$P] cordycepin-5'-triphosphate (PerkinElmer) and poly(A) polymerase (Life Technologies) followed by denaturing gel purification.

To assemble DNA oligoduplexes, complementary oligodeoxynucleotides were mixed at 1:1 molar ratio in the Reaction buffer (33 mM Tris-acetate (pH 7.9 at 25° C.), 66 mM potassium acetate), heated to 90° C. and slowly allowed to cool to room temperature.

For generation of S3/1-10, S3/14 RNA substrates, first pUC18 plasmids pUC18_53/1 and pUC18_53/2, bearing S3/1 or S3/2 sequences were constructed. For this purpose, annealed synthetic DNA oligoduplexes S3/1 or S3/2 were ligated into pUC18 plasmid pre-cleaved with SmaI. Engineered plasmids pUC18_S3/1 and pUC18_S3/2 were sequenced to persuade that only copy of DNA duplex was ligated into the vector. Further these plasmids were used as a template to produce different DNA fragments by PCR using appropriate primers containing a T7 promoter in front of the desired RNA sequence. Purified PCR products were used in the in vitro transcription reaction to obtain RNA substrates. S3/11-13 RNAs were prepared by hybridizing two complementary DNA oligonucleotides, containing a T7 promoter in front of the desired RNA sequence followed by in vitro transcription.

DNA/RNA hybrids were assembled in similar manner annealing complementary oligodeoxynucleotide to RNA obtained by in vitro transcription.

pBR322 plasmid bearing the Tc gene, encoding tetracycline (Tc) resistance protein, was used to produce Tc RNA and ncTc RNA substrates using the same in vitro transcription reaction as described above for S3/1-10, S3/14. Prior to $^{32}$P 5'-labeling RNA substrates were dephosphorylated using FastAP thermosensitive alkaline phosphatase (Thermo Scientific).

Electrophoretic Mobility Shift Assay

Binding assays were performed by incubating different amounts of Csm complexes with 0.5 nM of $^{32}$P-5'-labeled NA in the Binding buffer (40 mM Tris, 20 mM acetic acid (pH 8.4 at 25° C.), 1 mM EDTA, 0.1 mg/ml BSA, 10% (v/v) glycerol). All reactions were incubated for 15 min at room temperature prior to electrophoresis on native 8% (w/v) PAAG. Electrophoresis was carried out at room temperature for 3 h at 6 V/cm using 40 mM Tris, 20 mM acetic acid (pH 8.4 at 25° C.), 0.1 mM EDTA as the running buffer. Gels were dried and visualized using a FLA-5100 phosphorimager (Fujifilm). The $K_d$ for NA binding by Csm-72 and Csm-40 was evaluated assuming the complex concentration at which half of the substrate is bound as a rough estimate of $K_d$ value. For binding competition assay 0.5 nM $^{32}$P-labelled S3/1 RNA was mixed with 0.5-5000 nM of unlabeled competitor NA and 0.3 nM StCsm-40, and analyzed by EMSA.

Cleavage Assay

The Csm-40 reactions were performed at 25° C. and contained 20 nM of 5'- or 3'-radiolabeled NA (Table 5) and 62.5 nM (unless stated otherwise) complex in the Reaction buffer (33 mM Tris-acetate (pH 7.9 at 25° C.), 66 mM K-acetate, 0.1 mg/ml BSA and 10 mM Mg-acetate). Csm-72 reactions were performed in the same Reaction buffer at 37° C. and contained 20 nM of radiolabeled NA and 125 nM of complex unless stated otherwise. Cleavage reactions using minimal StCsm were performed in the same Reaction buffer at 37° C. and contained 4 nM of radiolabeled RNA and ~15 ng/μl of the RNP complex. Reactions were initiated by addition of the Csm complex. The samples were collected at timed intervals and quenched by mixing 10 μl of reaction mixture with 2×RNA loading buffer (Thermo Scientific) followed by incubation for 10 min at 85° C. The reaction products were separated on a denaturing 20% PAAG and visualized by autoradiography. $^{32}$P-5'-labeled RNA Decade marker (Ambion) was used as size marker. To map the cleavage products oligoribonucleotide markers were generated by RNase A (Thermo Scientific, final concentration 10 ng/ml) treatment of RNA substrates for 8 min at 22° C. or by alkaline hydrolysis in 50 mM NaHCO$_3$ (pH 9.5) at 95° C. for 5 min.

Fluorescent Microscopy

Transformed E. coli cells producing GFP and StCsm were diluted 1:40 from an overnight culture in fresh LB medium and cells were further grown at 37° C. for 2 h in the presence of 1% IPTG to induce Cas/Csm, GFP and crRNA expression. The GFP transcript degradation was monitored by inspecting GFP fluorescence in E. coli cells. For this purpose, an aliquot of bacteria (2 μl) was immediately mounted on a thin film of 1.2% agarose (Thermofisher Scientific) on microscope slides and then overlaid with a coverslip (Roth). The cells were immediately imaged by contrast and fluorescence microscopy. Acquisition of contrast and fluorescence images was performed using a Nicon Elipse Ti-U microscope coupled to a Nicon DS-Qi1 camera. The digital images were analyzed with NIS Element v.4.00.00 (Nicon) software. No electronic enhancement or manipulation was applied to the images.

Phage Drop Plaque Assay

Phage drop plaque assay was conducted using LGC Standards recommendations. Phage drop plaque assay was conducted using LGC Standards recommendations. Briefly, E. coli NovaBlue(DE3) [(endA 1 hsdR17(r$_{K12-}$ m$_{K12+}$) supE44 thi-1 recAl gyrA96 relAl lac (DE3) FlproA$^+$B$^+$ lad q ZΔM15::Tn10] (Tet$^R$)] was transformed with wt pCas/Csm (Str$^R$) or D33A Csm3 pCas/Csm (Str$^R$) and pCRISPR_MS2 (Cm$^R$), pCRISPR_S3 (Cm$^R$), or pACYC-Duet-1 (Cm$^R$). E. coli cells bearing different sets of plasmids were grown in LB medium with appropriate antibiotics at 37° C. to an OD 600 of 0.9 and a 0.4 ml aliquot of bacterial culture was mixed with melted 0.5% soft nutrient agar (45° C.). This mixture was poured onto 1.5% solid agar to make double layer agar plates. Both layers of agar contained appropriate antibiotics, 0.1 mM IPTG, 0.1% glucose, 2 mM CaCl$_2$ and 0.01 mg/ml thiamine. When the top agar hardened, phage stock (5 μl) from a dilution series was delivered on each plate with the bacteria. The plates were examined for cell lysis after overnight incubations at 37° C. NovaBlue(DE3) was used as the indicator for determining the phage titer. pCRISPR_MS2 plasmid bearing the synthetic CRISPR array of five repeats interspaced by four 36-nt spacers targeting the mat, lys, cp, and rep MS2 RNA sequences (GenBank accession number NC001417) was constructed similarly to pCRISPR_S3 (see above).

Computational Sequence and Structure Analysis

Sequence searches were performed with PSI-BLAST (Altschul et al., 1997) against the nr80 sequence database (the NCBI 'nr' database filtered to 80% identity) using E-value=1 e-03 or a more stringent inclusion threshold. Clustering of homologous sequences according to their mutual similarity was done using CLANS (Frickey and Lupas, 2004). Multiple sequence alignments were constructed with MAFFT (Katoh et al., 2002) using the accuracy-oriented mode (L-INS-i). Homology model for StCsm3 was constructed with HHpred (Söding et al., 2005) using the related structure of M kandleri Csm3 (PDB code 4NOL) as a template. The analysis of surface residue conservation was performed using the ConSurf server (Ashkenazy et al. 2010). Electrostatic map of the structure surface was calculated with the APBS (Baker et al. 2001) plugin in PyMol (Schrodinger 2010). Pictures were prepared with PyMol (Schrodinger 2010).

Engineering of Single-Gene Deletion Mutants pCas/Csm plasmid was used as a template to generate the following single-gene deletion mutant variants: pCas/CsmΔCas6, pCas/CsmΔCas10, pCas/CsmΔCsm4, and pCas/CsmΔCsm6'ΔCsm6. To obtain the pCas/CsmΔCas6 variant, pCas/Csm plasmid was cleaved with Bsp1407I, the remaining sticky ends were blunted, phosphorylated (using "Fast DNA End Repair Kit" from Thermo Scientific), and ligated. This resulted into the cash gene truncation to 67 codons. To obtain pCas/CsmΔCas10, a Bsp119I fragment was excised from the pCas/Csm plasmid. The re-ligated plasmid resulted in the cas10 gene truncation to 185 codons. To obtain pCas/CsmΔCsm4, pCas/Csm was cleaved with Spel and Eco31I, blunt-ended and re-ligated. This resulted in Csm4 ORF trunction to 41 codons. To obtain pCas/CsmΔCsm6'ΔCsm6, pCas/Csm was cleaved with Ppil and XmaJI, and resulting larger DNA fragment blunt-ended and subjected to ligation. This resulted in the Csm6' ORF truncation to 324 codons and elimination of Csm6 ORF. To obtain pCas/CsmΔCsm5, pUC18_Csm5_Csm6'_Csm6 plasmid was constructed by subcloning a 2.7 kb DNA fragment containing csm5, csm6', and csm6 genes from pCas/Csm plasmid into pUC18 vector, pre-cleaved with Sphl and Kpnl. pUC18_Csm5_Csm6'_Csm6 was cleaved with Swat and BsaAl, the resulting larger DNA fragment was ligated to yield pUC18_ΔCsm5_Csm6'_Csm6 plasmid, containing a frameshift mutation at the start of csm5 gene. The Sphl and Pact fragment containing Δcsm5, csm6, and csm6 was subcloned into the pCas/Csm plasmid to yield pCas/CsmΔCsm5.

pCas/CsmΔCsm2 and pCas/CsmΔCsm3 were engineered using pUC18_Csm2_Csm3 plasmid (see section Mutagenesis of Csm3). To obtain the pCas/CsmΔCsm2, pUC18_Csm2_Csm3 was cleaved with BspMI and AflII, while to obtain pCas/CsmΔCsm3, pUC18_Csm2_Csm3 was cleaved with Clal and Xhol. The resulting large DNA fragments were then blunted, phosphorylated, and ligated and subcloned into pCas/Csm via Ndel and Spel sites. This resulted in the Csm2 ORF truncation to 70 codons, and Csm3 ORF truncation to 57 codons. Full sequencing of cloned DNA fragments confirmed their identity to the expected sequences. In all cases the deletions were executed in such a way that ribosome binding sites for other genes would not be disrupted. StCsm-40 and StCsm-72 complexes lacking single deleted protein were isolated following the procedures described for the wt StCsm-40 (see above).

Knockdown in Zebrafish

For knockdown, zebrafish lines expressing EGFP from various promoters in different tissues and at different stages of development were used. The promoter:EGFP constructs included vasa:EGFP (Kok et al. 2015, Rossi et al. 2015, Abudayyeh et al. 2016, Shmakov et al. 2015, East-Seletsky et al. 2016, Staals et al. 2014, Tamulaitis et al. 2014, Hale et al. 2009), mito:EGFP (Kim et al. 2008), nkx2.5:EGFP (Witzel et al. 2012), cmcl2:EGFP (Huang et al. 2003), and fli1:EGFP (Lawson et al. 2002) and were used to explore the effect of StCsm complex on maternal RNA deposition without zygotic expression, maternal and zygotic expression, and zygotic expression only. In all experiments, the EGFP transgenes were expressed from transposon insertion sites, always in the background of the endogenous genes.

The vasa:EGFP fish expresses EGFP under the control of the vasa promoter (Krovel et al. 2002). Maternally deposited vasa mRNA is initially present in the entire zebrafish oocyte. The RNA is subsequently targeted to cleavage planes of early embryos and subsequently incorporated into primordial germ cells (PGCs) and degraded elsewhere (Knaut et al. 2002). Zygotic vasa transcription does not set in immediately at the maternal to zygotic transition, but at or just before the onset of gastrulation (Knaut et al. 2000). Vasa protein is initially also present throughout the embryo, but amounts decrease until the midblastula transition, except in germ cells (Braat et al. 2000). The vasa:EGFP reporter line exhibits a pattern of fluorescence consistent with the expression of endogenous vasa. However, genetic experiments demonstrate that maternal vasa:EGFP mRNA is not degraded at the maternal to zygotic transition and is exceptionally stable for at least 50 hours of development. Moreover, heterozygous embryos from mothers with and fathers without the transgene do not exhibit fluorescence in this period, suggesting the absence of zygotic expression of the transgene during this time (Krovel et al. 2002). The vasa:EGFP fish therefore are a good test system for knockdown of maternal RNA without confounding effects of embryonic transcription. The mito:EGFP fish express EGFP with N-terminal mitochondrial localization signal derived from subunit VIII of cytochrome oxidase under the control of the control of the constitutive elongation factor 1α (EF-1α) (Kim et al. 2008). Bright mitochondrial fluorescence of unfertilized oocytes suggests that maternal deposition of EGFP in mitochondria and likely also maternal mRNA deposition. As mito:EGFP fish also express EGFP in the zygote, this fish line represents a case of both maternal and zygotic transcripts (Kim et al. 2008).

The nkx2.5:EGFP fish express the fluorescent protein under the control of the Nkx2.5 promoter. Initial expression of the endogenous gene is detected in the ventral margin of the embryo at the onset of gastrulation (~5.5 hours post fertilization (hpf). At 10 somite stage (~12 hpf), nkx2.5 is expressed in two tubes, which fuse an move to the left at about (~1 days post fertilization (dpf)). By 2 dpf, nkx2.5 expression is limited to the heart. The nkx2.5:EGFP fish faithfully recapitulate the expression pattern of the endogenous gene. At 10 somite stage, fluorescence is seen in two tubes, which subsequently fuse. At 2 dpf, EGFP expression occurs only in the heart (Witzel et al., 2012).

The cmcl2:EGFP (also known as myl7:EGFP) fish express the fluorescent reporter in the myocardial cells of the heart chamber, but not the epi- or endocardium (Huang et al., 2003). Expression of the endogenous mRNA becomes detectable later for cmcl2:EGFP compared to nkx2.5:EGFP, at about 16 hpf. At around this time, fluorescence of the cmcl2:EGFP reporter becomes detectable by fluorescence and then persists for the lifetime of the animal (Huang et al. 2003).

The fli1:EGFP fish express EGFP in the blood vessels. Low fluorescence level is detectable from the three-somite stage (~10 hpf). At 1 dpf, trunk and segmental vessels as well as cells with erythroid morphology are fluorescently labelled. At 2 dpf, there is also fluorescence in the neural crest derived aortic arches and the developing jaw (Lawson et al. 2002). Therefore the hearts of nkx2:5:EGFP and cmcl2:EGFP and vessels of fli1:EGFP reporter lines are good test cases to check knockdown of zygotically expressed EGFP in the embryo.

Study Design

Figure 21:
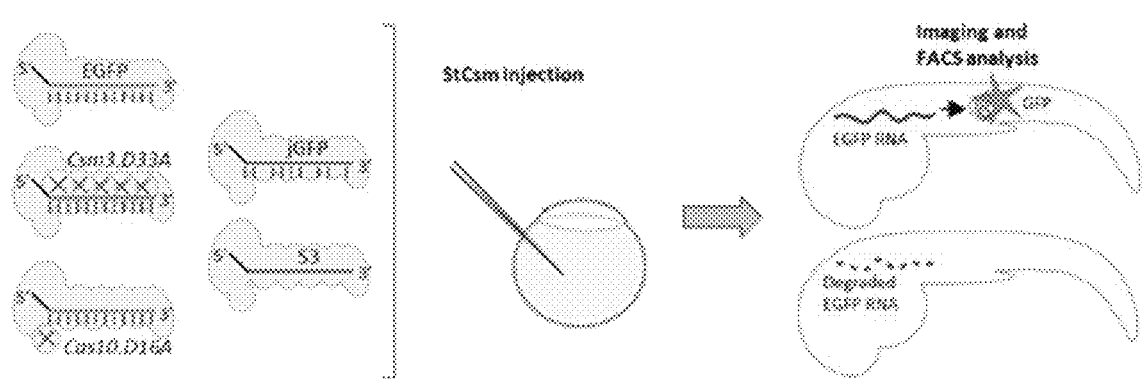
FIG. 21 shows the experimental design injecting purified wild-type, DNase (D16A) or RNase (D33A) defective variants of StCsm complexes comprising EGFP, jGFP, or S3 crRNA into zebrafish. Comparison of the different complexes' abilities to degrade EGFP transcript, also injected into zebrafish embryos, allowed determination of expression or suppression of a transgene. Suppression of EGFP fluorescence was monitored by imaging and FACS analysis. The level of crRNA complementarity to EGFP transcript is indicated by vertical bars in the StCsm complexes.

Csm complexes could be used for mRNA knockdown in zebrafish was investigated. To meaningfully compare efficacies in different tissues and in different developmental stages, endogenous messenger RNAs were not targeted. Instead, the EGFP transcripts expressed from transgenes under the control of a variety of different promoters were used. To judge the specificity of the mRNA targeting, an optimal crRNA guides for EGFP, jellyfish GFP (jGFP), and S3 transcripts, were used (FIG. 26). To distinguish between Csm RNase and DNase dependent effects, variants were prepared of the crRNA Csm complexes that differed from the wild-type complex by the D33A substitution in Csm3 (DNase activity only) and the D16A substitution in Cas10 (RNase activity only). Complexes were injected into the yolk of zebrafish at the 1-cell stage, and EGFP fluorescence was then monitored at different time points, either by direct observation or FACS analysis of trypsin-digested embryos (FIG. 21).

Bacterial Expression and Purification of StCsm-crRNA Complexes

Figures 22A, 22B:
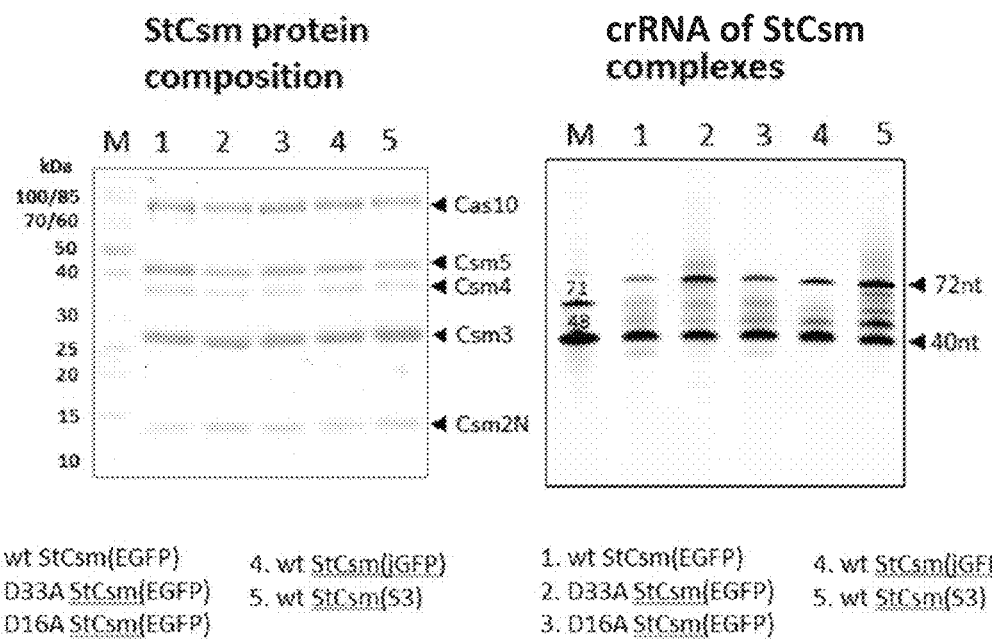
FIGS. 22A-C show in vitro characterization of StCsm complexes.

To generate pre-crRNAs for loading of Csm complexes in the *Escherichia coli* expression host, synthetic CRISPRs were generated. These contained the 36 nucleotide repeats found in the Cas/Csm associated CRISPR cluster of *S. thermophilus* DGCC8004, and four identical spacers of reverse complementary sequence to the targeted region of EGFP, jGFP or S3 RNA. The pre-crRNAs were then co-expressed with the *S. thermophilus* Csm genes and co-purified with processed crRNA. Moreover, the Cas10 D16A and Csm3 D33A variants of the StCsm complex were also prepared together with EGFP crRNA (7). The purified Csm(EGFP), Csm(jGFP), Csm(S3), D16A Csm(EGFP) and D33A Csm(EGFP) complexes were checked for protein purity by denaturing gel electrophoresis and Coomassie staining (FIG. 22A). Their crRNA content was analyzed by denaturing PAGE analysis followed by RNA SYBR Gold staining (FIGS. 22A and 22B). The results confirmed essentially equal protein content of all complexes and approximately equal crRNA content of all complexes. Csm complexes contained a mixture of a 72 nucleotide long crRNA arising from cleavage of the pre-crRNA, and of 40 nucleotide long crRNA arising from further trimming of this crRNA, as described earlier (Tamulaitis et al. 2014).

Test Tube Validation of the RNase and DNase Activities of Csm-crRNA Complexes

Figure 22C:
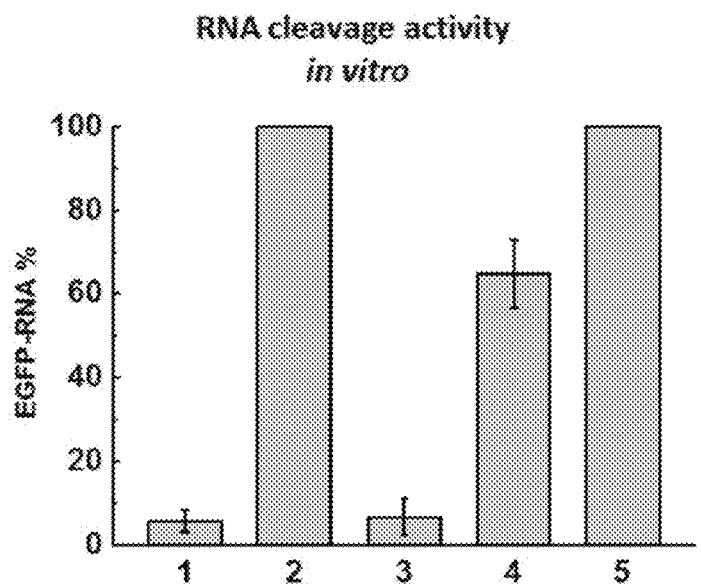
Figure 26A:
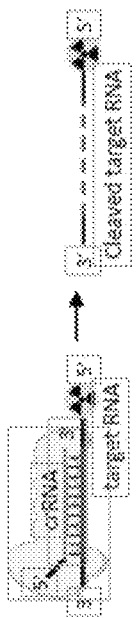
FIGS. 26A and 26B illustrate an in vitro RNA cleavage assay.
Figure 26B:
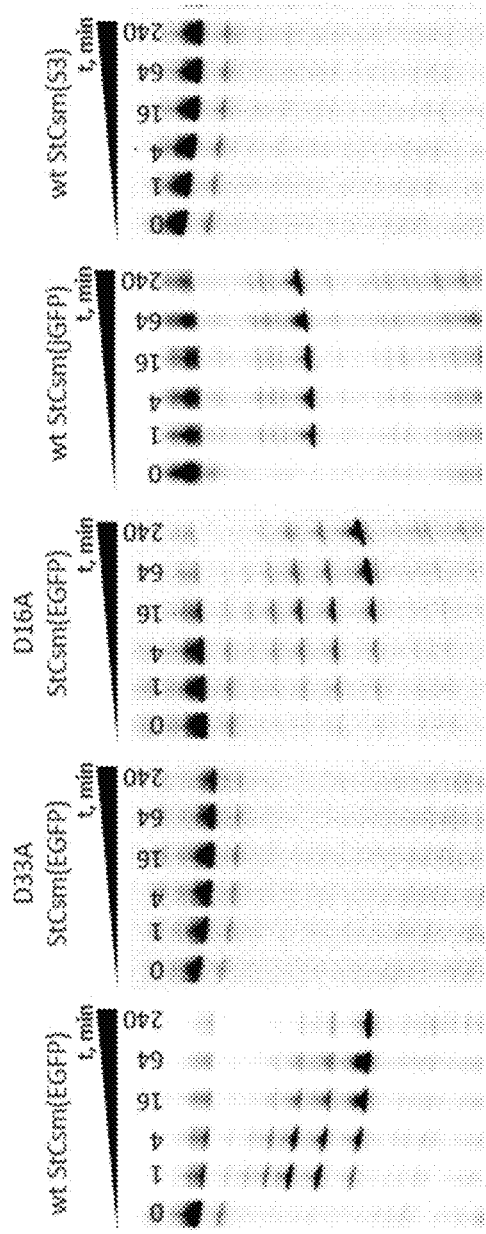

The RNase activity of the StCsm complexes was tested at 28° C., the temperature used for the zebrafish experiments. Cleavage of a radiolabelled RNA fragment containing the EGFP target region was monitored over time (FIGS. 26A and 26B), and the remaining amount of substrate was quantified after one hour of incubation (FIG. 22C). The wt StCsm(EGFP) cleaved complementary substrate RNA with the characteristic 6-nucleotide stagger described earlier (Tamulaitis et al. 2014, Hatoum-Aslan et al. 2013). In contrast, the amount of substrate remained essentially unchanged after the one hour incubation period with the RNase defective D33A variant. In contrast, the DNase defective D16A mutant cleaved the substrate RNA like the wild-type StCsm complex. Mismatches between guide and target sequence hindered RNA cleavage more effectively at lower than at higher temperature. At 28° C., incubation of the substrate with StCsm(jGFP) (three clustered and three isolated mismatches between crRNA and target) left most of the substrate undigested, demonstrating good specificity of the StCsm crRNA complexes. Incubation of substrates with an irrelevant (S3) guide did not cause any RNA cleavage (FIG. 22 and FIGS. 26A and 26B).

Figure 27A:
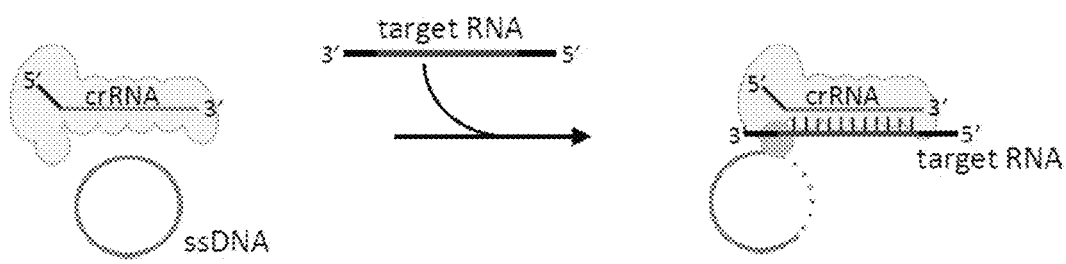
FIGS. 27A and 27B depict a DNA cleavage assay in vitro.
Figure 27B:
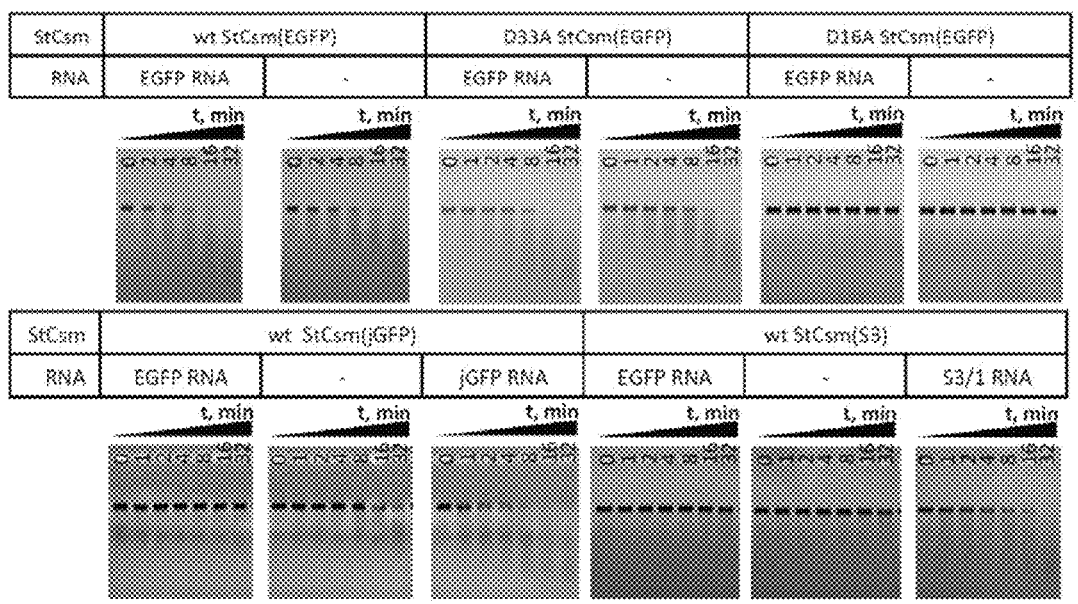

The DNase activity of the StCsm complexes was tested with a single stranded DNA substrate in the presence of target RNA mimicking a transcript, again at 28° C., the relevant temperature for the zebrafish experiments. In agreement with earlier data (Kazlauskiene et al., 2016), robust DNA degradation was observed when StCsm crRNA complexes were used together with matched RNAs. However, DNA degradation appeared to occur on a slower timescale than RNA degradation. As predicted, DNA degradation was unaffected by the D33A mutation, but completely impaired by the D16A mutation. The StCsm(jGFP) and StCsm(S3) complexes that had mismatched and unrelated guides to the EGFP RNA did not cleave DNA, even though they were active in the presence of their matched RNAs (FIG. 27). RNA dependent DNA degradation is also very specific.

Knockdown of the Maternal Vasa:EGFP

Figure 28A:
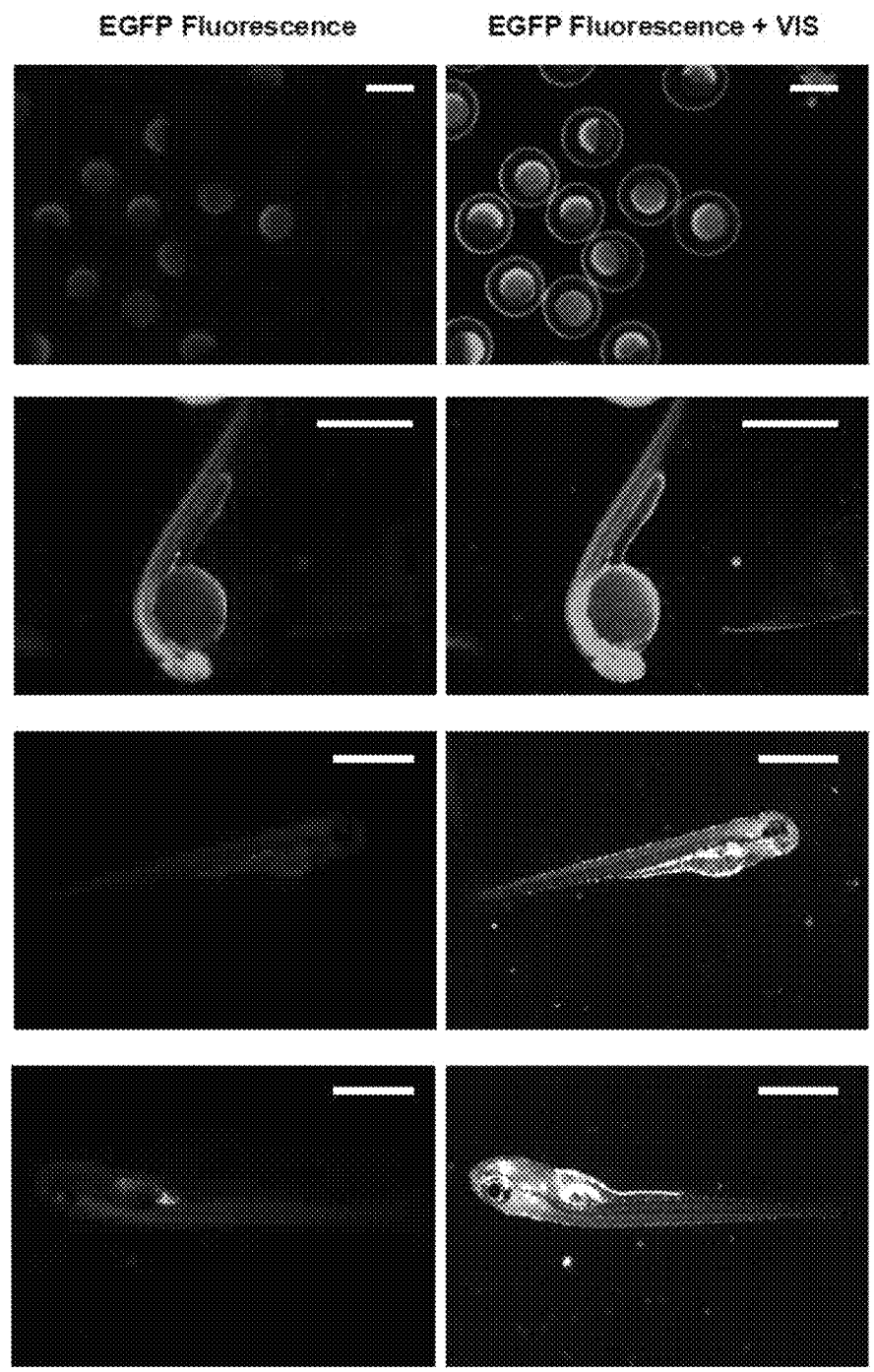
FIG. 28A and FIG. 28B show in vivo vasa:EGFP fluorescence in reciprocal crosses of ABTL and vasa:EGFP parents.
Figure 28B:
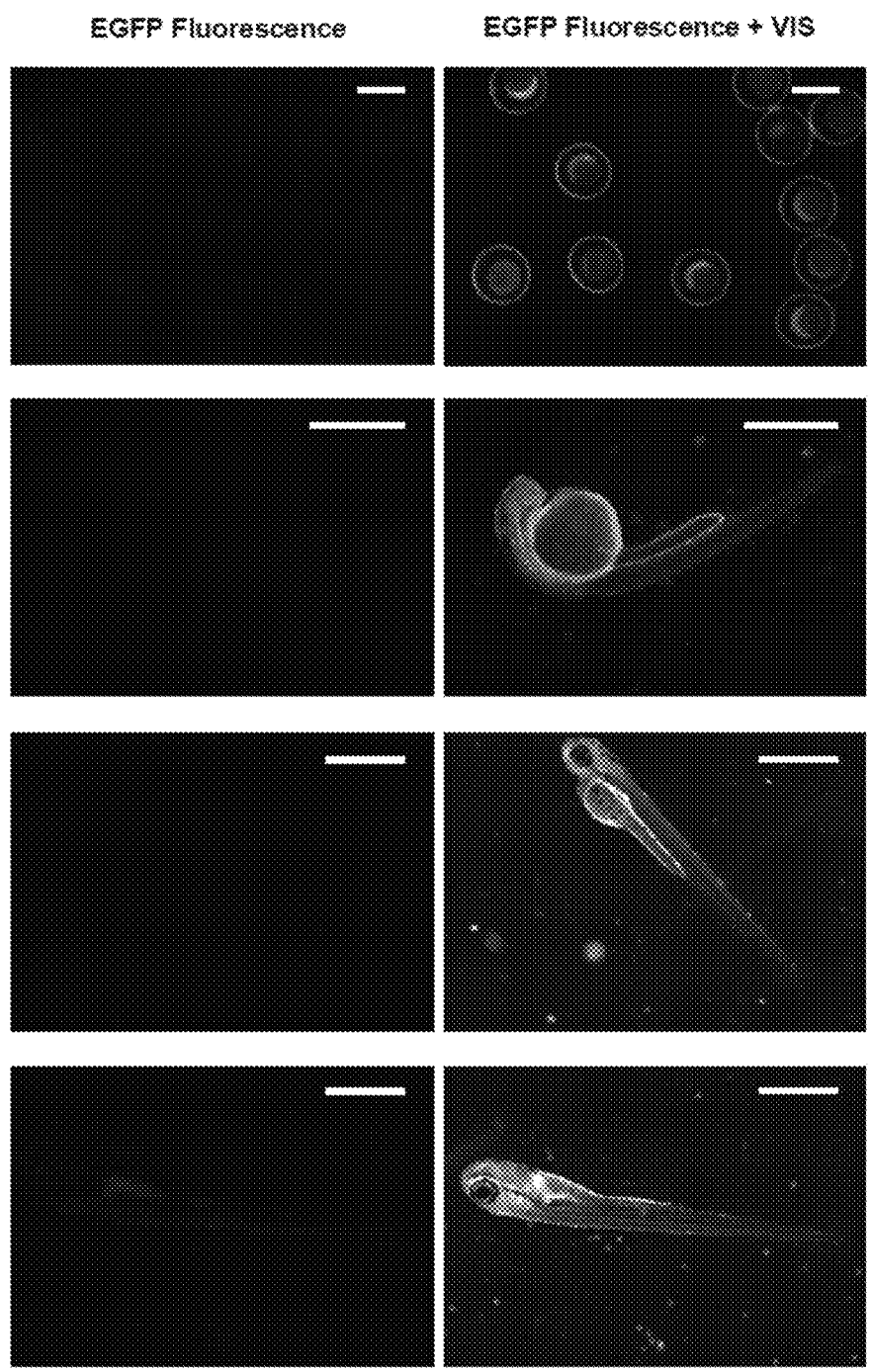

The inventors' fluorescence of vasa:EGFP fish was consistent with literature reports (18,23). EGFP fluorescence was not observed up to 5 dpf (the last time point checked due to legal restrictions) embryos derived from crosses of wt females with vasa:EGFP males. This observation confirmed that vasa:EGFP was exclusively expressed from the maternal transcript and that transcription of the EGFP transgene, unlike the transcription of endogenous vasa, does not set in at the gastrulation stage (FIG. 28).

Figure 23:
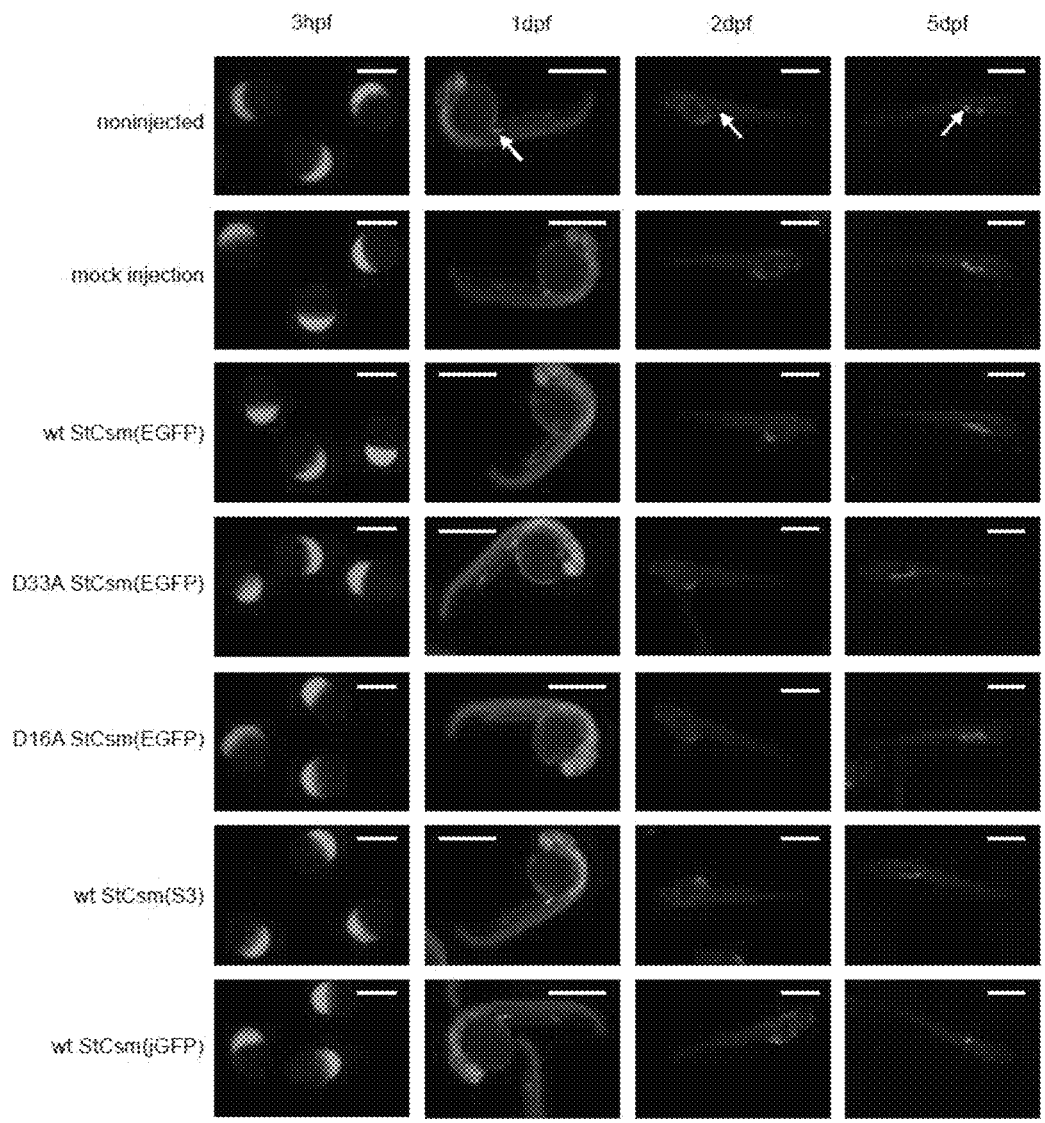
FIG. 23 illustrates microscopic analysis of StCsm mediated EGFP knockdown in vasa:EGFP fish. Fluorescence from vasa:EGFP fish after injection with wildtype or mutant St-Csm-crRNA complexes. Injection was done at the 1-cell stage, observation were 3 hour post fertilization (hpf), 1 days post fertilization (dpf), 2 dpf and 5 dpf. The scale bar represents 1 mm.
Figures 29A, 29B, 29C, 29D:
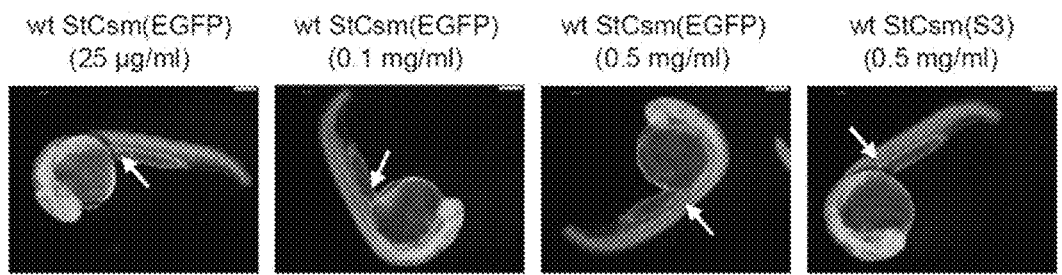
FIGS. 29A, 29B, 29C, and 29D show the dose dependence of vasa:EGFP knockdown (25 µl of wildtype StCsm (EGFP), 0.1 mg/ml of wildtype StCsm (EGFP), 0.5 mg/ml of wildtype StCsm (EGFP), and 0.5 mg/ml of wildtype StCsm (S3) injections). At 0.5 mg/ml, the majority of embryos did not show EGFP fluorescence in germcells.

In initial experiments, a minimal dose of StCsm(EGFP) to achieve knockdown was determined (FIG. 29). The following descriptions include only use of this optimal dose of 1 nl 0.5 mg/ml StCsm(EGFP) crRNA into the yolk of 1-cell stage vasa:EGFP embryos (from mating's of vasa:EGFP mothers and fathers). No differences were observed in fluorescence between non-injected embryos, mock-injected embryos, or embryos injected with the StCsm, in the early stages of development (3 hpf), presumably due to maternally deposited protein. However, fluorescent imaging of the embryos at 1 dpf to 5 dpf showed clear reduction of fluorescence in the germ cells of embryos injected with wt StCsm(EGFP) compared to non-injected controls. Fluorescence from these cells (above background in the entire embryo) was almost completely abolished at 1 dpf (FIG. 23). However, in a small fraction of fish, the injections did not have a clear-cut effect, suggesting technical issues rather than a knockdown failure. The loss of fluorescence compared to control in the germ cells of wt StCsm(EGFP) injected embryos was persistent at least during the first five days of development. Knockdown did not affect the (weak) background fluorescence initially in the entire embryo and primarily in the brain, which may be explained by maternal deposition of EGFP protein.

As the EGFP in the vasa:EGFP strain is expressed exclusively from the maternal RNA, the loss of fluorescence should be the result of RNA knockdown, and should not be dependent on potential effects of the DNase activity of the complex on the transgene itself. To verify this prediction biochemically, embryos were injected with the DNase dead mutant D16A StCsm (EGFP). The D16A StCsm(EGFP) extinguished fluorescence at 1 dpf like the wild-type protein. As a further control, embryos were injected instead with the RNase dead D33A variant of the Csm-crRNA complex. The mutant did not cause a noticeable decrease in fluorescence, confirming that the decrease was indeed due to RNA knockdown and not to indirect effects on RNA. Finally, the consequences of imperfect reverse complementarity between jGFP crRNA and EGFP mRNA were assessed. The six mismatches between the two RNAs appeared to abolish EGFP degradation (FIG. 23).

For quantitation, embryos from mating of a single pair of fish were minced and trypsinized, and the resulting pool of cells and aggregates of cells was subject to fluorescence activated cell sorting (FACS). To avoid the influence of background fluorescence, the gating window in the FACS was set to count cells only in the region of very high fluorescence, 50-fold above mean. The number of cells with fluorescence above the threshold was then used as a measure of fluorescence. Analysis of 1 dpf and 2 dpf embryos showed 20-fold and 6-fold reductions in the numbers cells with high EGFP fluorescence with wt and D16A StCsm(EGFP). No reduction of fluorescence was observed using the RNase dead D33A StCsm(EGFP), the wt StCsm(jGFP) complex with imperfectly complementary RNA or the control crRNA wt StCsm(S3) (FIG. 24A). Differences were significant independently of the precise choice of threshold for highly fluorescent cells (not shown). The highly fluorescent cells showed a high side scatter, consistent with the increased size of primordial germ cells (Braat et al. 1999).

Knockdown of the Mixed Maternal-Zygotic Mito:EGFP

Figure 30A:
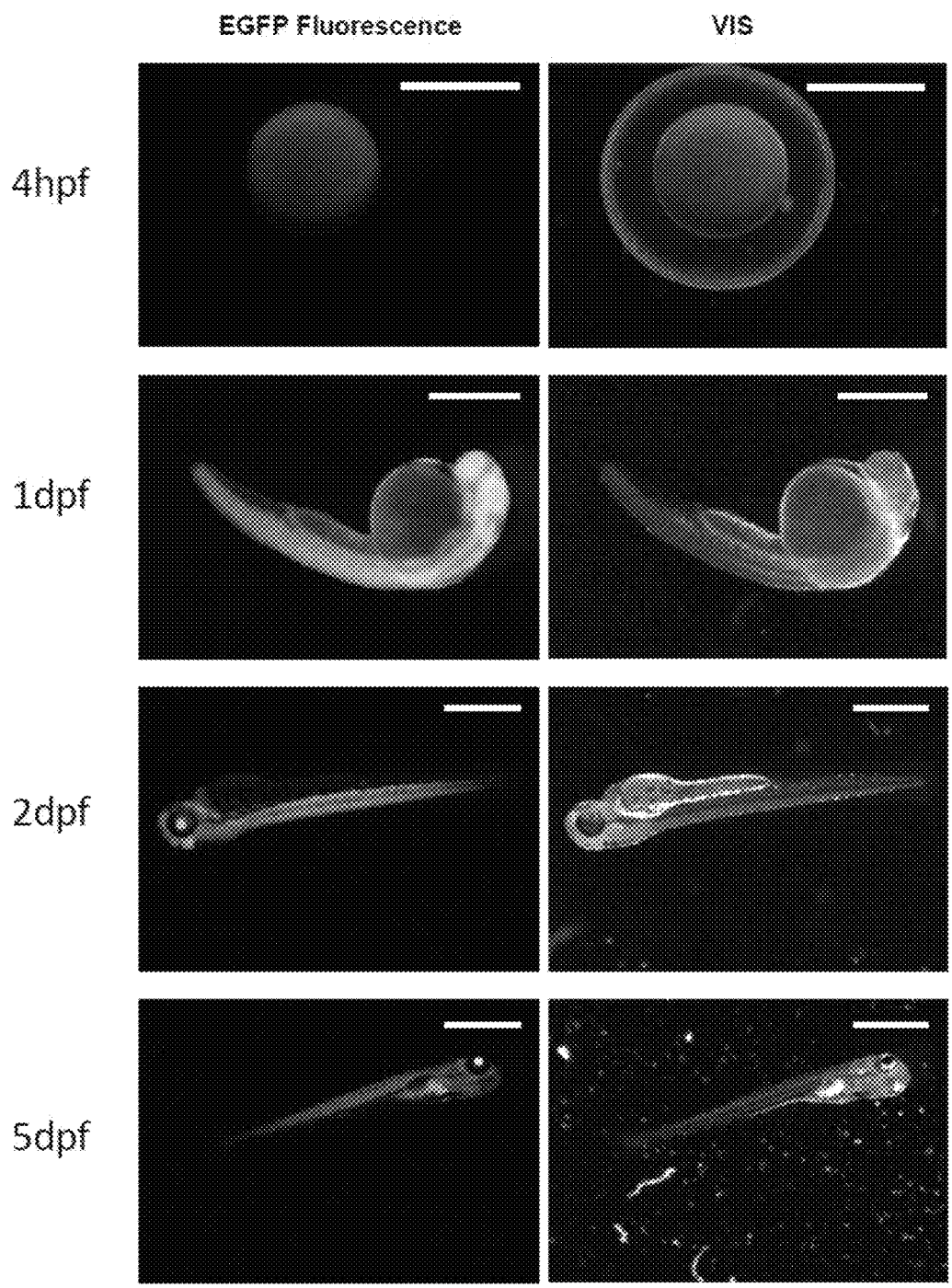
FIGS. 30A and 30B depict mito:EGFP fluorescence in reciprocal crosses of ABTL and mito:EGFP parents.
Figure 30B:
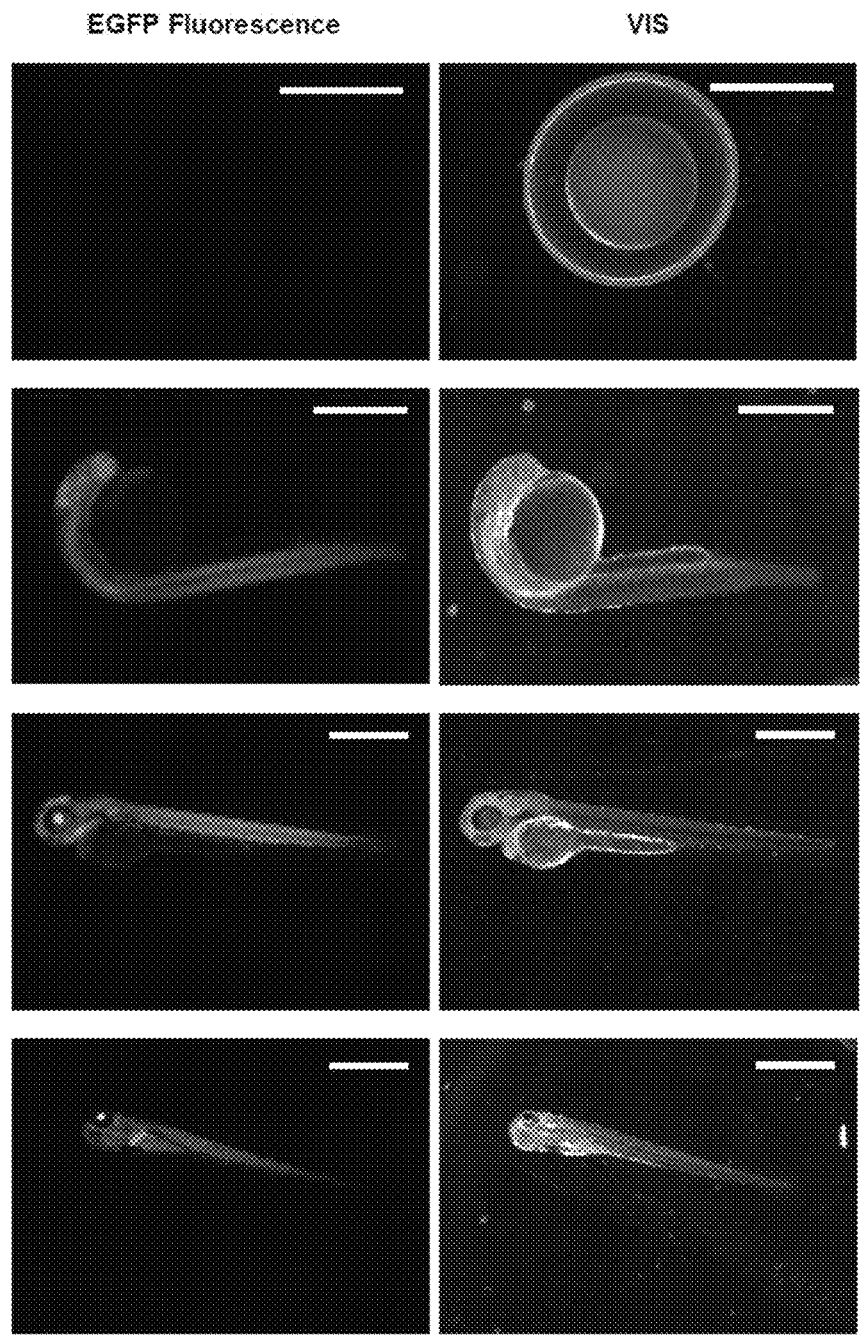

Embryos from mito:EGFP show green fluorescence in mitochondria already in oocytes, and throughout the life of the fish. In crosses between wild-type ABTL fish and mito: EGFP fish, fluorescence is observed throughout embryonic development when the mother carries the mito:EGFP transgene, indicating maternal and then zygotic expression, whereas fluorescence is observed only after the midblastula transition in the reciprocal cross (FIG. 30). For knockdown experiments, the same concentrations of StCsm(EGFP) and variants were used as in the vasa:EGFP experiment. The lines were analyzed by fluorescence microscopy and FACS analysis of digested embryos at 1 dpf, and in the case of the mito:EGFP×mito:EGPF crosses, also at 2 dpf. As green fluorescent is present throughput the embryo and not concentrated in a particular cell type, mean fluorescence, instead of the number of highly fluorescent cells, was quantified for the vasa:EGFP fish.

Figure 31A:
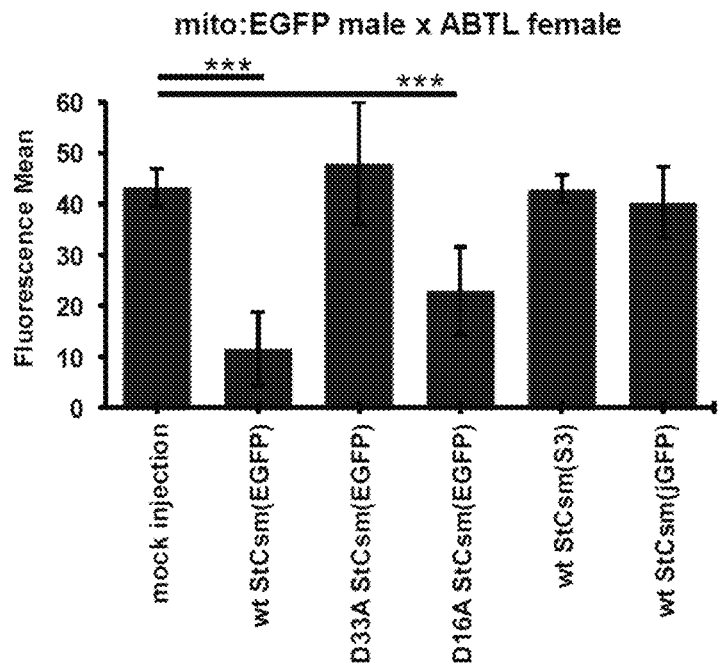
FIGS. 31A and 31B show quantification of knockdown efficiency by FACS analysis: EGFP mRNA was knocked down in fishes derived from reciprocal crosses of wild-type ABTL and mito:EGFP lines. Mean fluorescence was quantified 1 dpf by FACS analysis of digested embryos. Results are from three independent experiments, error bars represent one standard deviation (***P<0.001 as compared with respective controls).
Figure 31B:
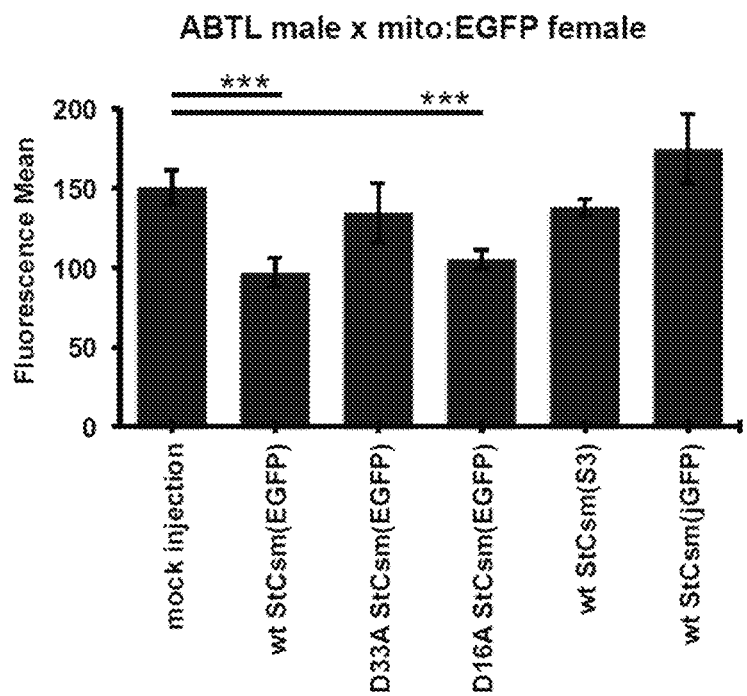
Figure 32:
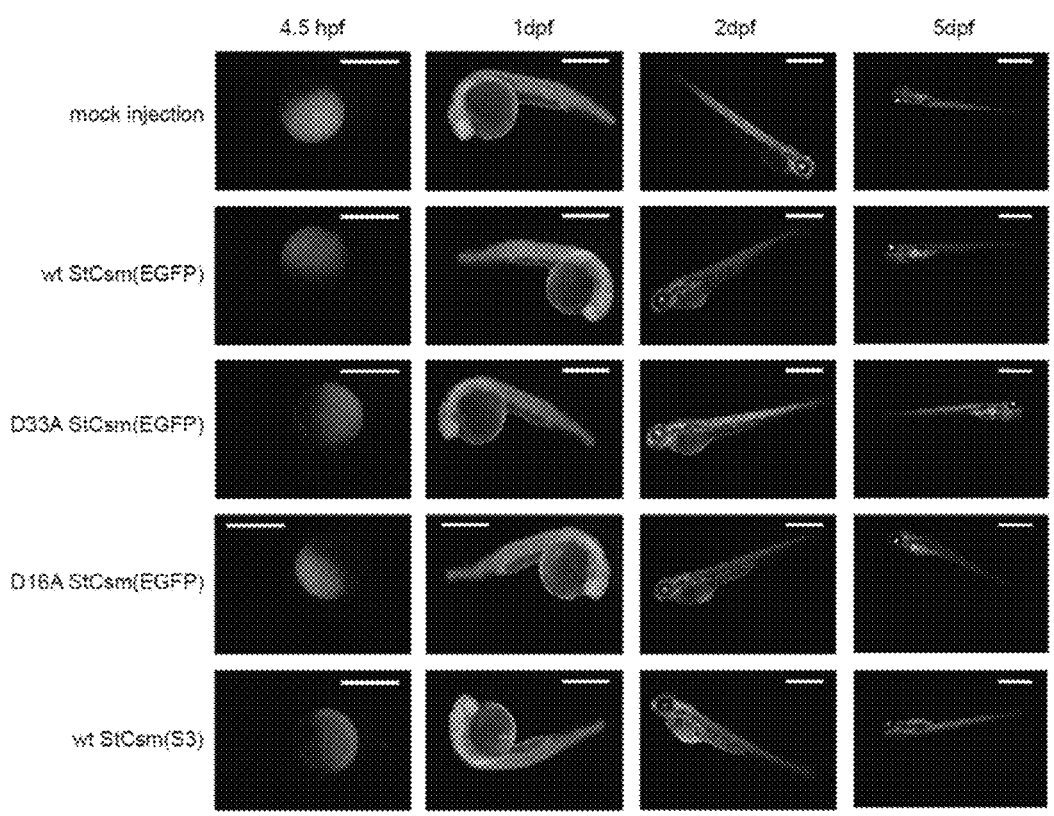
FIG. 32 shows the effects of injection of a mock injection, StCsm crRNA complexes (wt StCSM(S3), wt StCsm (EGFP), D33A StCsm(EGFP), and D16A StCsm(EGFP) into mito:EGFP embyros from crosses of mito:EGFP parents at 4.5 hpf, 1 dpf, 2dpf, and 5dpf.

Using fish from mito:EGFP mothers and wild-type fathers, knockdown efficiency using wild-type StCsm (EGFP) was good. The knockdown efficiency was insignificantly lower with the D16A variant, arguing for a possible contribution of DNA cleavage in the observed reduction of fluorescence. However, the D33A variant, which has only DNase activity, was completely ineffective, suggesting that the reduction of fluorescence was not due StCsm(EGFP) DNase activity (FIG. 31A). When repeated for the reciprocal cross, the reduction in fluorescence that could be achieved by StCsm (EGFP) injection was much lower, either because maternal RNA overwhelms StCsm (EGFP) capacity, or more likely because fluorescence of maternally deposited EGFP protein is not affected by the knockdown (FIG. 31B). A similarly low knockdown efficiency was also observed when the StCsm (EGFP) was administered to knockdown maternally deposited RNA and zygotically expressed RNA in embryos from crosses of mito:EGFP parents (FIG. 24B and FIG. 32).

Knockdown of the Zygotic cmcl2:EGFP and fli1:EGFP, but not nkx2.5:EGFP

Figure 33A:
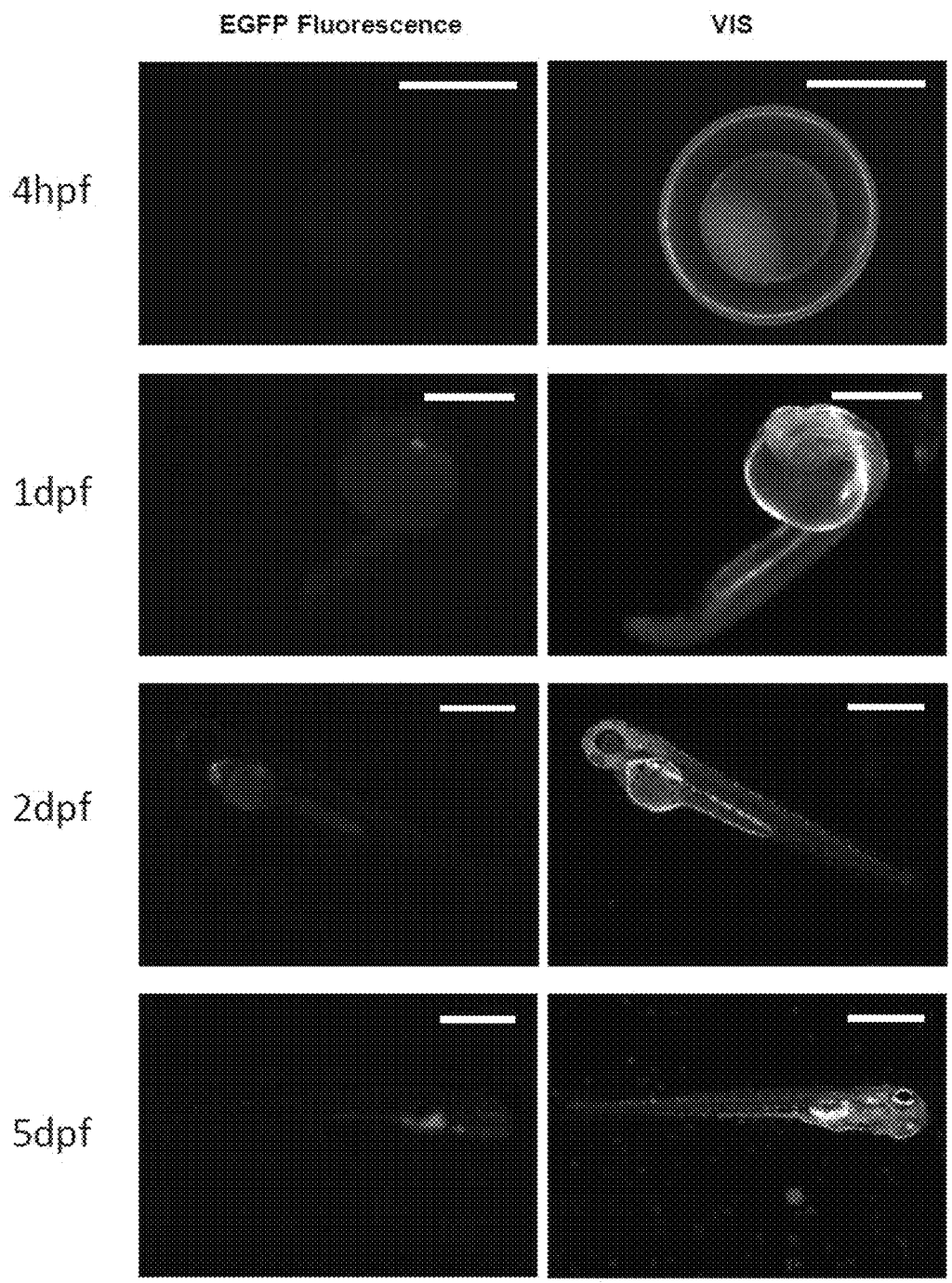
FIGS. 33A and 33B show nkx2.5:EGFP fluorescence in reciprocal crosses of ABTL and nkx2.5:EGFP parents.
Figure 33B:
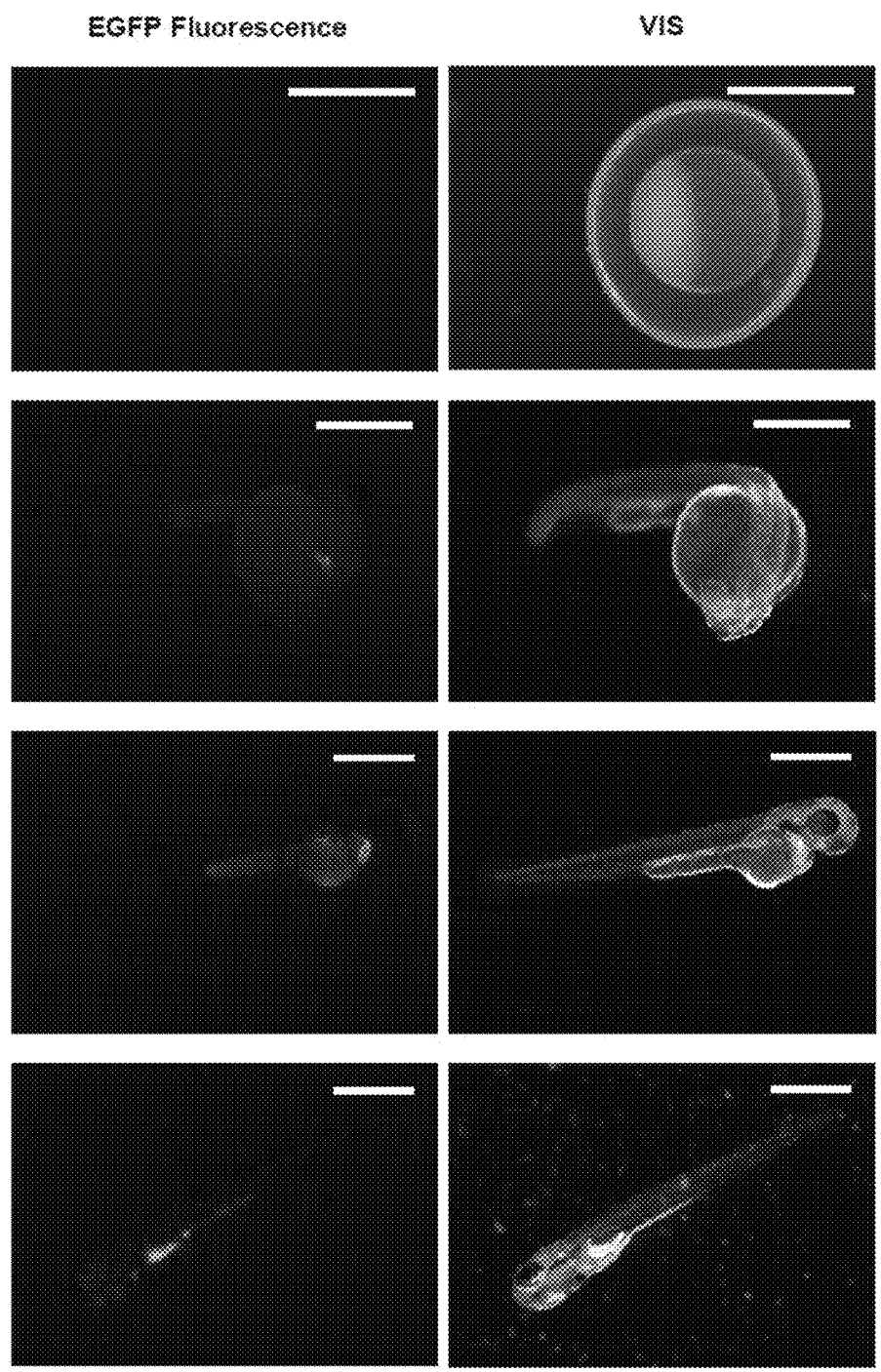
Figure 34A:
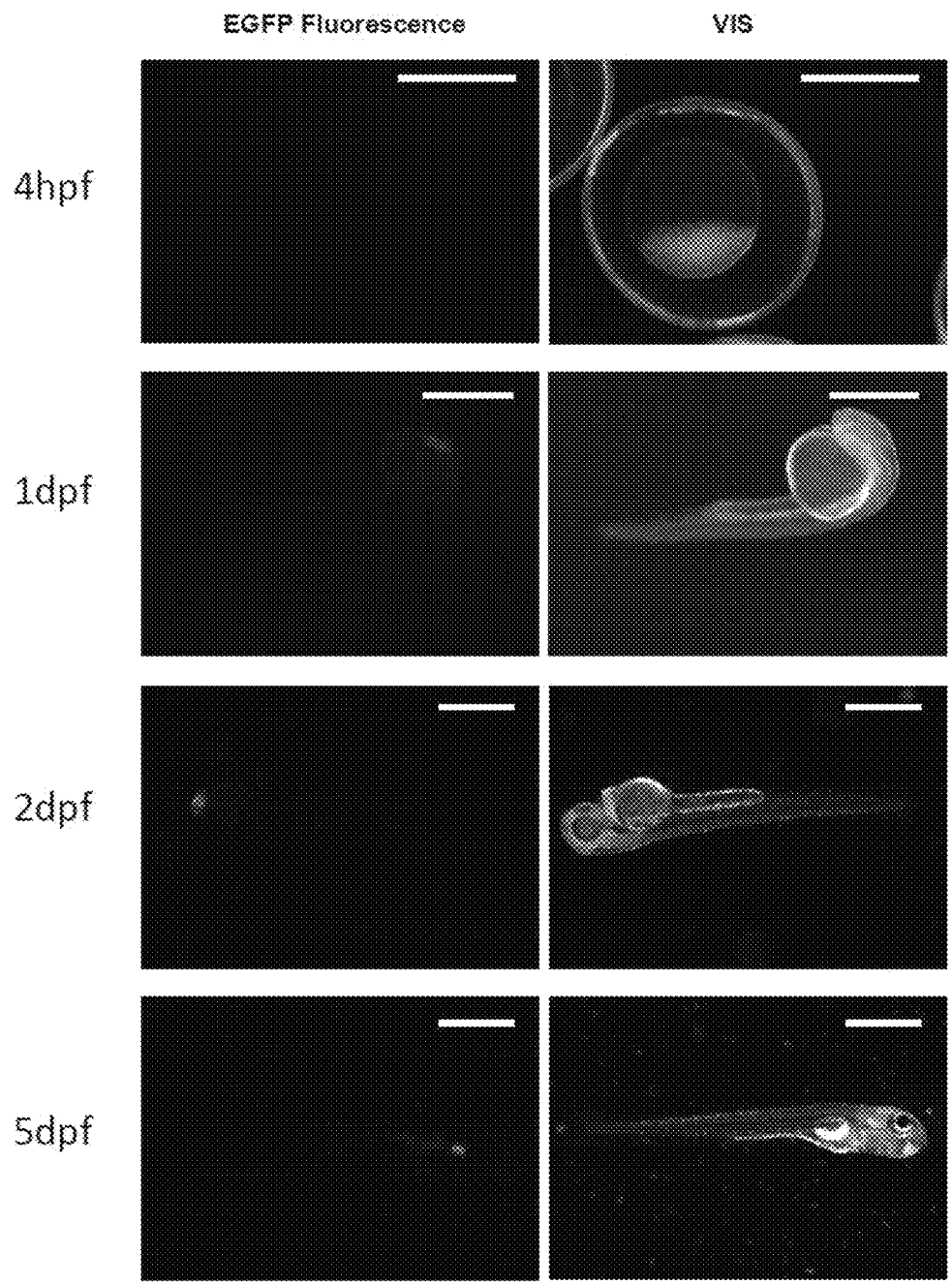
FIGS. 34A and 34B show cmcl2:EGFP fluorescence in reciprocal crosses of ABTL and cmcl2:EGFP parents.
Figure 34B:
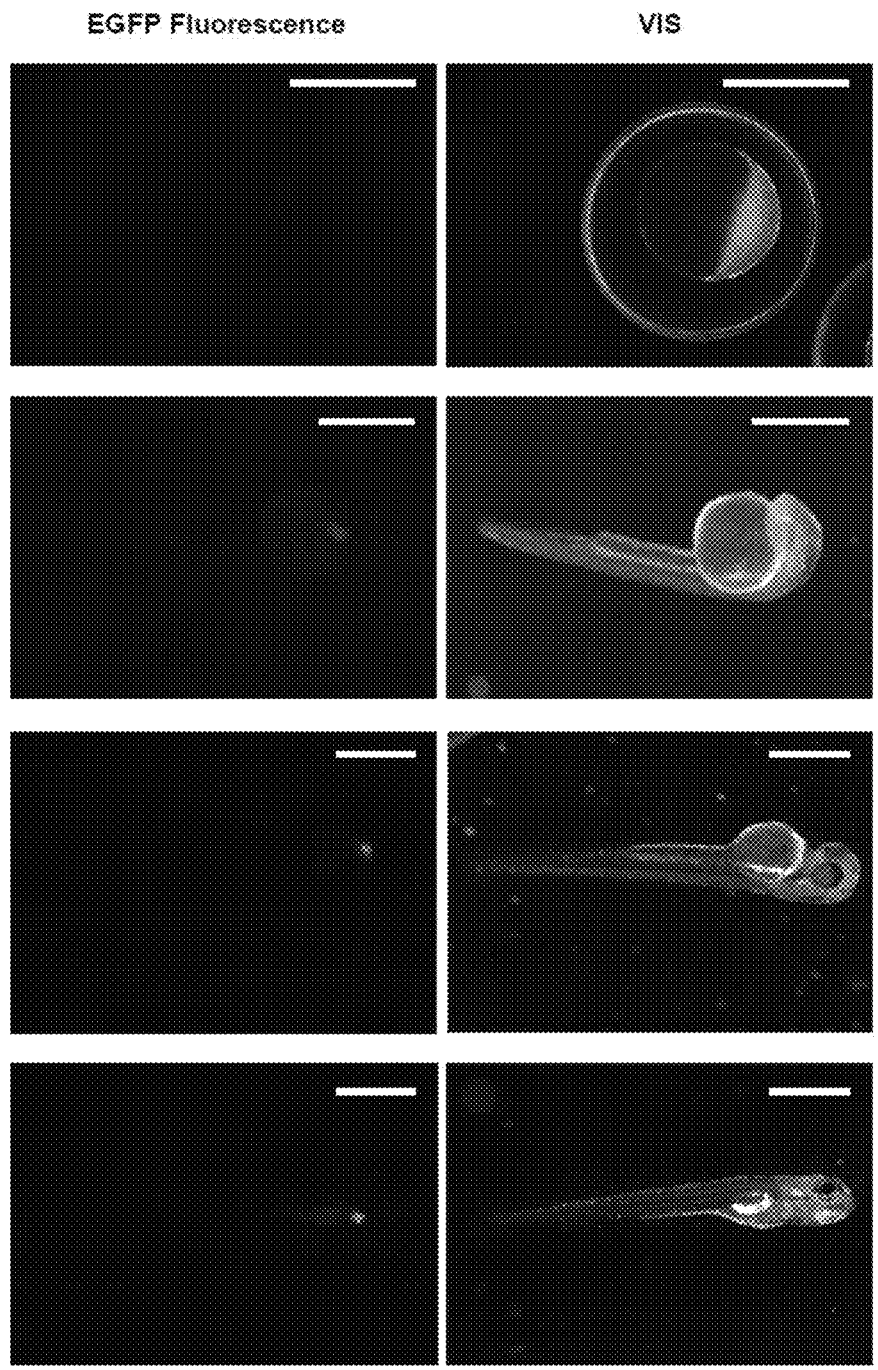
Figure 35A:
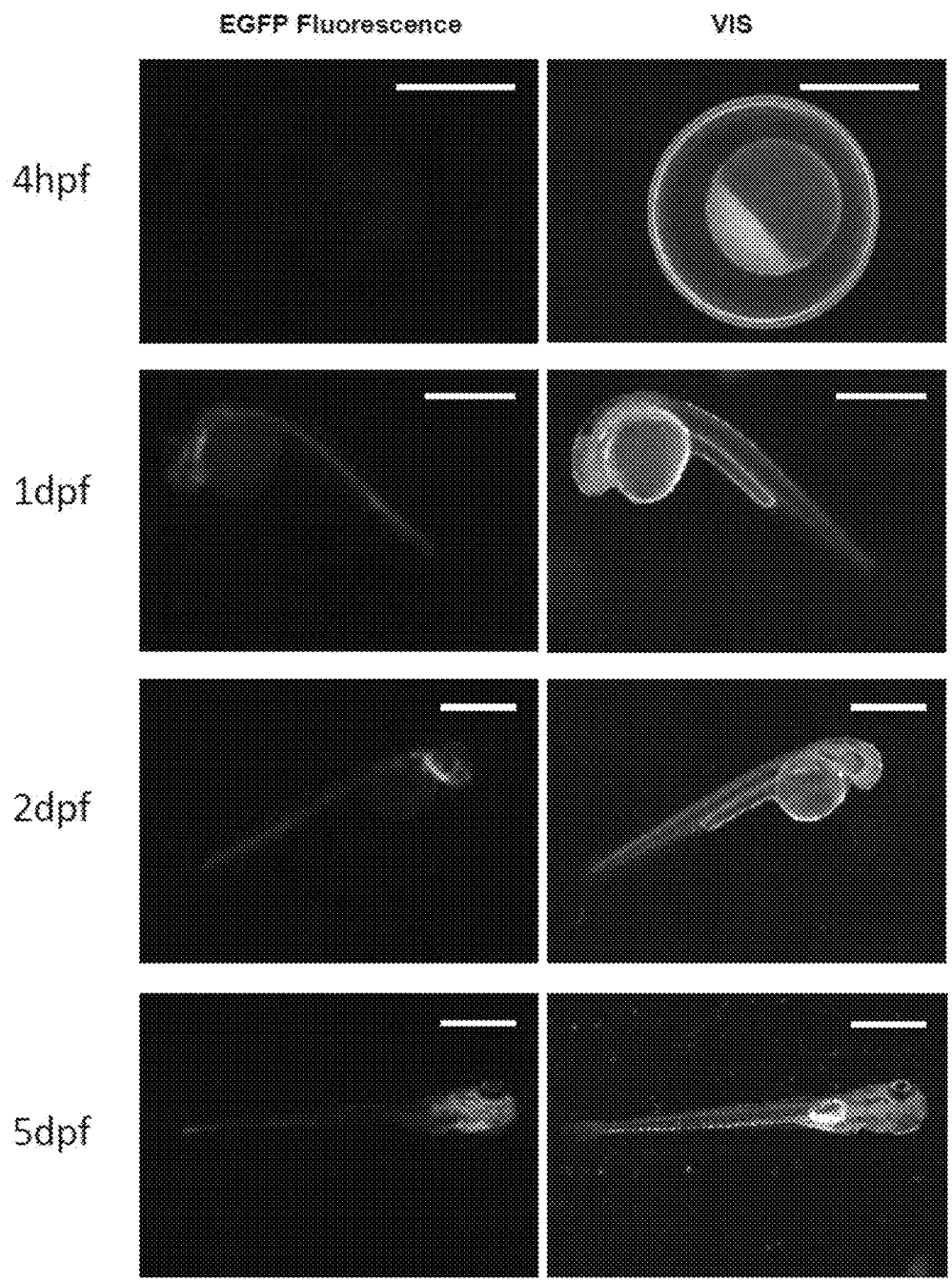
FIGS. 35A and 35B show fli1:EGFP fluorescence in reciprocal crosses of ABTL and fli1:EGFP parents.
Figure 35B:
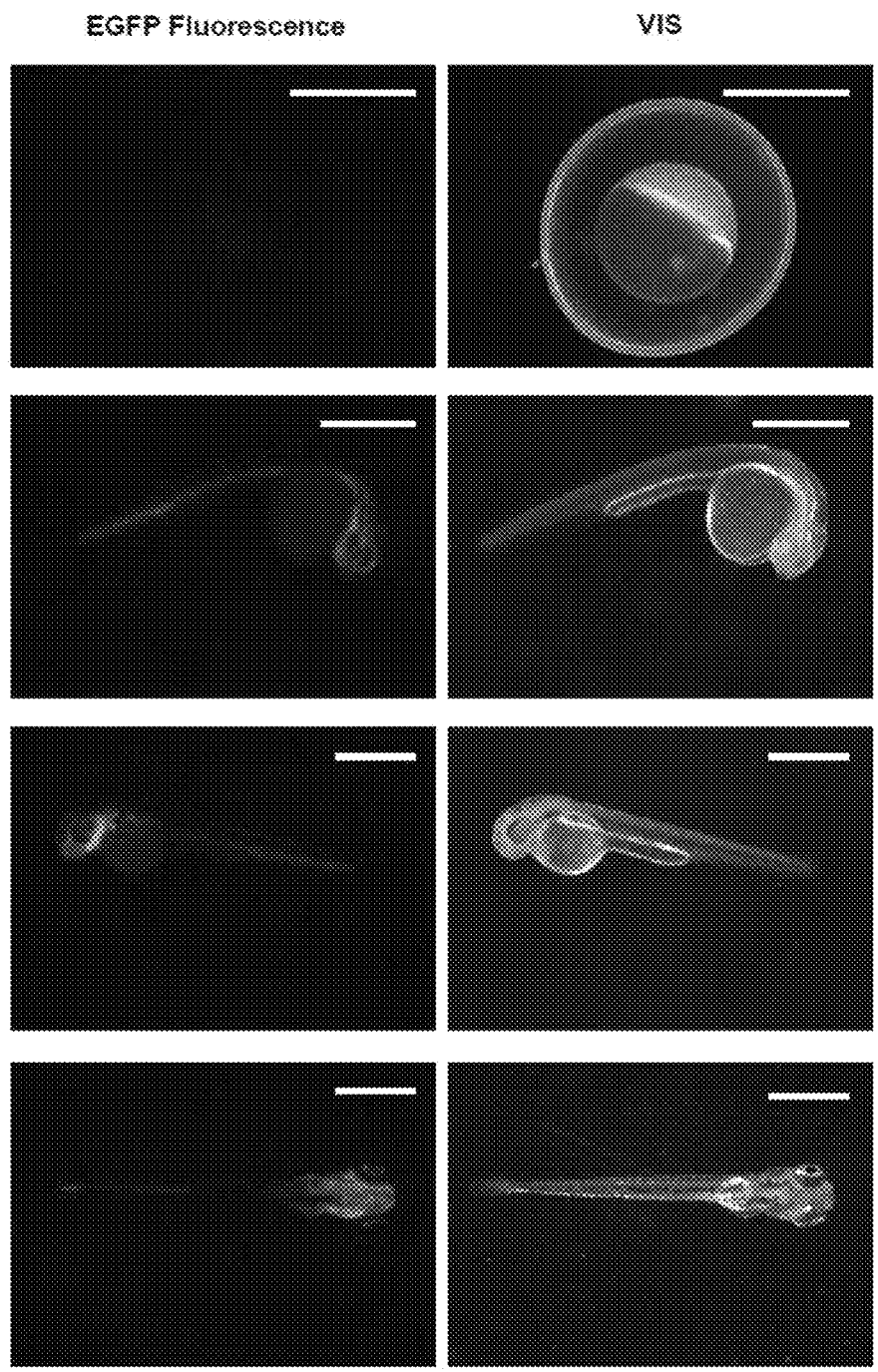

To confirm that StCsm(EGFP) could also be used to for knockdown of zygotically expressed mRNAs, knockdown of EGFP transcripts from other promoters were tested. Consistent with predominantly zygotic promoter activity, heterozygotic nkx2.5:EGFP, cmcl2:EGFP or fli1:EGFP fish carrying a maternally or paternally inherited transgene exhibited similar fluorescence at all tested time points (4 hpf, 1 dpf, 2 dpf, 5 dpf) (FIGS. 33-35). As before, the amount of StCsm(EGFP) for injections was not optimized anew and the same concentration as for the vasa:EGFP experiments was used throughout. All lines were analyzed by fluorescence microscopy and FACS analysis of digested embryos at 1 dpf and 2 dpf.

Figure 36:
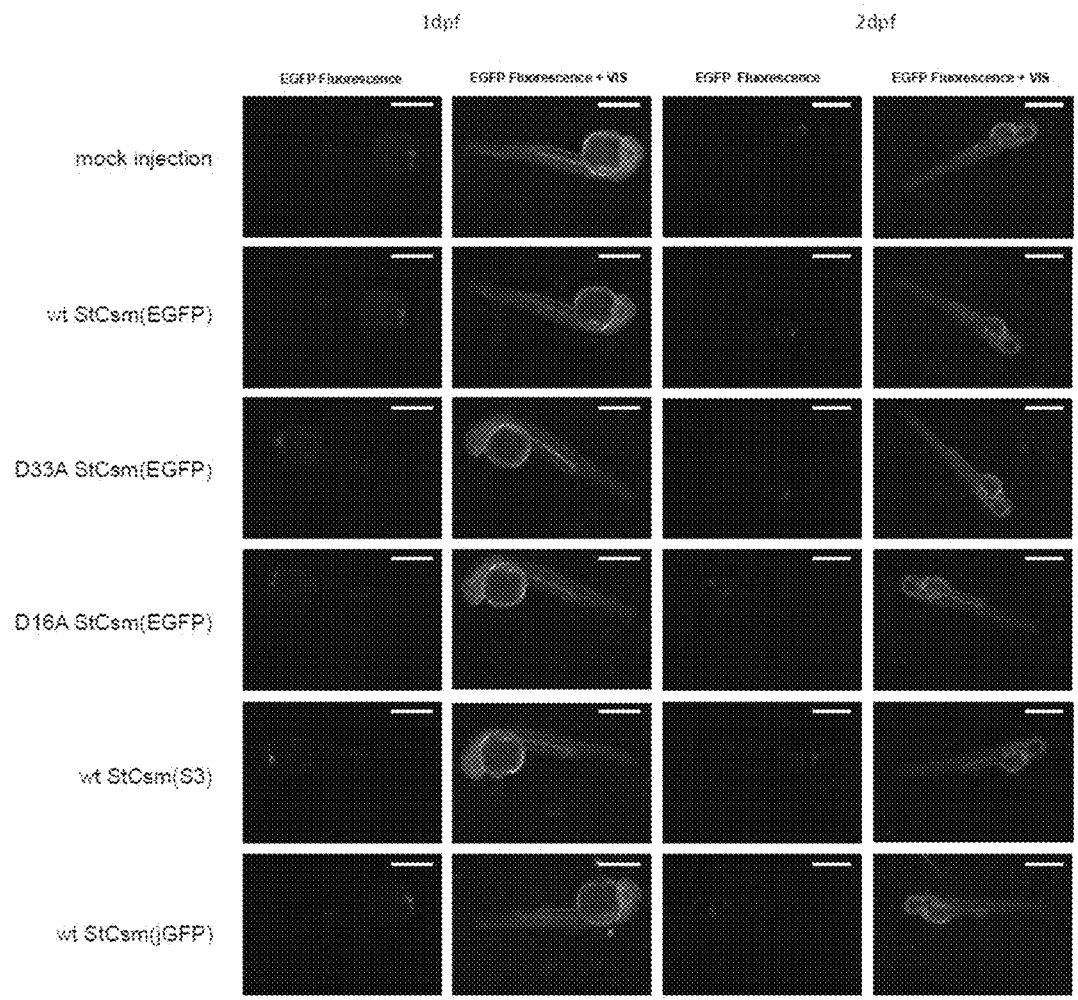
FIG. 36 depicts the effects of the injection of StCsm crRNA complexes into nkx2.5:EGFP embyros.
Figure 37:
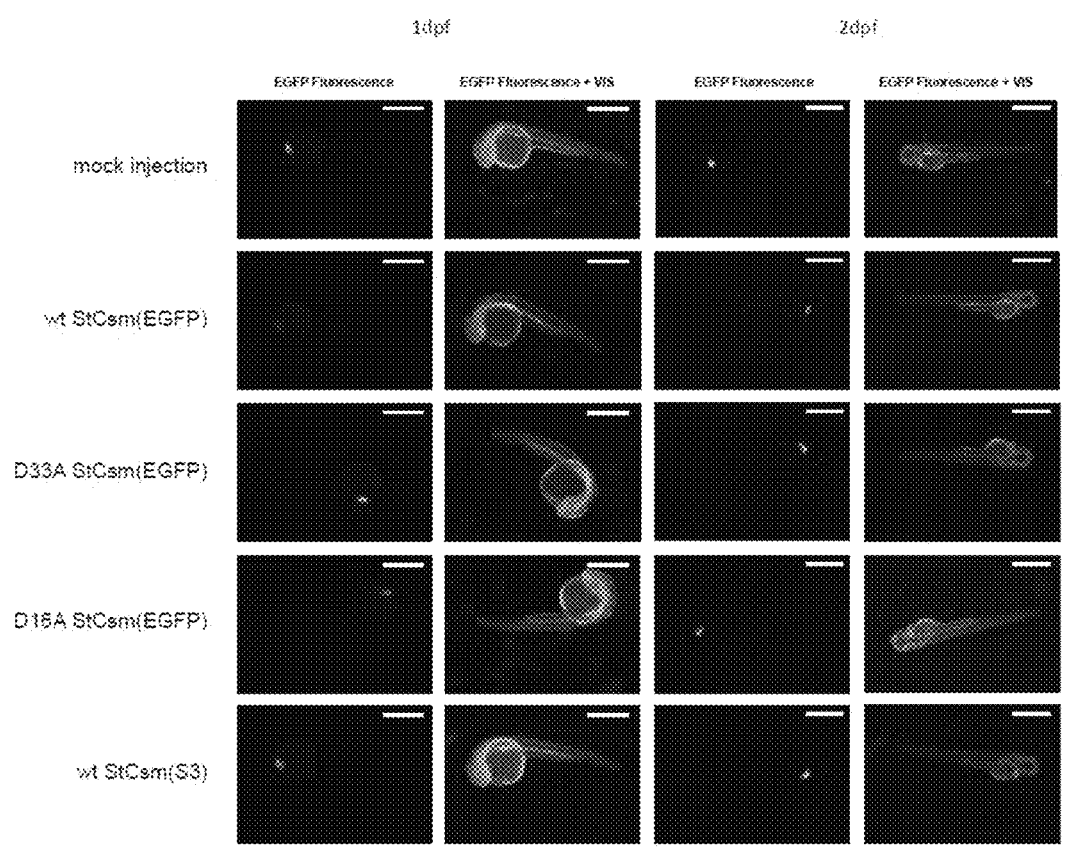
FIG. 37 shows the effects of the injection of StCsm crRNA complexes into cmcl2:EGFP embyros.

The nkx2.5:EGFP and cmcl2:EGFP fish exhibit fluorescence in the heart. Knockdown efficiency of the nkx2.5:EGFP and cmcl2:EGFP lines was quantified by counting the number of highly fluorescent cells (50-fold more fluorescent than background). A knockdown of 30-40% was detected in the nkx:2.5:EGFP fish upon StCsm(EGFP) injection by FACS (FIG. 24C). This reduction in EGFP fluorescence was not detectable by imaging. (FIG. 36). A stronger, four-fold fluorescence reduction could be achieved in the cmcl2:EGFP line at 1 dpf (FIG. 24D and FIG. 37). As the controls with the D16A and D33 Csm(EGFP) variants showed, the reduction of fluorescence was almost exclusively due to the RNase activity of the StCsm(EGFP) complex in both cases. At 2 dpf, the effect of knockdown had essentially faded away.

Figure 38:
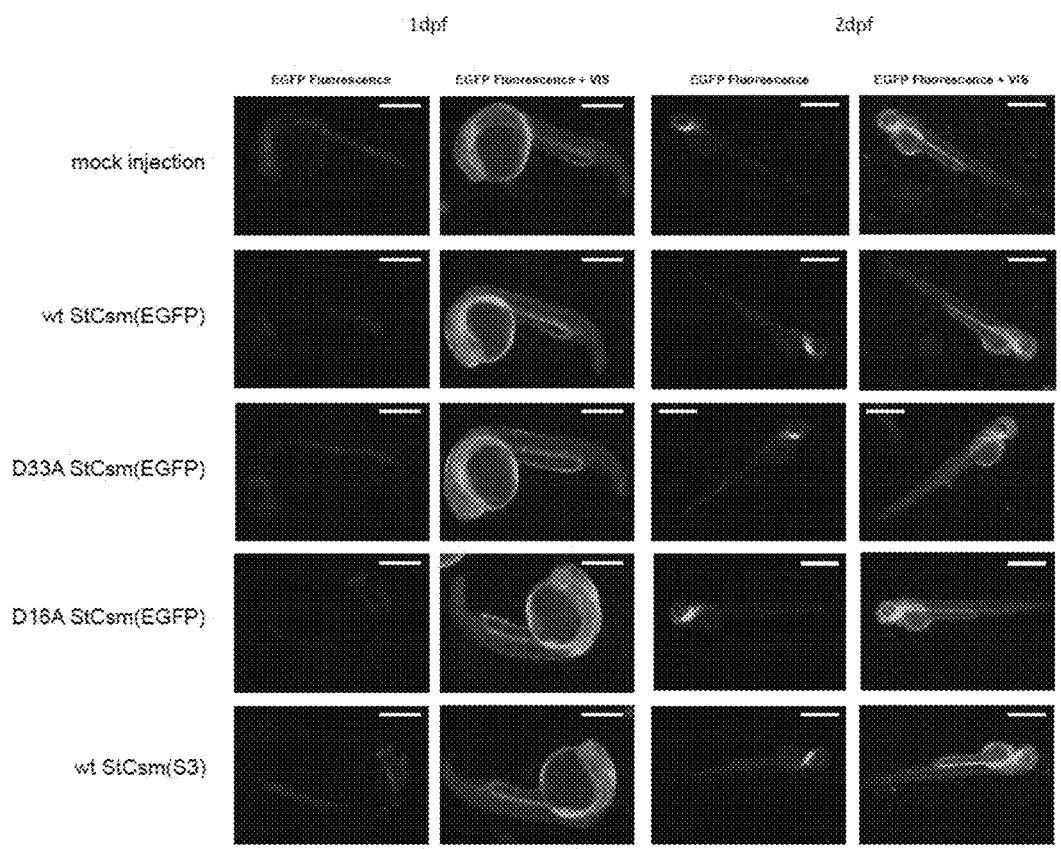
FIG. 38 shows the effects of the injection of StCsm crRNA complexes into fli1:EGFP embyros.

The fli1:EGFP fish exhibit fluorescent vasculature throughout the embryo. Therefore, knockdown efficacy was quantified by mean fluorescence in this case. At 1 dpf, more than 50% knockdown was achieved using the wt StCsm (EGFP) complex. The reduction of EGFP fluorescence was slightly lower with the D16A variant, raising the possibility that the DNase activity of the Csm complex may have contributed the reduction of fluorescence. However, the RNase deficient version of the complex did was ineffective. At 2 dpf, knockdown effects were reduced to statistically insignificant levels (FIG. 24E and FIG. 38).

Low StCsm(EGFP) Toxicity

Figure 39:
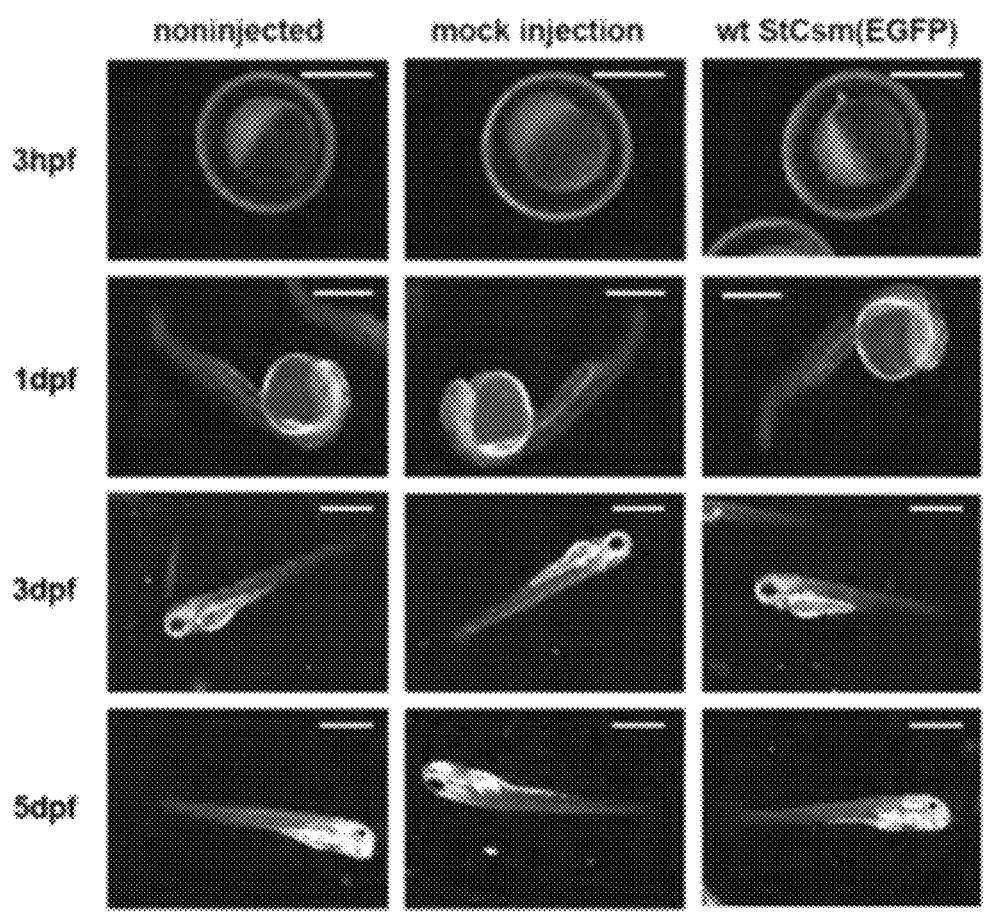
FIG. 39 depicts the lack of toxicity of StCsm(EGFP) complexes. The complexes were injected at 5-fold higher concentration than used for knockdown experiments. No changes of phenotypes were observed.

To check the toxicity of StCsm(EGFP), higher amounts than required for knock-down were injected into 1 cell stage embryos. A low rate of developmental defects was also observed in mock-injected embryos due to mechanical disruption of the embryos at injection. Injection of the wt StCsm(EGFP), even at a concentration five times higher than the concentration used in actual knockdown experiments, did not increase this low rate of defects. Up to 5 dpf (the last time point monitored due to legal restrictions), the StCsm(EGFP) fish did not exhibit any developmental defects. StCsm mediated knockdown has a low toxicity and may be superior in this respect to morpholino-mediated knockdown (FIG. 39).

Csm Mediated Knockdown is Best for Maternally Deposited RNAs

Csm mediated RNA knockdown worked best for the exclusively maternal EGFP transcript generated under the control of the vasa promoter. The knockdown for transcripts expressed in the zygote was less pronounced than for the maternally deposited RNA, and the effect decreased over time. Observation of significant knockdown effects for the cmcl2 and flit promoter driven EGFP transcripts strongly suggested that the Csm bound crRNA survives the widespread RNA degradation during the maternal to zygotic transition (MZT) at 3.5 hpf, most likely due to protection of the crRNA along its entire length by the Csm complex (Tamulaitis et al. 2014). With the exception of the nkx2.5 line, according to FACS analysis, more than 50% EGFP fluorescence was left. As most vertebrate genes are haplosufficient (Huang et al. 2010, Neuhauss et al. 1999), this efficiency may not be enough to elicit phenotypes. This limitation can likely be overcome.

The Csm DNase activity did not contribute much to the extinction of fluorescence in all cases, also for the zygotically expressed transcripts. This could be due to exclusion of the StCsm complex from the nucleus due its large size and the absence of a nuclear localization signal, or it could reflect the faster RNA than DNA degradation, as seen in the test tube (compare FIGS. 26B and 27B). It is hypothesized that with the addition of a nuclear localization signal, the dual DNase and RNase activities of the Csm complexes could be exploited to achieve more permanent reduction in fluorescence, at the cost of double strand breaks and endangered genome integrity.

Comparison with Morpholino-Based Knockdown

In zebrafish, the leading technology for RNA silencing is with morpholino antisense oligonucleotide analogues ("morpholinos") (Bill et al. 2009, Nasevicius et al. 2000, Heasman et al. 2002). Despite its usefulness, morpholino mediated knockdown has some severe limitations. As morpholinos only bind to RNA but do not induce its degradation, only translation initiation and splice sites can be targeted, which is not always uniquely possible. Morpholinos have a low "useful" range of concentrations. At lower concentration, silencing is frequently incomplete (Eisen et al. 2008). At higher concentration, off-target effects are common and have to be carefully controlled (Stainier et al. 2015, Kok et al. 2015). In contrast, the crRNA Csm based knockdown strategy is catalytic, and appears to be relatively non-toxic, judging from the high concentration of crRNA Csm complex that can be injected without apparent phenotypes and also specific judging from the absence of knockdown effects with the jGFP crRNA guide. However, the effect of crRNA Csm complexes wears off relatively quickly, perhaps due to degradation of the crRNA or of Csm proteins, whereas morpholino mediated knockdown is more persistent.

Comparison with Argonaute Based Knockdown

The zebrafish endogenous RNA interference pathway could in principle be highjacked to experimentally knockdown genes. However, esiRNA has been reported to lead to non-specific developmental interference in zebrafish embryos (Liu et al. 2005), presumably due to overload of the endogenous interference pathways. More encouraging results have been obtained using either siRNA (Liu et al. 2005) or shRNA (De Rienzo et al. 2012), but neither method has gained widespread acceptance in the zebrafish community.

An attractive alternative to endogenous Argonaute (Ago) proteins are heterologous Agos with usual requirements for the guide nucleic acid, such as Marinitoga piezophila Ago (MpAgo) that requires a 5'-non-phosphorylated guide RNA (Kaya et al. 2016). The *Natronobacterium gregoryi* Ago (NgAgo) is the only heterologous Ago that has been tested as a tool for gene knockdown in zebrafish. This Ago was originally reported as a DNA directed DNA endonuclease (Gao et al. 2016), but this activity could not be confirmed (Burgess et al. 2017, Lee et al. 2017) and the original report has now been retracted. Instead, new data suggest that the NgAgo may be a DNA guided, RNA directed endonuclease (Ye Sunghyeok et al. 2017; https://doi.org/10.1101/101923). To date, NgAgo has been used in zebrafish to knock down the fabp11a mRNA, causing eye developmental defects (Qi et al. 2016). As fabp11a mRNA is expressed similarly early as the zygotically expressed EGFPs in this study, and as only a single gene has been studied, it is not yet possible to compare efficacies. Observation of a phenotype may suggest a better than 50% knockdown efficiency for NgAgo in the case of fabp11a, but this has not yet been rigorously tested. The enzymatic Csm and NgAgo based approaches to RNA knockdown are likely to have similar advantages compared to the morpholino approach. On the one hand, NgAgo has the advantage over Csms that the guide can be loaded in a test tube, but this may change if an in vitro loadable version of the Csm complex can be developed. On the other hand, NgAgo with its DNA guide may endanger genome stability more than a DNase deficient Csm complex with its RNA guide. NgAgo cuts RNA at a single site whereas Csm complexes make multiple cuts in a target RNA. Whether this difference matters in the background of a host such as zebrafish that has pathways for the degradation of uncapped or non-polyadenylated mRNAs remains to be explored.

The following methods were used.

EGFP and jGFP Sequences

The target regions of the mRNAs of jellyfish (*Aequorea victoria*) jGFP and zebrafish EGFP used span nucleotides 241-276. In this region, the coding strands have the DNA sequences 5'-CATGACTTTTTCAAGAGTGC-CATGCCCGAAGGTTAT-3' (SEQ ID NO: 131) and 5'-CACGACTTCTTCAAGTCCGCCATGCCCGAAGGC-TAC-3' (SEQ ID NO: 132) differing in seven positions (underlined).

CRISPR Regions and crRNAs

Artificial CRISPR loci were created that contained four identical 36 nucleotide spacers separated by 36 nucleotide repeats. The sequences of the repeats were taken from the Csm associated CRISPR cluster of *S. thermophilus* DGCC8004. Spacer sequences were exact complements of the targeted region of EGFP, jGFP, or S3 RNA. In the expression cells, the pre-crRNAs are initially cleaved to 72 nucleotide long crRNA, which may be then be trimmed to 40 nucleotide long matured crRNAs with 32 nucleotides of spacer sequence (Tamulaitis et al. 2014).

Cloning, Expression and Purification of StCsm Complexes

Wt and mutant *Streptococcus thermophilus* Csm (StCsm) complexes were obtained as described previously (Tamulaitis et al. 2014). Briefly, *Escherichia coli* ER2566 (DE3) was transformed with three plasmids: (i) plasmid pCas/Csm which contains a cassette including all the cas/csm genes (except cas1 and cas2), (ii) plasmid pCRISPR which contains four identical tandem copies of the repeat-spacer unit flanked by the leader sequence and the terminal repeat, (iii) plasmid pCsm2-Tag which contains a N-terminal-StrepII-tagged variant of csm2 gene. Next, the ER2566 (DE3) bearing these plasmids was grown at 37° C. in LB medium supplemented with streptomycin (25 µg/µl), ampicillin (50 µg/µl), and chloramphenicol (30 µg/µl) and expression of wt StCsm complex was induced using 1 mM IPTG. Further, StCsm complex was isolated by subsequent Strep-chelating affinity and size exclusion chromatography steps. The protein composition of the isolated StCsm was analysed by SDS-PAGE Coomassie staining. StCsm complex containing D33A Csm3 and D16A Cas10 mutants were constructed and isolated as described in (Tamulaitis et al. 2014, Kazlauskiene et al. 2016). crRNAs co-purified with StCsm were isolated using phenol:chloroform:isoamylalcohol (25: 24:1 v/v/v) extraction and precipitated with ethanol. crRNAs were separated on a denaturing 15% polyacrylamide gel (PAAG) and depicted with SybrGold (Thermo Scientific) staining.

Zebrafish Strains and Fish Maintenance vasa:EGFP (Krovel et al. 2002) (germline), cmcl2:EGFP (Huang et al. 2003) (heart), nkx-2.5:EGFP (heart) (Witzel et al. 2012) were of ABTL genetic background. The mito: EGFP fish (throughout the embryo) (Kim et al. 2008) were of nacre genetic background (Lister et al. 1999). The fli1: EGFP fish (blood vessels) (Lawson et al. 2002) were of casper genetic background (White et al. 2008). The nucleotide sequence of the EGFP transgenes was confirmed by Sanger sequencing in all cases. All reporter lines also contain wild-type copies of the respective genes. General maintenance, collection, and staging of the zebrafish were performed as described previously (Westerfield et al. 1993). Embryos were maintained in Danieau zebrafish medium and grown at 28° C. The developmental stages were estimated based on time post-fertilization (hours or days; hpf or dpf) at 28° C.

Preparation of DNA and RNA Substrates

Figure 25:
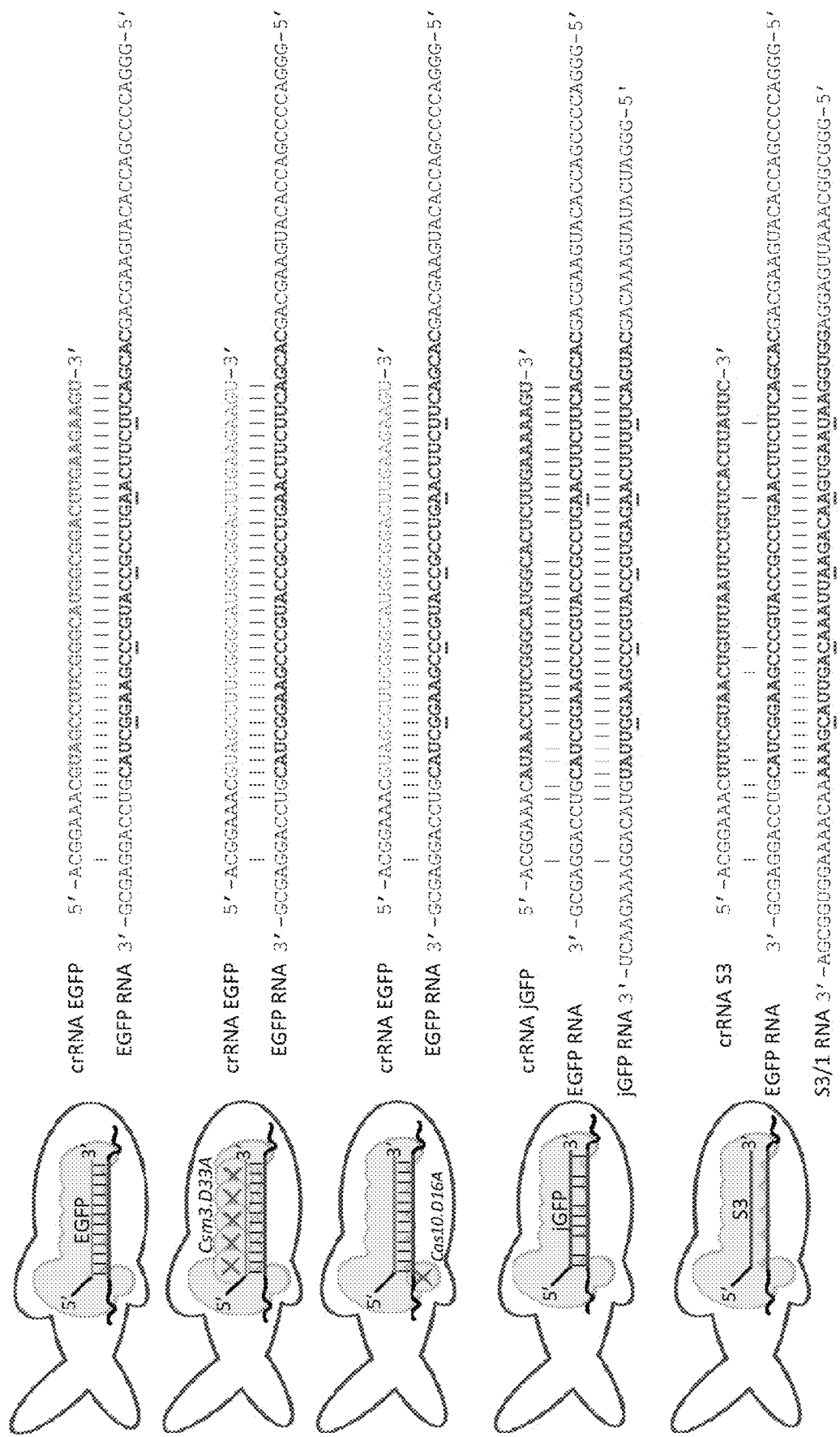
FIG. 25 depicts crRNAs and target RNA sequences. Vertical bars indicate complementary nucleotides in the aligned sequences of crRNAs and RNA substrates. Underlined nucleotides on target RNA indicate cleavage positions of StCsm. Target RNA is cleaved at 5'-position to underlined nucleotide. StCsm complexes with bound EGFP transcript are schematically depicted on the left.

Synthetic oligodeoxynucleotides were purchased from Metabion. All RNA substrates were obtained by in vitro transcription using TranscriptAid T7 High Yield Transcription Kit (Thermo Scientific). Briefly, plasmids pSG1154_jGFP, pUC18_S3/1 and pUC18_EGFP were used as a template to produce different DNA fragments by PCR using appropriate primers containing a T7 promoter in front of the desired RNA sequence. RNA substrates were 5'-labeled with [γ$^{33}$P] ATP (Perkin Elemer) and PNK (Thermo Scientific). Ss M13mp18 plasmid DNA was purchased from New England BioLabs. FIG. 25 provides a full description of RNA substrates.

Cleavage Assay in Vitro

Figure 40A:
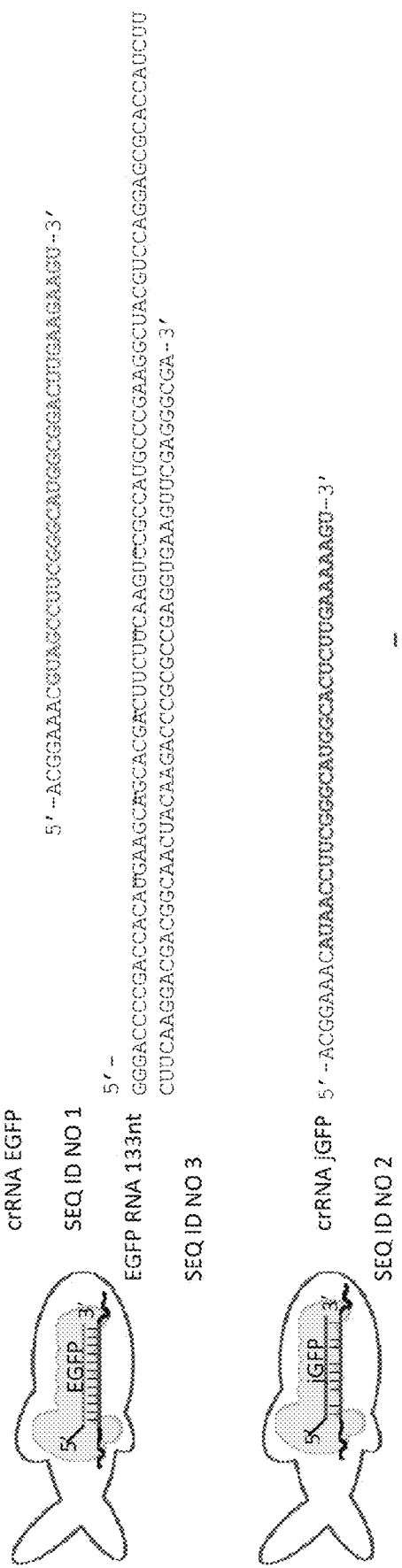
FIGS. 40A, 40B, and 40C illustrate an in vitro RNA cleavage assay performed at low temperature.
Figure 40B:
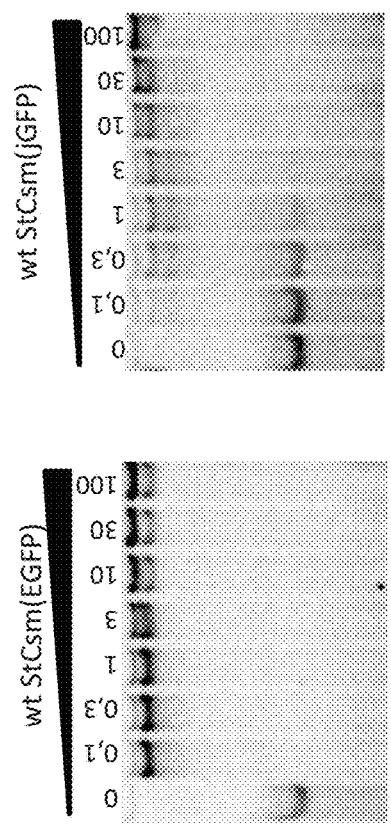
Figure 40C:
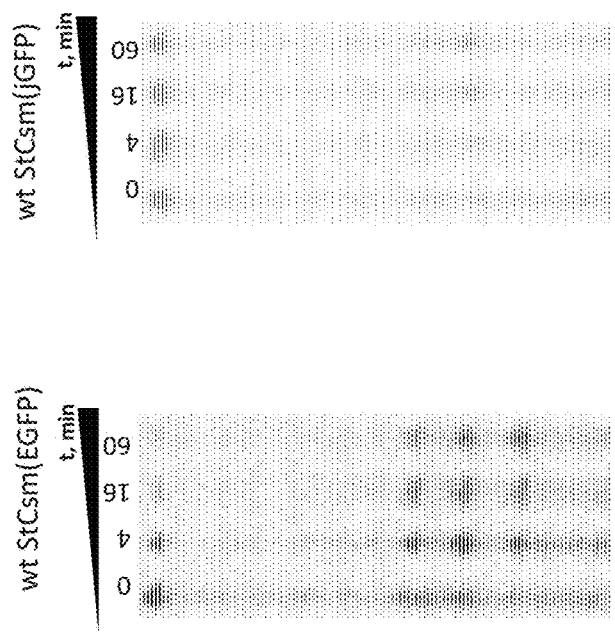

The StCsm RNA cleavage reactions in vitro were performed at 28° C. (or at 15° C. (see FIGS. 40B and 40C) and contained 8 nM of 5'-radiolabeled RNA and 160 nM StCsm in the reaction buffer (33 mM Tris-acetate (pH 7.9 at 25° C.), 66 mM K-acetate, 0.1 mg/ml BSA) supplemented with 10 mM Mg-acetate. Reactions were initiated by addition of the $Mg^{2+}$. The samples were collected at timed intervals and quenched by mixing 5 µl of reaction mixture with 10 µl of phenol:chloroform:isoamylalcohol (25:24:1 v/v/v). The aqueous phase was collected and mixtured with 2×RNA loading buffer (Thermo Scientific) followed by incubation for 7 min at 85° C. The reaction products were separated on a denaturing 15% PAAG and depicted by autoradiography. The StCsm reactions on circular ssDNA in vitro were performed at 28° C. and contained 1 nM M13mp18 ssDNA, 5 nM StCsm, and 5 nM RNA in the reaction buffer supplemented with 10 mM $MnCl_2$. Reactions were initiated by addition of $Mn^{2+}$. The samples were collected at timed intervals and quenched by mixing 5 µl of reaction mixture with 2× loading dye (98% formaldehyde, 25 mM EDTA, 0.025% bromophenol blue), followed by incubation for 7 min at 85° C. The reaction products were separated during 1% agarose gel electrophoresis in TAE buffer (40 mM Tris, 5 mM CH3COONa, 0.9 mM EDTA, pH 7.9), stained with SYBR Gold (Thermo Scientific) and visualized using Fluorescent Image Analyzer FLA-2000 (Fuji Photo Film, Japan).

Microinjection

Freshly laid fertilized eggs (or embryos) were collected from breeding tanks and injected with 1 nl of 0.5 mg/ml StCsm complex into the yolk of one cell stage embryos using an Eppendorf FemtoJet microinjection setup. The embryos were incubated afterwards at 28° C.

Microscopy

Embryos were anaesthetized using tricaine. Fluorescence from live embryos was observed using a Leica M165FC fluorescent microscope equipped with a Leica DFC450C digital camera.

Flow Cytometry Analysis

About 20-30 embryos at 48 hpf were collected and washed twice with Hank's solution. The embryos were minced in a Petri dish with a fine scalpel. 800 µl of 0.25% trypsin were added and mixed at 500 rpm on a bench top shaker for 1 h at RT. The cells were filtered through a 40 µm cell strainer and washed 3 times with Hank's solution. The remaining was centrifuged at 2000 rpm. The pellet was resuspended in 500 µl Hank's solution and analyzed for EGFP fluorescence by BD FACS Calibur.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

The application contains a Sequence Listing which has been submitted electronically in ASCII format and is hereby incorporated by reference in its entirety. Said ASCII copy, created on Nov. 24, 2015, is named 078981.25_SL.txt and is 49.9 kilobytes in size.

Each of the following references is expressly incorporated by reference herein in its entirety:

Kok et al. (2015) Reverse genetic screening reveals poor correlation between morpholino-induced and mutant phenotypes in zebrafish. Dev Cell, 32, 97-108.

Rossi et al. (2015) Genetic compensation induced by deleterious mutations but not gene knockdowns. Nature, 524, 230-233.

Abudayyeh et al. (2016) C2c2 is a single-component programmable RNA-guided RNA-targeting CRISPR effector. Science, 353, aaf5573.

Shmakov et al. (2015) Discovery and Functional Characterization of Diverse Class 2 CRISPR-Cas Systems. Mol Cell, 60, 385-397.

East-Seletsky et al. (2016) Two distinct RNase activities of CRISPR-C2c2 enable guide-RNA processing and RNA detection. Nature, 538, 270-273.

Staals et al. (2014) RNA targeting by the type III-A CRISPR-Cas Csm complex of Thermus thermophilus. Mol Cell, 56, 518-530.

Tamulaitis et al. (2014) Programmable RNA shredding by the type III-A CRISPR-Cas system of Streptococcus thermophilus. Mol Cell, 56, 506-517.

Hale et al. (2009) RNA-guided RNA cleavage by a CRISPR RNA-Cas protein complex. Cell, 139, 945-956.

Zhang et al. (2012) Structure and mechanism of the CMR complex for CRISPR-mediated antiviral immunity. Mol Cell, 45, 303-313.

Rouillon et al. (2013) Structure of the CRISPR interference complex CSM reveals key similarities with cascade. Mol Cell, 52, 124-134.

Marraffini and Sontheimer (2008) CRISPR interference limits horizontal gene transfer in staphylococci by targeting DNA. Science, 322, 1843-1845.

Goldberg et al. (2014) Conditional tolerance of temperate phages via transcription-dependent CRISPR-Cas targeting. Nature, 514, 633-637.

Kazlauskiene et al. (2016) Spatiotemporal Control of Type III-A CRISPR-Cas Immunity: Coupling DNA Degradation with the Target RNA Recognition. Mol Cell, 62, 295-306.

Samai et al. (2015) Co-transcriptional DNA and RNA Cleavage during Type III CRISPR-Cas Immunity. Cell, 161, 1164-1174.

Jung et al. (2015) Crystal structure of the Csm1 subunit of the Csm complex and its single-stranded DNA-specific nuclease activity. Structure, 23, 782-790.

Hatoum-Aslan et al. (2011) Mature clustered, regularly interspaced, short palindromic repeats RNA (crRNA) length is measured by a ruler mechanism anchored at the precursor processing site. Proc Natl Acad Sci USA, 108, 21218-21222.

Hatoum-Aslan et al. (2013) A ruler protein in a complex for antiviral defense determines the length of small interfering CRISPR RNAs. J Biol Chem, 288, 27888-27897.

Krovel and Olsen (2002) Expression of a vas::EGFP transgene in primordial germ cells of the zebrafish. Mech Dev, 116, 141-150.

Kim et al. (2008) Real-time imaging of mitochondria in transgenic zebrafish expressing mitochondrially targeted GFP. Biotechniques, 45, 331-334.

Witzel et al. (2012) The LIM protein Ajuba restricts the second heart field progenitor pool by regulating Isl1 activity. Dev Cell, 23, 58-70.

Huang et al. (2003) Germ-line transmission of a myocardium-specific GFP transgene reveals critical regulatory elements in the cardiac myosin light chain 2 promoter of zebrafish. Dev Dyn, 228, 30-40.

Lawson and Weinstein (2002) In vivo imaging of embryonic vascular development using transgenic zebrafish. Dev Biol, 248, 307-318.

Knaut et al. (2002) An evolutionary conserved region in the vasa 3'UTR targets RNA translation to the germ cells in the zebrafish. Curr Biol, 12, 454-466.

Knaut et al. (2000) Zebrafish vasa RNA but not its protein is a component of the germ plasm and segregates asymmetrically before germline specification. J Cell Biol, 149, 875-888.

Braat et al. (2000) Vasa protein expression and localization in the zebrafish. Mech Dev, 95, 271-274.

Chen and Fishman (1996) Zebrafish tinman homolog demarcates the heart field and initiates myocardial differentiation. Development, 122, 3809-3816.

Braat et al. (1999) Characterization of zebrafish primordial germ cells: morphology and early distribution of vasa RNA. Dev Dyn, 216, 153-167.

Huang et al. (2010) Characterising and predicting haploinsufficiency in the human genome. PLoS Genet, 6, e1001154.

Neuhauss et al. (1999) Genetic disorders of vision revealed by a behavioral screen of 400 essential loci in zebrafish. J Neurosci, 19, 8603-8615.

Bill et al. (2009) A primer for morpholino use in zebrafish. Zebrafish, 6, 69-77.

Nasevicius and Ekker (2000) Effective targeted gene 'knockdown' in zebrafish. Nat Genet, 26, 216-220.

Heasman (2002) Morpholino oligos: making sense of antisense? Dev Biol, 243, 209-214.

Eisen and Smith (2008) Controlling morpholino experiments: don't stop making antisense. Development, 135, 1735-1743.

Stainier et al. (2015) Making sense of anti-sense data. Dev Cell, 32, 7-8.

Liu et al. (2005) Efficient RNA interference in zebrafish embryos using siRNA synthesized with SP6 RNA polymerase. Dev Growth Differ, 47, 323-331.

De Rienzo et al. (2012) Efficient shRNA-mediated inhibition of gene expression in zebrafish. Zebrafish, 9, 97-107.

Kaya et al. (2016) A bacterial Argonaute with noncanonical guide RNA specificity. Proc Natl Acad Sci USA, 113, 4057-4062.

Gao et al. (2016) DNA-guided genome editing using the Natronobacterium gregoryi Argonaute. Nat Biotechnol, 34, 768-773.

Burgess et al. (2017) Questions about NgAgo (vol 7, pg 913, 2016). Protein Cell, 8, 77-77.

Lee et al. (2017) Failure to detect DNA-guided genome editing using Natronobacterium gregoryi Argonaute. Nature Biotechnology, 35, 17-18.

Qi et al. (2016) NgAgo-based fabp11a gene knockdown causes eye developmental defects in zebrafish. Cell Res, 26, 1349-1352.

Lister et al. (1999) nacre encodes a zebrafish microphthalmia-related protein that regulates neural-crest-derived pigment cell fate. Development, 126, 3757-3767.

White et al. (2008) Transparent adult zebrafish as a tool for in vivo transplantation analysis. Cell Stem Cell, 2, 183-189.

Westerfield (1993) The zebrafish book: a guide for the laboratory use of zebrafish (Brachydanio rerio). M. Westerfield, Eugene, Oreg.

Tamulaitis et. al (2017) Type III CRISPR-Cas Immunity: Major Differences Brushed Aside. *Trends in Microbiology* 25(1), 49-61.

Altschul et al. (1997). Gapped BLAST and PSI-BLAST: a new generation of protein database search programs. Nucleic Acids Res 25, 3389-3402.

Ashkenazy et al. (2010). ConSurf 2010: calculating evolutionary conservation in sequence and structure of proteins and nucleic acids. Nucleic Acids Res 38, W529-533.

Baker et al. (2001). Electrostatics of nanosystems: application to microtubules and the ribosome. Proc Natl Acad Sci USA 98, 10037-10041.

Dickman and Hornby (2006). Enrichment and analysis of RNA centered on ion pair reverse phase methodology. RNA 12, 691-696.

Fischer et al. (2010). Determination of the molecular weight of proteins in solution from a single small-angle X-ray scattering measurement on a relative scale. J Appl Crystallogr 43, 101-109.

Frickey and Lupas (2004). CLANS: a Java application for visualizing protein families based on pairwise similarity. Bioinformatics 20, 3702-3704.

Horvath and Barrangou (2010). CRISPR/Cas, the immune system of bacteria and archaea. Science 327, 167-170.

Hrle et al. (2013). Structure and RNA-binding properties of the type III-A CRISPR-associated protein Csm3. RNA biology 10, 1670-1678.

Katoh et al. (2002). MAFFT: a novel method for rapid multiple sequence alignment based on fast Fourier transform. Nucleic Acids Res 30, 3059-3066.

Kozin and Svergun (2001). Automated matching of high- and low-resolution structural models. J Appl Crystallogr 33, 33-41.

Kraulis (1991). MOLSCRIPT: A program to produce both detailed and schematic plots of protein structures. J Appl Crystallogr 24, 945-950.

Makarova et al. (2006). Comparative genomics of the lactic acid bacteria. Proc Natl Acad Sci USA 103, 15611-15616.

Merritt and Bacon (1997). Raster3D: Photorealistic molecular graphics. Methn Enzymol 277, 505-524.

Millen et al. (2012). Mobile CRISPR/Cas-mediated bacteriophage resistance in Lactococcus lactic. PLoS One 7, e51663.

Petoukhov et al. (2012). New developments in the ATSAS program package for small-angle scattering data analysis. J Appl Crystallogr 45, 342-350.

Schrodinger LLC (2010). The PyMOL Molecular Graphics System, Version 1.3r1.

Söding et al. (2005). The HHpred interactive server for protein homology detection and structure prediction. Nucleic Acids Res 33, W244-248.

Staals et al. (2013). Structure and activity of the RNA-targeting Type III-B CRISPR-Cas complex of *Thermus thermophilus*. Mol Cell 52, 135-145.

Svergun (1992). Determination of the regularization parameter in indirect-transform methods using perceptual criteria. J Appl Crystallogr 25, 495-503

Svergun (1999). Restoring low resolution structure of biological macromolecules from solution scattering using simulated annealing. Biophysical journal 2879-2886.

Volkov and Svergun (2003). Uniqueness of it ab initio shape determination in small-angle scattering. J Appl Crystallogr 36, 860-864.

Waghmare et al. (2009). Studying the mechanism of RNA separations using RNA chromatography and its application in the analysis of ribosomal RNA and RNA:RNA interactions. Journal of chromatography. A 1216, 1377-1382.

Zheng et al. (2004). An efficient one-step site-directed and site-saturation mutagenesis protocol. Nucleic Acids Res 32, el 15.

Brouns et al. (2008). Small CRISPR RNAs guide antiviral defense in prokaryotes. Science 321, 960-964.

Carte et al. (2008). Cas6 is an endoribonuclease that generates guide RNAs for invader defense in prokaryotes. Genes & development 22, 3489-3496.

Deng et al. (2013). A novel interference mechanism by a type IIIB CRISPR-Cmr module in Sulfolobus. Molecular microbiology 87, 1088-1099.

Gasiunas et al. (2012). Cas9-crRNA ribonucleoprotein complex mediates specific DNA cleavage for adaptive immunity in bacteria. Proc Natl Acad Sci USA 109, E2579-2586.

Hatoum-Aslan et al. (2014). Genetic characterization of antiplasmid immunity through a type III-A CRISPR-Cas system. J Bacteriol 196, 310-317.

Jinek et al. (2012). A programmable dual-RNA-guided DNA endonuclease in adaptive bacterial immunity. Science 337, 816-821.

Makarova et al. (2011a). Unification of Cas protein families and a simple scenario for the origin and evolution of CRISPR-Cas systems. Biology direct 6, 38.

Makarova et al. (2011b). Evolution and classification of the CRISPR-Cas systems. Nature reviews. Microbiology 9, 467-477.

Marraffini and Sontheimer (2010). CRISPR interference: RNA-directed adaptive immunity in bacteria and archaea. Nature reviews. Genetics 11, 181-190.

Mojica et al. (2009). Short motif sequences determine the targets of the prokaryotic CRISPR defence system. Microbiology 155, 733-740.

Olsthoorn and van Duin (2011). Bacteriophages with ssRNA. In eLS (John Wiley & Sons Ltd, Chichester).

Sinkunas et al. (2013). In vitro reconstitution of Cascade-mediated CRISPR immunity in *Streptococcus thermophilus*. EMBO J 32, 385-394.

Spilman et al. (2013). Structure of an RNA silencing complex of the CRISPR-Cas immune system. Mol Cell 52, 146-152.

Sternberg et al. (2014). DNA interrogation by the CRISPR RNA-guided endonuclease Cas9. Nature 507, 62-67.

Szczelkun et al. (2014). Direct observation of R-loop formation by single RNA-guided Cas9 and Cascade effector complexes. Proc Natl Acad Sci USA 111, 9798-9803.

Terns and Terns (2014). CRISPR-based technologies: prokaryotic defense weapons repurposed. Trends in genetics: TIG 30, 111-118.

Westra et al. (2012). CRISPR immunity relies on the consecutive binding and degradation of negatively supercoiled invader DNA by Cascade and Cas3. Mol Cell 46, 595-605.

Wiedenheft et al. (2011). Structures of the RNA-guided surveillance complex from a bacterial immune system. Nature 477, 486-489.

TABLE 1

(related to FIG. 1).
Protein identified following mass spectrometry analysis of StCsm-72.

| Protein | Mass (Da) | Score | Coverage (%) | Peptides | SEQ ID NO: |
|---|---|---|---|---|---|
| Cas10 | 86891 | 1076 | 36 | LAYYLTR | 2 |
|  |  |  |  | GDYAAIATR | 3 |
|  |  |  |  | VYINQFASDK | 4 |
|  |  |  |  | TVETLVQFEK | 5 |
|  |  |  |  | YFKPTVLNLK | 6 |
|  |  |  |  | YHMANYQSDK | 7 |
|  |  |  |  | HNYKEDLFTK | 8 |
|  |  |  |  | LYVAFGWGSFAAK | 9 |
|  |  |  |  | DSISLFSSDYTFK | 10 |
|  |  |  |  | DIMSELNSPESYR | 11 |
| Csm3 | 24541 | 768 | 46 | ITAEANPR | 12 |
|  |  |  |  | FENTIDR | 13 |
|  |  |  |  | TLNELLTAEV | 14 |
|  |  |  |  | AT11/FGNYDVK | 15 |
|  |  |  |  | LLELDYLGGSGSR | 16 |
|  |  |  |  | LKATTVFGNYDVK | 17 |
| Csm4 | 33727 | 584 | 33 | KQDLYK | 18 |
|  |  |  |  | IFSALVLESLK | 19 |
|  |  |  |  | DGNLYQVATTR | 20 |
|  |  |  |  | HDQIDQSVDVK | 21 |
| Cas6 | 28240 | 197 | 16 | LVFTFK | 22 |
|  |  |  |  | LIFQSLMQK | 23 |
| Csm2 | 14817 | 186 | 21 | AQILEALK | 24 |
|  |  |  |  | VQFVYQAGR | 25 |
| Csm5 | 41013 | 138 | 12 | LISFLNDNR | 26 |
|  |  |  |  | NHESFYEMGK | 27 |

TABLE 2

(related to FIG. 1):
Proteins identified following mass spectrometry analysis of StCsm-40.

| Protein | Mass (Da) | Score | coverage (%) | Peptides | SEQ ID NO: |
|---|---|---|---|---|---|
| Cas10 | 86891 | 1149 | 30 | LAYYLTR | 2 |
|  |  |  |  | GDYAAIATR | 3 |
|  |  |  |  | VYINQFASDK | 4 |
|  |  |  |  | YFKPTVLNLK | 6 |
|  |  |  |  | YFFNHQDER | 28 |
|  |  |  |  | YHMANYQSDK | 7 |
|  |  |  |  | HNYKEDLFTK | 8 |
|  |  |  |  | LYVAFGWGSFAAK | 9 |
|  |  |  |  | DSISLFSSDYTFK | 10 |
|  |  |  |  | DIMSELNSPESYR | 11 |
|  |  |  |  | IDLFYGALLHDIGK | 29 |
|  |  |  |  | DFNQFLLANFQTR | 30 |

TABLE 2-continued (related to FIG. 1):
Proteins identified following mass
spectrometry analysis of StCsm-40.

| Protein | Mass (Da) | Score | coverage (%) | Peptides | SEQ ID NO: |
|---|---|---|---|---|---|
| | | | | FITNVYDDKLEQIR | 31 |
| | | | | EKIDLFYGALLHDIGK | 32 |
| | | | | GNEKDSISLFSSDYTFK | 33 |
| | | | | IWDTYTNQADIFNVFGAQTDK | 34 |
| | | | | SKPNFASATYEPFSKGDYAAIATR | 35 |
| | | | | IWDTYTNQADIFNVFGAQTDKR | 36 |
| | | | | HALVGADWFDEIADNQVISDQIR | 37 |
| Csm3 | 24541 | 801 | 57 | ITAEANPR | 12 |
| | | | | FENTIDR | 13 |
| | | | | TLNELLTAEV | 14 |
| | | | | ATTVFGNYDVK | 15 |
| | | | | LLELDYLGGSGSR | 16 |
| | | | | LKATTVFGNYDVK | 17 |
| | | | | VAEKPSDDSDILSR | 38 |
| | | | | DPITNLPIIPGSSLK | 39 |
| | | | | SYTEVKFENTIDR | 40 |
| | | | | DAFLSNADELDSLGVR | 41 |
| | | | | FENTIDRITAEANPR | 42 |
| | | | | NSTFDFELIYEITDENENQVEEDFK | 43 |
| Csm4 | 33727 | 554 | 33 | KQDLYK | 18 |
| | | | | IFSALVLESLK | 19 |
| | | | | DGNLYQVATTR | 20 |
| | | | | HDQIDQSVDVK | 21 |
| | | | | SSGFAFSHATNENYR | 44 |
| | | | | FELDIQNIPLELSDR | 45 |
| | | | | FELDIQNIPLELSDRLTK | 46 |
| | | | | NQPHKDGNLYQVATTR | 47 |
| | | | | SSGFGEFELDIQNIPLELSDR | 48 |
| Csm6 | 28240 | 171 | 16 | LVFTFK | 22 |
| | | | | LIFQSLMQK | 23 |
| | | | | RIDHPAQDLAVK | 49 |
| | | | | SQGSYVIFPSMR | 50 |
| Csm2 | 14817 | 110 | | AQILEALK | 24 |
| | | | | VQFVYQAGR | 25 |
| Csm5 | 41013 | 965 | 50 | WDYSAK | 51 |
| | | | | QADGILQR | 52 |
| | | | | EFIYENK | 53 |
| | | | | FYFPDMGK | 54 |
| | | | | TILMNTTPK | 55 |
| | | | | KFYFPDMGK | 56 |
| | | | | VSDSKPFDNK | 57 |
| | | | | LISFLNDNR | 26 |
| | | | | NHESFYEMGK | 27 |
| | | | | EYDDLFNAIR | 58 |
| | | | | WNNENAVNDFGR | 59 |
| | | | | GKEYDDLFNAIR | 60 |
| | | | | KGKEYDDLFNAIR | 61 |
| | | | | IEFEITTTTDEAGR | 62 |
| | | | | LSLLTLAPIHIGNGEK | 63 |
| | | | | DAFGNPYIPGSSLK | 64 |
| | | | | LAEKFEAFLIQTRPNAR | 65 |

TABLE 3

(related to FIG. 1): Mw estimations
for StCsm-40 and StCsm-72 by different methods.

| | SDS-PAGE, kDa* | DLS, kDa** | Mo W server, kDa*** | Porod volume, kDa*** | DAMMIN models, kDa**** |
|---|---|---|---|---|---|
| Csm-40 | 344.8 | 305 ± 75 | 302 ± 9 | 282 ± 15 | 347.5 |
| Csm-72 | 486.2 | 523 ± 128 | 425 ± 15 | 350 ± 9 | 465.6 |

*Molecular mass calculated from evaluation of the complex composition by densitometric analysis of the SDS-PAGE gels.
**Molecular mass calculated from dynamic light scattering (DLS) analysis.
***Molecular mass calculated from the SAXS data by the method described in (Fischer et al., 2010) using the SAXS Mo W program run on the server http://www.if.sc.usp.br/~saxs/saxsmow.html.
****Molecular mass was estimated using the Porod volumes calculated from SAXS data and excluded volumes of DAMMIN models as described in (Petoukhov et al., 2012).

TABLE 4

(related to FIG. 1): SAXS data collection details and structural parameters of StCsm-40 and StCsm-72 complexes.

| Data collection parameters | |
|---|---|
| Beam line | P12 |
| Wavelength, nm | 0.124 |
| Sample to detector distance, m | 3.1 |
| Detector | Pilatus 2M |
| s range, nm$^{-1}$ | 0.975786-4.665330 |
| exposure time of each frame, s | 0.05 |
| Frames collected | 20 |
| Sample storage temperature, °C. | 10 |
| Cell temperature, °C. | 20 |

| Structural parameters | | | | | | |
|---|---|---|---|---|---|---|
| | Csm-40 | | | Csm-72 | | |
| Sample concentrations, mg/ml | 0.13 | 0.52 | 1.34 | 0.20 | 0.65 | 2.00 |
| Guinier range (first-last point) as calculated by AUTORG | 14-53 | 26-55 | 19-52 | 8-35 | 21-39 | 11-34 |
| P(r) calculation range, Å$^{-1}$ | 0.0114-0.2006 | 0.0114-0.2006 | 0.0117-0.1739 | 0.0089-0.1076 | 0.0108-0.1076 | 0.0084-0.1049 |
| Real space Rg, calculated by GNOM, Å | 63.59 ± 0.414 | 62.80 ± 0.329 | 63.20 ± 0.163 | 83.82 ± 0.545 | 81.40 ± 0.333 | 83.14 ± 0.287 |
| Real space Rg calculated by DATGNOM, Å | 64.02 | 62.35 | 63.26 | 84.15 | 81.69 | 84.51 |
| Reciprocal space Rg calculated by DATGNOM, Å | 68.08 | 58.04 | 61.34 | 81.51 | 79.71 | 83.79 |
| Dmax as parameter for GNOM, Å | 210 | 208 | 215 | 275 | 265 | 280 |
| Dmax calcutaled by DATGNOM, Å | 233.2 | 203.1 | 214.7 | 279.2 | 267.0 | 293.3 |
| Porod volume estimated by DATPOROD, Å$^3$ | 452186 | 501468 | 485803 | 611618 | 589997 | 581121 |
| Excluded volume of DAMMIN models, Å$^3$ (10 models averaged) | | 590770 ± 5209 | | | 791440 ± 11366 | |

TABLE 5

(related to FIGS. 2, 3, 4, 5, and 6): Nucleic acid substrates used in this study. TABLE 5 discloses SEQ ID NOS 66-73, 68, 74, 72, 75, 69, 71, 73, 74, 76, 75 and 77-93, 133, 134 and 94-105, respectively, in order of appearance.

| | |
|---|---|
| S3 crRNA in Csm-72 | 5′-handle Spacer S3 3′-handle<br>5′-ACGGAAACUUUCGUAACUGUUUAAUUCUGUUCACUUAUUCCACCGAUAUAAACUUAAUUACCUCGAGAGGGG-3′ |
| S3 crRNA in Csm-40 | 5′-handle Spacer S3<br>5′-ACGGAAACUUUCGUAACUGUUUAAUUCUGUUCACUUAUUC-3′ |

| Substrates | Length, nt | Sequence |
|---|---|---|
| S3/1 DNA/DNA | 76/76 | 5′-GGAGCTCGCCACCTTTGTTTTTCGTAACTGTTTAATTCTGTTCACTTATTCCACCTCCTCAATTTGCCGGCTTGG-3′<br>3′-CCTCGAGCGGTGGAAAACAAAAAGCATTGACAAATTAAGACAAGTGAATAAGGTGGAGGAGTTAAACGGCCGAACC-5′<br>O1205 |
| NS DNA/DNA | 73/73 | 5′-GACCACCCTTTTGATATAATATACCTATATCAATGGCCTCCCACGCATAAGCGCAGATACGTTCTGAGGAA-3′<br>3′-CTGGTGGGAAAAACTATATTATATGGATATAGTTACCGGAGGGTGCGTATTCGCGTCATGCAAGACTCCCTT-5′ |
| S3/2 DNA/DNA | 52/52 | 5′-TTTTTTTTTTCGTAACTGTTTAATTCTGTTCACTTATTCCACCTTATATT-3′<br>3′-AAAAAAAAAAGCATTGACAAATTAAGACAAGTGAATAAGGTGGAATATAAA-5′ |
| S3/1 DNA/RNA | 76/68 | 5′-GGAGCTCGCCACCTTTGTTTTTCGTAACTGTTTAATTCTGTTCACTTATTCCACCTCCTCAATTTGCCGGCTTGG-3′<br>3′-AGCGGUGGAAAACAAAAAGCAUUGACAAAUUAAGACAAGUGAAUAAGGUGGAGGAGUUAAACGGCCGAACC-5′ |
| S3/2 DNA/RNA | 52/68 | 5′-TTTTTTTTTTCGTAACTGTTTAATTCTGTTCACTTATTCCACCTTATATT-3′<br>3′-CCAUGGGAAAAAAAAAGCAUUGACAAAUUAAGACAAGUGAAUAAGGUGGAAUAUAAACCCUAGGG-5′ |
| S3/1 DNA | 76 | 3′-CCTCGAGCGGTGGAAAACAAAAAGCATTGACAAATTAAGACAAGTGAATAAGGTGGAGGAGTTAAACGGCCGAACC-5′<br>O1205 |
| NS DNA | 73 | 3′-CTGGTGGGAAAAACTATATTATATGGATATAGTTACCGGAGGGTGCGTATTCGCGTCTATGCAAGACTCCCTT-5′ |
| S3/2 DNA | 52 | 3′-AAAAAAAAAAGCATTGACAAATTAAGACAAGTGAATAAGGTGGAATATAAA-5′ |
| S3/1 RNA | 68 | 3′-AGCGGUGGAAAACAAAAAGCAUUGACAAAUUAAGACAAGUGAAUAAGGUGGAGGAGUUAAACGGCGGG-5′<br>O1205 |
| NS RNA | 68 | 3′-AGCGGUGGAAAACAACCACCUUAUUCACUUGUCUUAAUUGUCAAUGCUUUAGGAGUUAAACGGCGGG-5′<br>O1205 |

TABLE 5-continued (related to FIGS. 2, 3, 4, 5, and 6): Nucleic acid substrates used in this study. TABLE 5 discloses SEQ ID NOS 66-73, 68, 74, 72, 75, 69, 71, 73, 74, 76, 75 and 77-93, 133, 134 and 94-105, respectively, in order of appearance.

| Name | Length | Sequence |
|---|---|---|
| S3/2 RNA | 68 | 3'-CCAUGGGAAAAAAAAGCAUUGACAAAUUAAGACAAUGAAUAAGGUGAAUAAACCCUAGGGG-5' |
| S3/3 RNA | 68 | 3'-CCAUGGGUGCCUUUGAAAGCAUUGACAAAUUAAGACAAUGAAUAAGGUGAAUAUAACCCUAGGGG-5' |
| S3/4 RNA | 68 | 3'-CCAUGGGAAAAAAAAGCAUUGACAAAUUAAGACAAUGAAUAAGGUGGCUAUAUUUGGAUUAGGGG-5' |
| S3/5 RNA | 68 | 3'-CCAUGGGUGCCUUUGAAAGCAUUGACAAAUUAAGACAAUGAAUAAGGUGAAUAUUUGGAUUAGGGG-5' |
| S3/6 RNA | 86 | 3'-CCAUGGGUGCCUUUGAAAGCAUUGACAAAUUAAGACAAUGAAUAAGGUGCUAUAUUUGGAUUAAUGGAGCUCUCCCCUGCCGGGG-5' |
| S3/7 RNA | 68 | 3'-CCAUGGGAAAAAAAAAUCAUUGACAAAUUAAGACAAUGAAUAAGGUGAAUAAGGUGAAUAAACCCUAGGGG-5' |
| S3/8 RNA | 68 | 3'-CCAUGGGAAAAAAAAGCAUUGACAAAUUAAGACAAUGAAUAAGCAGGAAUAUAAACCCUAGGGG-5' |
| S3/9 RNA | 68 | 3'-CCAUGGGAAAAAAAAGCAUUGACAAAUAUCACAAGUGAAUAAGGUGAAUAAACCCUAGGGG-5' |
| S3/11 RNA | 24 | 3'-GACAAAUUAAGACAAUGAAUGGGG-5' |
| S3/12 RNA | 32 | 3'-AAAGCAUUGACAAAUUAAGACAAGUGAAUGGGG-5' |
| S3/13 RNA | 23 | 3'-AAAGCAUUGACAAAUUAAGAGGGG-5' |
| S3/14 RNA | 48 | 3'-CCAUGGGAAAAAAAAGCAUUGACAAAUUAAGACAAGUGAAUAGGGG-5' |

(+Tc) crRNA in Csm-72 5'-handle Spacer(+Tc) 3'-handle
5'-ACGGAAACACGCCAGCAAGACGUAGCCCAGCGCUCGGCCGCCAGAUAUAAACCUAAUUACCUCGAGAGGGG-3'

(+Tc) crRNA in Csm-40 5'-handle Spacer(+Tc)
5'-ACGGAAACACGCCAGCAAGACGUAGCCCAGCGCGUCGGCC-3'

TABLE 5-continued (related to FIGS. 2, 3, 4, 5, and 6): Nucleic acid substrates used in this study. TABLE 5 discloses SEQ ID NOS 66-73, 68, 74, 72, 75, 69, 71, 73, 74, 76, 75 and 77-93, 133, 134 and 94-105, respectively, in order of appearance.

| | | |
|---|---|---|
| (+Tc) RNA | | 3'-UCGGGAGCGCAGCGCUUGCGGUCGUUCUGCAUCGGUCGUCGCCAGCCGGCGGUACGGCCGCUAUUACGGGG-5' |
| (−Tc) crRNA in Csm-72 | 5'-handle Spacer(−Tc) 3'-handle<br>5'-ACGGAAACUGGCGGCCCGACGCGCGCUGGGCUACGUCUUGCGCUUGCUG-3' | |
| (−Tc) crRNA in Csm-40 | 5'-handle Spacer(−Tc)<br>5'-ACGGAAACUGGCGGCCCGACGCGCGCUGGGCUACGUCUUGCUG-3' | |
| Substrate | Length, nt | Sequence |
| (−Tc) RNA | 68 | 3'-GGUAAUAGCGGCCGCCGUACCGCCGGCUGCCGCCGACCGCCGACCCGAUGCAGAACGACCGCAAGCGCUGCCUCCGGGG-5' |
| GFP crRNA in Csm-40 | 5'-handle Spacer GFP<br>5'-ACGGAAACAUAACCUUCGGGCAUGGCACUCUUGAAAAGU-3' | |
| Substrate | Length, nt | Sequence |
| GFP RNA | 68 | 3'-UCAAGAAAGGACAUGUAUUGGAAGCCCGUACCGUGAGAACGUUUUCAGUACGACAAAGUAUACUAGGG-5' |
| Rep crRNA in Csm-72 | 5'-handle Spacer Rep 3'-handle<br>5'-ACGGAAACCAACGAGCCUAAAUUCAUAUGACUCGUUAUAGCGGAGAUAUAAACCUAAUUACCUCGAGAGGGG-3' | |
| Rep crRNA in Csm-40 | 5'-handle Spacer Rep<br>5'-ACGGAAACCAACGAGCCUAAAUUCAUAUGACUCGUUAUAG-3' | |
| Substrate | Length, nt | Sequence |
| Rep RNA | 72 | 3'-...CAAGGGAUGUUGCUCGGAUUUAAGUAAUACUGAGCAAUAUCGCCUGGCGCACAGACUAGGUGCCGCUGUAAC...5' |
| Lys crRNA in Csm-72 | 5'-handle Spacer Lys 3'-handle<br>5'-ACGGAAACUGUCUUCGACAUGGGUAAUCCUCAUGUUUGAAUGGCGAUAUAAACCUAAUUACCUCGAGAGGGG-3' | |
| Lys crRNA in Csm-40 | 5'-handle Spacer Lys<br>5'-ACGGAAACUGUCUUCGACAUGGGUAAUCCUCAUGUUUGAA-3' | |
| Substrate | Length, nt | Sequence |
| Lys RNA | 72 | 3'-...AAGAAACAACAGAAGCUGUACCCAUUAGGAGUACAAACUUACCGGCCGAGAUAAUCAUCUACGGCCUCAAA...5' |
| Cp crRNA in Csm-72 | 5'-handle Spacer Cp 3'-handle<br>5'-ACGGAAACUCUUUUAGGAGACCUUGCAUUGCCUUAAACAAUAAGCGAUAUAAACCUAAUUACCUCGAGAGGGG-3' | |

TABLE 5-continued (related to FIGS. 2, 3, 4, 5, and 6): Nucleic acid substrates used in this study. TABLE 5 discloses SEQ ID NOS 66-73, 68, 74, 72, 75, 69, 71, 73, 74, 76, 75 and 77-93, 133, 134 and 94-105, respectively, in order of appearance.

| | | |
|---|---|---|
| Cp crRNA in Csm-40 | 5'-handle Spacer Cp<br>5'-ACGGAAACUCUUUUAGGAGACCUUGCAUUGCCUUAACAAU-3' | |
| Substrate | Length, nt | Sequence |
| Cp RNA | 72 | 3'-...CCAAAAGGUAGAAAAUCCUCUGGAACGUAACGGAAUUGUUAUUCGAGGGUCAGCCUUAAGCAUCGCUUUAAC-5'<br>‖‖‖‖‖‖ ‖‖‖‖‖‖‖‖‖‖‖‖‖‖ ‖‖‖‖‖ ‖‖ ‖‖‖‖‖ |
| Mat crRNA in Csm-72 | 5'-handle Spacer Mat 3'-handle<br>5'-ACGGAAACAGUUUGCAGCUGGAUACGACAGACGGCCAUCUAACUGAUAUAAACCUAAAUUACCUCGAGAGGGG...3' | |
| Mat crRNA in Csm-40 | 5'-handle Spacer Mat<br>5'-ACGGAAACAGUUUGCAGCUGGAUACGACAGACGGCCAU-3' | |
| Substrate | Length, nt | Sequence |
| Mat RNA | 72 | 3'-...ACAGACCUUCAAACGUCGACCUAUGCUGUCCUGCCGGUAGAUUGAACUACAAUCAUGGCUGGACUGCAUGCCG...-5'<br>‖‖‖‖‖‖‖‖‖‖‖ ‖‖‖‖‖‖‖‖‖‖‖‖‖‖‖‖‖‖‖‖‖ ‖‖‖ |

*Above each Table crRNAs in Csm-72 and Csm-40 are depicted for clarity. Bold lettering in crRNAs represents the spacer (guide) sequence. Non-bold regions in crRNAs is for repeat sequences. Designed 72 and 40 nt crRNAs (+Tc) are complementary to tetracycline resistance gene (Tc) transcript and are guided to cleave RNA(+Tc) substrate (sense RNA or Tc transcript). Similarly, designed 72 and 40 nt crRNAs (-Tc) (antisense RNA corresponding the non-coding strand of Tc gene) substrate. Designed Rep, Lys, Cp and Mat 72 and 40 nt crRNAs are guided to cleave ss RNA coliphage M52 rep, lys, cp and mat transcripts, respectively. DNA and RNA substrates used in this study are presented in the Tables. Bold lettering in substrates represents the sequence complementary to spacer (guide) of crRNA. For single stranded DNA and RNA substrates nucleotides complementary to corresponding nucleotide in crRNA are depicted by dashes. Nucleotides marked in yellow were incorporated into RNA during in vitro transcription. Rep, Lys, Cp and Mat RNA are RNA sequences in MS2 genome.

What is claimed is:

1. A method of cleaving a target RNA in an animal, the method comprising:
   delivering a Type III Csm complex to an animal containing the target RNA, the Type III Csm complex comprising a crRNA capable of binding to a substantially complementary nucleotide sequence of the target RNA, and further comprising at least Csm3 and Csm4 or at least Csm3, Csm4, and Cas10, wherein the Type III Csm complex is configured to cleave the target RNA in the animal.

2. The method of claim 1, wherein Cas10 lacks DNase activity.

3. The method of claim 1, wherein the RNA to be cleaved encodes a reporter protein.

4. The method of claim 1, wherein the animal is a zebrafish.

5. A method of knockout or knockdown silencing a target RNA in an animal, the method comprising:
   delivering a Type III Csm complex to an animal containing the target RNA, the Type III Csm complex comprising a crRNA having a sequence substantially complementary for the target RNA to be silenced in the animal;
   the Type III Csm complex further comprising at least Csm3 and Csm4 proteins, or at least Csm3, Csm4, and Cas10; and wherein the Type III Csm complex is configured to knockout or knockdown the target RNA molecule in an animal.

6. The method of claim 5, where RNA silencing is transient.

7. The method of claim 5, wherein Cas10 contains a mutation in its active centre specifically, D16A in Cas10 from *Streptococcus thermophilus*, which inactivates the endonuclease activity and facilitates RNA knockout or knockdown.

8. The method of claim 5, wherein Csm3 contains a mutation in its active centre specifically, D33A in Csm3 from *Streptococcus thermophilus*, which inactivates the endoribonuclease activity and binding of ribonuclease-dead Csm complex with the target RNA results in RNA knockout or knockdown.

9. The method of claim 5, wherein the Type III Csm complex generates multiple cleavage sites in the target RNA molecule resulting in silencing of the target RNA.

10. The method of claim 5, wherein the target RNA molecule to be silenced is expressed from a transgene.

11. The method of claim 10, wherein the transgene comprises a promoter that is tissue specific in the animal.

12. The method of claim 5, wherein the target RNA molecule is expressed from an endogenous gene in the animal.

13. The method of claim 5, wherein the vertebrate is a zebrafish.

14. A method of assembling a Type III Csm complex in vitro, the method comprising:
  cloning nucleic acid sequences encoding at least crRNA, Csm3, and Csm4 or at least crRNA, Csm3, Csm4, and Cas10;
  expressing said nucleic acid sequences in bacteria; and
  isolating the expressed Type III Csm complex.

15. A composition comprising an engineered Csm complex, the Csm complex comprising only crRNA, Csm4, and Csm3, or only crRNA, Csm4, Csm3, and Cas10, wherein the crRNA of the engineered complex is configured for complementary binding to a selected site in a target RNA molecule, and wherein the engineered Csm complex is configured to knockout or knockdown the target RNA molecule in an animal.

* * * * *